United States Patent [19]
Jacobs et al.

[11] Patent Number: 5,785,934
[45] Date of Patent: *Jul. 28, 1998

[54] VAPOR STERILIZATION USING INORGANIC HYDROGEN PEROXIDE COMPLEXES

[75] Inventors: Paul Taylor Jacobs, Trabuco Canyon; Szu-Min Lin, Laguna Hills; Xiaolan Chen, Irvine, all of Calif.

[73] Assignee: Johnson & Johnson Medical, Inc., N.J.

[ * ] Notice: The term of this patent shall not extend beyond the expiration date of Pat. No. 5,667,753.

[21] Appl. No.: 716,094

[22] Filed: Sep. 19, 1996

Related U.S. Application Data

[63] Continuation-in-part of Ser. No. 549,425, Oct. 27, 1995, Pat. No. 5,667,753, which is a continuation-in-part of Ser. No. 369,786, Jan. 6, 1995, Pat. No. 5,674,450.

[51] Int. Cl.⁶ ........................................ A61L 9/00
[52] U.S. Cl. .................. 427/29; 422/1; 422/22; 422/295; 422/305; 423/587
[58] Field of Search ........................ 422/1, 22, 23, 422/28, 29, 33, 295, 305; 423/587

[56] References Cited

FOREIGN PATENT DOCUMENTS

| | | |
|---|---|---|
| 1097798A | 1/1995 | China . |
| 0679407A2 | 11/1995 | European Pat. Off. . |
| 9505341 | 8/1994 | WIPO . |

OTHER PUBLICATIONS

"Peroxides and Peroxy Compounds, Inorganic", *Kirk–Othmer Encyclopedia of Chemical Technology* vol. 17, p. 1–26, TP 9 E685 1978 V. 17.

K.V. Titova, E.I. Kolmakova, and I.P.Gelyuk, "Peroxosolvates of Sodium Phosphates $Na_3PO_4$—$5H_2O_2$", *Institute of New Chemical Problems, Russian Academy of Sciences*, pp. 721–725, Oct. 20, 1993.

N.V. Krivtsov, K.V. Titova, and V. Ya. Rosolovskii, "The Enthalpy of Dissolution and Standard Entholpy of Formation of Sodium Pyrophosphate Peroxosolvate $Na_4P_2O_7$—$3H_2O_2$", *Institute of New Chemical Problems, Russian Academy of Sciences*, pp. 625–627, Jul. 7, 1994.

N.V Krivtsov and K. V. Titova, "Enthalpy of Dissolution and Standard Enthalpy of Formation of $Na_2HPO_4$—$2H_2O_2$", *Kurnakov Institute of General and Inorganic Chemistry, Russian Academy of Sciences*, pp. 1741–1742, Feb. 2, 1993.

*Primary Examiner*—Krisanne Thornton
*Attorney, Agent, or Firm*—Knobbe, Martens, Olson & Bear, LLP

[57] ABSTRACT

An apparatus and process for hydrogen peroxide vapor sterilization of medical instruments and similar devices make use of hydrogen peroxide vapor released from an inorganic hydrogen peroxide complex. The peroxide vapor can be released at room temperature and atmospheric pressure; however, the pressure used can be less than 50 torr and the temperature greater than 86° C. to facilitate the release of hydrogen peroxide vapor. Preferred hydrogen peroxide complexes for use in the invention include $Na_4P_2O_7.3\ H_2O_2$ and $KH_2PO_4.H_2O_2$. The heating rate can be greater than 5° C. Optionally, a plasma can be used in conjunction with the vapor.

131 Claims, 27 Drawing Sheets

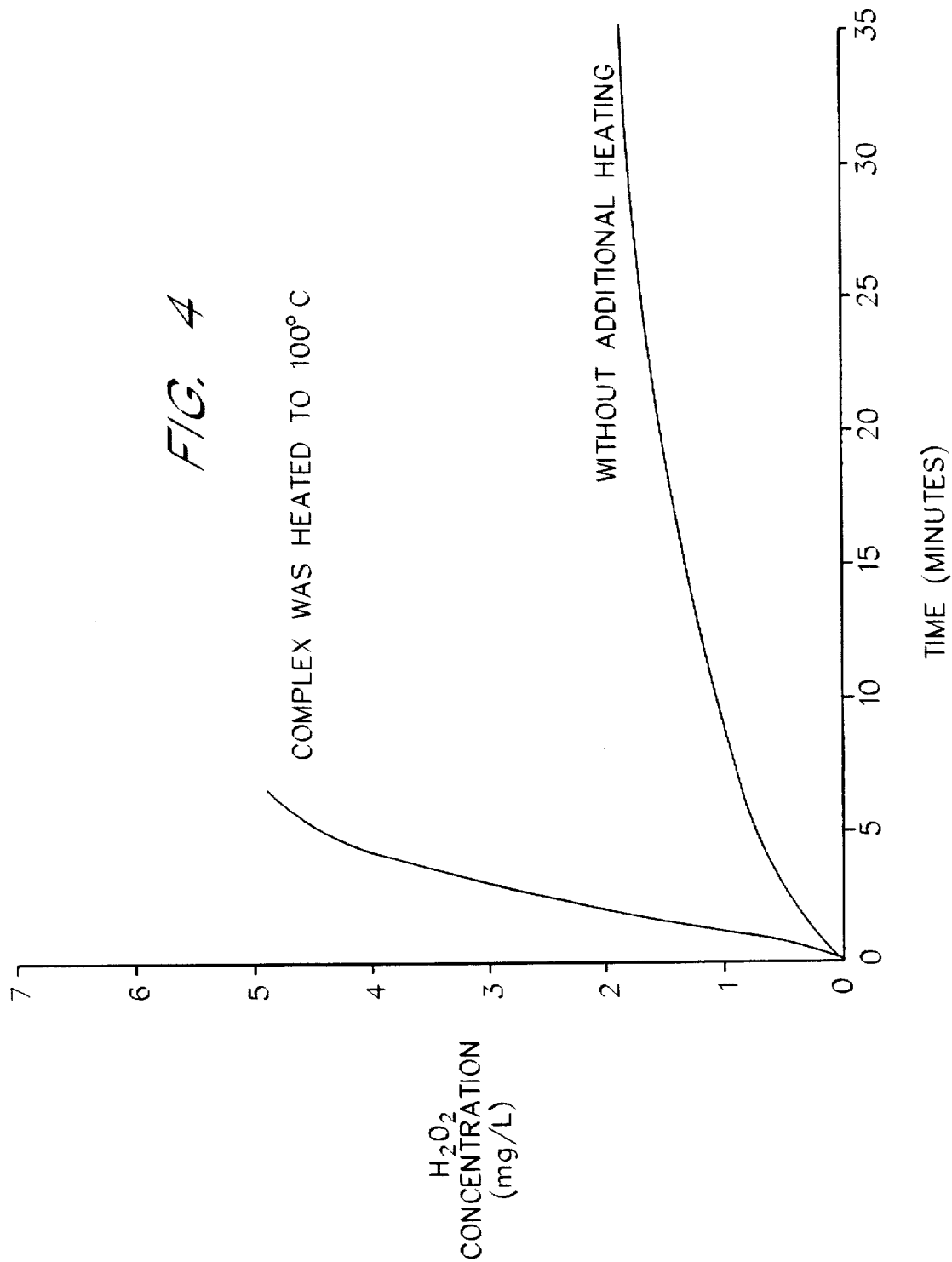

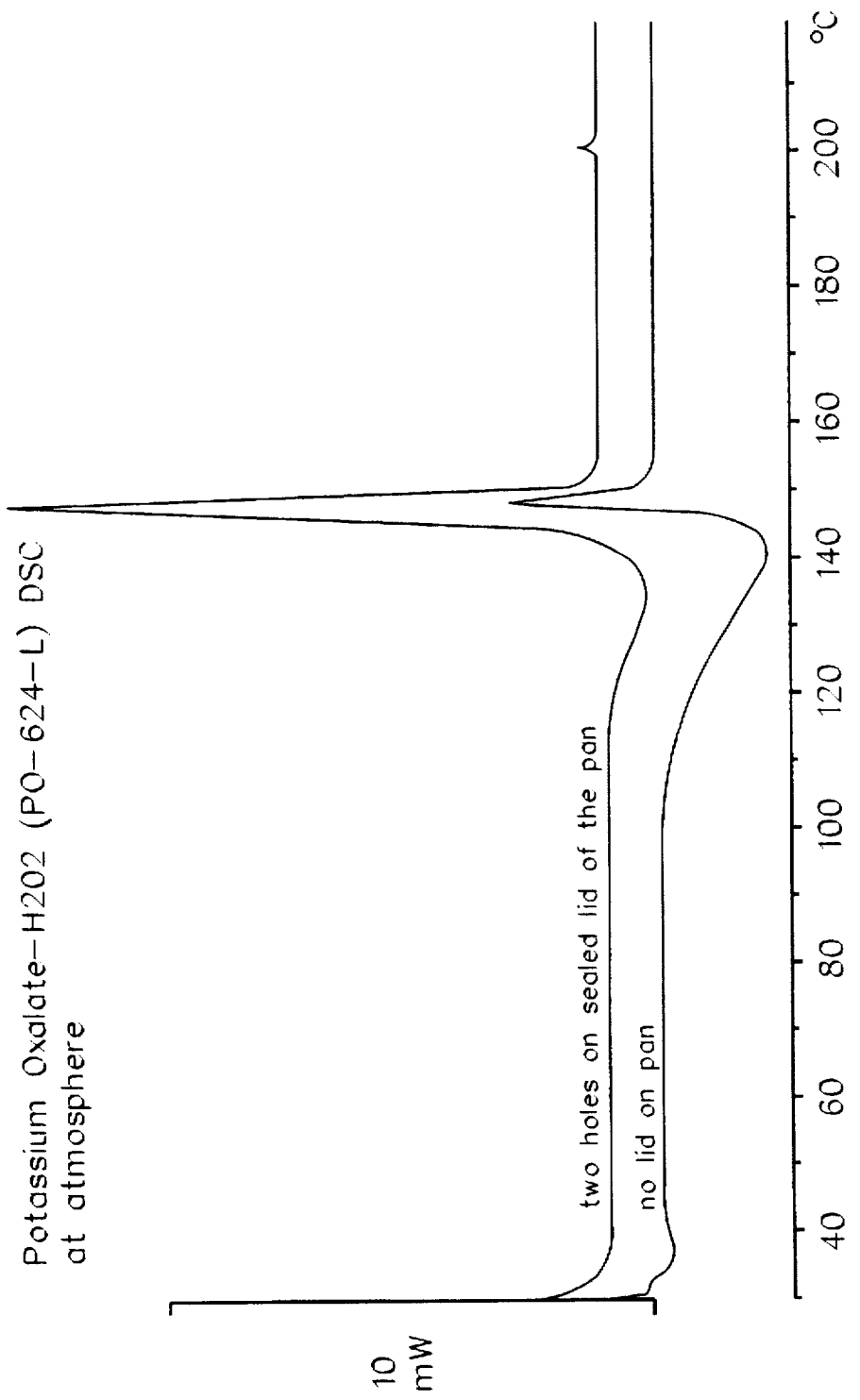

ent of allowed U.S.
VAPOR STERILIZATION USING INORGANIC HYDROGEN PEROXIDE COMPLEXES

RELATED APPLICATIONS

This application is a continuation-in-part of allowed U.S. patent application Ser. No. 08/549,425, filed Oct. 27, 1995, now U.S. Pat. No. 5,667,753, which is a continuation-in-part of allowed U.S. patent application Ser. No. 08/369,786, filed Jan. 6, 1995 now U.S. Pat. No. 5,674,450 the disclosures of which are hereby incorporated by reference.

BACKGROUND OF THE INVENTION

1. Field of the Invention

This invention relates to an apparatus and process for using hydrogen peroxide vapor to sterilize articles such as medical instruments, and more particularly to the use of an inorganic hydrogen peroxide complex for such a process.

2. Description of the Related Art

Medical instruments have traditionally been sterilized using either heat, such as is provided by steam, or a chemical, such as formaldehyde or ethylene oxide in the gas or vapor state. Each of these methods has drawbacks. Many medical devices, such as fiber optic devices, endoscopes, power tools, etc. are sensitive to heat, moisture, or both. Formaldehyde and ethylene oxide are both toxic gases that pose a potential hazard to healthcare workers. Problems with ethylene oxide are particularly severe, because its use requires long aeration times to remove the gas from articles that have been sterilized. This makes the sterilization cycle time undesirably long. In addition, both formaldehyde and ethylene oxide require the presence of a substantial amount of moisture in the system. Thus, devices to be sterilized must be humidified before the chemical is introduced or the chemical and moisture must be introduced simultaneously. Moisture plays a role in sterilization with a variety of other chemicals in the gas or vapor state, in addition to ethylene oxide and formaldehyde, as shown in Table 1.

TABLE 1

| Chemical | Relative Humidity Requirements for Optimal Efficacy | Literature Reference |
|---|---|---|
| Ethylene oxide | 25–50% | 1 |
| Propylene oxide | 25–50% | 1 |
| Ozone | 75–90% | 2 |
| Formaldehyde | >75% | 1 |
| Glutaraldehyde | 80–90% | 3 |
| Chlorine dioxide | 60–80% | 4 |
| Methyl bromide | 40–70% | 1 |
| β-Propiolactone | >75% | 1 |
| Peracetic acid | 40–80% | 5 |

1 Bruch, C. W. Gaseous Sterilization, Ann. Rev. Microbiology 15:245–262 (1961).
2 Janssen, D. W. and Schneider, P.M. Overview of Ethylene Oxide Alternative Sterilization Technologies, Zentralsterilisation 1:16–32 (1993).
3 Bovallius, A. and Anas, P. Surface-Decontaminating Action of Glutaraldehyde in the Gas-Aerosol Phase. Applied and Environmental Microbiology, 129–134 (Aug. 1977).
4 Knapp, J. E. et al. Chlorine Dioxide As a Gaseous Sterilant, Medical Device & Diagnostic Industry, 48–51 (Sept. 1986).
5 Portner, D.M. and Hoffman, R.K. Sporicidal Effect of Peracetic Acid Vapor, Applied Microbiology 16:1782–1785 (1968).

Sterilization using hydrogen peroxide vapor has been shown to have some advantages over other chemical sterilization processes (see, e.g., U.S. Pat. Nos. 4,169,123 and 4,169,124), and the combination of hydrogen peroxide with a plasma provides additional advantages, as disclosed in U.S. Pat. No. 4,643,876. In these disclosures the hydrogen peroxide vapor is generated from an aqueous solution of hydrogen peroxide, which ensures that there is moisture present in the system. These disclosures, together with those summarized in Table 1, teach that moisture is required for hydrogen peroxide in the vapor phase to be effective or to exhibit its maximum sporicidal activity. However, the use of aqueous solutions of hydrogen peroxide to generate hydrogen peroxide vapor for sterilization may cause problems. At higher pressures, such as atmospheric pressure, excess water in the system can cause condensation. Thus, one must reduce the relative humidity in a sterilization enclosure before introducing the aqueous hydrogen peroxide vapor.

The sterilization of articles containing diffusion-restricted areas, such as long narrow lumens, presents a special challenge for hydrogen peroxide vapor that has been generated from an aqueous solution of hydrogen peroxide, because:

1. Water has a higher vapor pressure than hydrogen peroxide and will vaporize faster than hydrogen peroxide from an aqueous solution.

2. Water has a lower molecular weight than hydrogen peroxide and will diffuse faster than hydrogen peroxide in the vapor state.

Because of this, when an aqueous solution of hydrogen peroxide is vaporized, the water reaches the items to be sterilized first and in higher concentration. The water vapor therefore restricts penetration of hydrogen peroxide vapor into diffusion restricted areas, such as small crevices and long narrow lumens. Removing water from the aqueous solution and using more concentrated hydrogen peroxide can be hazardous, due to the oxidizing nature of the solution.

U.S. Pat. Nos. 4,642,165 and 4,744,951 attempt to solve this problem. The former discloses metering small increments of a hydrogen peroxide solution onto a heated surface to ensure that each increment is vaporized before the next increment is added. Although this helps to eliminate the difference in the vapor pressure and volatility between hydrogen peroxide and water, it does not address the fact that water diffuses faster than hydrogen peroxide in the vapor state.

The latter patent describes a process for concentrating hydrogen peroxide from a relatively dilute solution of hydrogen peroxide and water and supplying the concentrated hydrogen peroxide in vapor form to a sterilization chamber. The process involves vaporizing a major portion of the water from the solution and removing the water vapor produced before injecting the concentrated hydrogen peroxide vapor into the sterilization chamber. The preferred range for the concentrated hydrogen peroxide solution is 50% to 80% by weight. This process has the disadvantage of working with solutions that are in the hazardous range; i.e., greater than 65% hydrogen peroxide, and also does not remove all of the water from the vapor state. Since water is still present in the solution, it will vaporize first, diffuse faster, and reach the items to be sterilized first. This effect will be especially pronounced in long narrow lumens.

U.S. Pat. No. 4,943,414 discloses a process in which a vessel containing a small amount of a vaporizable liquid sterilant solution is attached to a lumen, and the sterilant vaporizes and flows directly into the lumen of the article as the pressure is reduced during the sterilization cycle. This system has the advantage that the water and hydrogen peroxide vapor are pulled through the lumen by the pressure differential that exists, increasing the sterilization rate for lumens, but it has the disadvantage that the vessel needs to be attached to each lumen to be sterilized. In addition, water is vaporized faster and precedes the hydrogen peroxide vapor into the lumen.

U.S. Pat. No. 5,008,106 discloses that a substantially anhydrous complex of PVP and $H_2O_2$ is useful for reducing the microbial content of surfaces. The complex, in the form of a fine white powder, is used to form antimicrobial solutions, gels, ointments, etc. It can also be applied to gauze, cotton swabs, sponges and the like. The $H_2O_2$ is released upon contact with water present on the surfaces containing the microbes. Thus, this method too requires the presence of moisture to effect sterilization.

Certain inorganic hydrogen peroxide complexes have been reported including examples within the following classes: alkali metal and ammonium carbonates, alkali metal oxalates, alkali metal phosphates, alkali metal pyrophosphates, fluorides and hydroxides. U.S.S.R. patent document No. SU 1681860 (Nikolskaya et al.) discloses that surfaces can be decontaminated, although not necessarily sterilized, using ammonium fluoride peroxohydrate ($NH_4F \cdot H_2O_2$). However, this inorganic peroxide complex provides decontamination only within the very narrow temperature range of 70°–86° C. Even within this range, decontamination times were quite long, requiring at least two hours. Additionally, it is known that ammonium fluoride decomposes to ammonia and hydrofluoric acid at temperatures above 40° C. Due to its toxicity and reactivity, hydrofluoric acid is undesirable in most sterilization systems. Moreover, Nikolskaya et al. disclose that despite the release of 90% of its hydrogen peroxide at 60° C., $NH_4F \cdot H_2O_2$ is ineffective at decontamination of surfaces at this temperature. Thus, it appears that a factor other than hydrogen peroxide is responsible for the decontamination noted.

Hydrogen peroxide is capable of forming complexes with both organic and inorganic compounds. The binding in these complexes is attributed to hydrogen bonding between electron rich functional groups in the complexing compound and the peroxide hydrogen. The complexes have been used in commercial and industrial applications such as bleaching agents, disinfectants, sterilizing agents, oxidizing reagents in organic synthesis, and catalysts for free-radical-induced polymerization reactions.

Generally, these types of compounds have been prepared by the crystallization of the complex from an aqueous solution. For example, urea hydrogen peroxide complex was prepared by Lu et al. (*J. Am. Chem. Soc.* 63(1):1507–1513 (1941)) in the liquid phase by adding a solution of urea to a solution of hydrogen peroxide and allowing the complex to crystallize under the proper conditions. U.S. Pat. No. 2,986,448 describes the preparation of sodium carbonate hydrogen peroxide complex by treating a saturated aqueous solution of $Na_2CO_3$ with a solution of 50 to 90% $H_2O_2$ in a closed cyclic system at 0° to 5° C. for 4 to 12 hours. More recently, U.S. Pat. No. 3,870,783 discloses the preparation of sodium carbonate hydrogen peroxide complex by reacting aqueous solutions of hydrogen peroxide and sodium carbonate in a batch or continuous crystallizer. The crystals are separated by filtration or centrifugation and the liquors used to produce more sodium carbonate solution. Titova et al. (*Zhurnal Neorg. Khim.*, 30:2222–2227, 1985) describe the synthesis of potassium carbonate peroxyhydrate ($K_2CO_3 \cdot 3 H_2O_2$) by reaction of solid potassium carbonate with an aqueous solution of hydrogen peroxide at low temperature followed by crystallization of the complex from ethanol. These methods work well for peroxide complexes that form stable, crystalline free-flowing products from aqueous solution.

U.S. Pat. Nos. 3,376,110 and 3,480,557 disclose the preparation of a complex of hydrogen peroxide with a polymeric N-vinylheterocyclic compound (PVP) from aqueous solution. The resultant complexes contained variable amounts of hydrogen peroxide and substantial amounts of water. U.S. Pat. No. 5,008,093 teaches that free-flowing, stable, substantially anhydrous complexes of PVP and $H_2O_2$ could be obtained by reacting a suspension of PVP and a solution of $H_2O_2$ in an anhydrous organic solvent like ethyl acetate. More recently, U.S. Pat. No. 5,077,047 describes a commercial process for producing the PVP-hydrogen peroxide product by adding finely divided droplets of a 30% to 80% by weight aqueous solution of hydrogen peroxide to a fluidized bed of PVP maintained at a temperature of ambient to 60° C. The resultant product was found to be a stable, substantially anhydrous, free flowing powder with a hydrogen peroxide concentration of 15 to 24%.

U.S. Pat. No. 5,030,380 describes the preparation of a solid polymeric electrolytic complex with hydrogen peroxide by first forming a complex in aqueous solution and then drying the reaction product under vacuum or by spray drying at a low enough temperature to avoid thermal degradation of the product.

Titova et al. (*Russ. J. Inorg. Chem.*, 40:384–387, 1995) formed a $Na_4P_2O_7 \cdot 3 H_2O_2$ complex by mixing $Na_4P_2O_7 \cdot 10 H_2O$ with a 30–90% $H_2O_2$ solution followed by vacuum drying. The complex was observed to partially decompose under isothermic exposure for two hours at 120° C. and 140° C.

All of these previous methods of preparing hydrogen peroxide complexes use solutions of hydrogen peroxide. Either the complex is formed in a solution containing hydrogen peroxide or droplets of a hydrogen peroxide solution are sprayed onto a fluidized bed of the reactant material.

Vapor phase and gas phase reactions are well known synthesis methods. For example, U.S. Pat. No. 2,812,244 discloses a solid-gas process for dehydrogenation, thermal cracking, and demethanation. Fujimoto et al. (*J. Catalysis*, 133:370–382 (1992)) described a vapor-phase carboxylation of methanol. Zellers et al. (*Anal Chem.*, 62:1222–1227 (1990)) discussed the reaction of styrene vapor with a square-plannar organoplatinum complex. These prior art vapor- and gas-phase reactions, however, were not used to form hydrogen peroxide complexes.

SUMMARY OF THE INVENTION

One aspect of the present invention relates to an apparatus for hydrogen peroxide sterilization of an article. This apparatus includes a container for holding the article to be sterilized, and a source of hydrogen peroxide vapor in fluid communication with the container. The source includes an inorganic hydrogen peroxide complex which does not decompose to form a hydrohalic acid, and is configured so that the vapor can contact the article to effect sterilization. The apparatus optionally includes a breathable barrier. The source of hydrogen peroxide vapor can be located within the container, or can also be located in an enclosure which is in fluid communication with the container. If an enclosure is provided, a valve can be included between the enclosure and the container. A heater can be included which is adapted to heat the inorganic hydrogen peroxide complex. Where the complex is within the container, a heater can also be adapted to heat the container. Alternatively, where an enclosure is provided containing the peroxide complex, a heater can be adapted to heat the enclosure. Thus, a preferred embodiment encompasses three heaters, one for heating each of the container, the complex and the enclosure. Another optional element of the apparatus is a pump to evacuate the container. If an enclosure is provided, the pump can be adapted to evacuate the container and the enclosure, preferably independently. Thus, the apparatus can also include two pumps, one adapted to evacuate the container and a second pump adapted to evacuate the enclosure. A vent valve is also optionally included which is adapted to vent the container. If an enclosure is included, a first vent valve can be adapted to vent the container and a second vent valve can be adapted to vent the enclosure independently of the first vent valve. Still another optional component of the apparatus is a mechanism for generating a plasma. The plasma can be generated within the container or outside thereof. A variety of complexes can be used. The complex is preferably in a solid phase. In one embodiment, the complex is a hydrogen peroxide complex of a phosphate or condensed phosphate salt. In other embodiments, the complex is a hydrogen peroxide complex of an oxalate salt, a carbonate salt, a sulfate salt or a silicate salt.

Another aspect of the present invention relates to a method for hydrogen peroxide vapor sterilization of an article. This method includes the step of contacting the article with hydrogen peroxide vapor released from an inorganic hydrogen peroxide complex to sterilize the article. The peroxide complex used does not decompose to a hydrohalic acid. Preferably, the complex has less than 10% water and is performed at a temperature of 25° C. or less. When using certain complexes, the complex can be heated so as to facilitate the release of the vapor from the complex. For many of these complexes, the complex is preferably heated to a temperature greater than 86° C. Preferably, the heating is performed at a rate of at least 5° C./minute, more preferably at least 10° C./minute, still more preferably at least 50° C./minute, and most preferably at a rate of at least 1000° C./minute. In one embodiment, the heating is accomplished by contacting the complex with a pre-heated heater. The method can be performed at atmospheric or subatmospheric pressure. In certain embodiments, the container is evacuated before introducing the vapor into the container. If the method is performed at subatmospheric pressure, it is preferably brought to a pressure of less than 50 torr, more preferably less than 20 torr, and most preferably less than 10 torr. The peroxide complex can be provided within an enclosure, in which case, the pressures of the container and the enclosure can be the same or different. The evacuating step is preferably conducted before the step of contacting the article with the vapor. An optional step is generating a plasma around the article after introducing the vapor into the container. Such a plasma can be generated inside the container or the plasma can be generated outside the container and flowed inside the container and around the article. Other optional steps are pressure pulsing of the vapor during the contacting step, or venting to a pressure less than or equal to atmospheric pressure. A variety of inorganic complexes can be used. In one preferred embodiment, the complex is a complex of a phosphate or condensed phosphate salt with hydrogen peroxide, such as a salt of potassium or sodium, magnesium or calcium. In this embodiment, one preferred complex is a hydrogen peroxide complex with $Na_4P_2O_7$, preferably one with two or more molecules of hydrogen peroxide, more preferably still $Na_4P_2O_7 \cdot 3\ H_2O_2$. Other preferred complexes are a hydrogen peroxide complex with $Na_3PO_4$, $Na_2HPO_4$, $Na_5P_3O_{10}$, $K_3PO_4$, $K_4P_2O_7$ (especially one having two or more $H_2O_2$ molecules), $K_2HPO_4$, $KH_2PO_4$ (especially $KH_2PO_4 \cdot H_2O_2$) and $Ca_2P_2O_7$, $Mg_2P_2O_7$. In another embodiment, the inorganic complex is a complex of hydrogen peroxide with an oxalate salt. A preferred oxalate salt complex is a hydrogen peroxide complex with $K_2C_2O_4$, especially $K_2C_2O_4 \cdot H_2O_2$. The inorganic complex can also be a complex of hydrogen peroxide with a carbonate salt, such as one of sodium, potasssium or rubidium. Preferred carbonate salt complexes include $Na_2CO_3$ (especially $Na_2CO_3 \cdot 1.5\ H_2O_2$), $K_2CO_3$, $NaHCO_3$, $KHCO_3$ and $Rb_2CO_3$. In another embodiment, the complex is a complex of hydrogen peroxide with a sulfate salt, such as a sodium or potassium salt thereof. Preferred sulfate salt complexes include complexes of hydrogen peroxide with $Na_2SO_4$ and $K_2SO_4$. Still another embodiment is where the inorganic complex is a complex of hydrogen peroxide with a silicate salt, such as a sodium salt thereof. Preferred silicate salt complexes include complexes of hydrogen peroxide with $Na_2SiO_3$ or $Na_2Si_3O_7$. Many of the preferred complexes, and others, release hydrogen peroxide at atmospheric pressure and room temperature. However, for some complexes the peroxide is released at a pressure less than atmospheric pressure. In an alternative embodiment, the contacting step includes the hydrogen peroxide from a second source thereof. The second source can be a second hydrogen peroxide complex, including an organic hydrogen peroxide complex. In some embodiments, a mixture of hydrogen peroxide complex provides the source of peroxide vapor. This mixture can be either a physical mixture or a chemical mixture, as those terms are defined hereinbelow.

A further aspect of the invention relates to another method for hydrogen peroxide vapor sterilization of an article. This method includes contacting the article with hydrogen peroxide vapor released from a $Na_4P_2O_7$ hydrogen peroxide complex by heating the complex so as to produce hydrogen peroxide vapor that can contact and sterilize the article. In a preferred embodiment, the $Na_4P_2O_7$ complex is $Na_4P_2O_7 \cdot 3\ H_2O_2$. The contacting step can be conducted at atmospheric pressure, or the container can be evacuated, such that when the vapor is into the container, the container is at a pressure of less than 50 torr. The complex can also be heated to a temperature of approximately 175° C. to effectively release the vapor. The article can be placed into a container prior to the contacting step.

Still another aspect of the invention is yet another method for hydrogen peroxide sterilization of an article. This method includes placing the article in a container, placing a hydrogen peroxide complex with an inorganic salt which does not decompose to form a hydrohalic acid into vapor communication with the container, and allowing the container to stand at a temperature below about 70° C. for a time sufficient to release hydrogen peroxide vapor from the complex to effect sterilization of the article. The container can be any of a number of types of containers, including a pouch, chamber or room. In one preferred embodiment, the inorganic salt is a salt of a phosphate or condensed phosphate. In other embodiments, the inorganic salt is a salt of an oxalate, a carbonate, a sulfate or a silicate. In certain embodiments of this aspect of the invention, the container is allowed to stand at a pressure less than atmospheric pressure and/or at a temperature below about 40° C. In certain embodiments, the complex is heated to a temperature greater than 23° C. to facilitate release of the vapor. The hydrogen peroxide complex can come in a variety of forms, including a powder and a tablet. In some embodiments, the hydrogen peroxide complex is within an enclosure. If an enclosure is provided, the enclosure can be either inside or outside the container. The enclosure can be selectively separated from the container by a valve, and in some embodiments can be detached from container. The container can be sealed, preferably with a gas permeable material. Preferred gas permeable materials include TYVEK™, CSR wrap and paper. An optional step is exposing the article to plasma, and when a detachable enclosure is provided, the article is preferably exposed to plasma after detaching the enclosure from the container.

Yet one more aspect of the present invention relates to a method for hydrogen peroxide sterilization of an article having an exterior and a narrow lumen therein. This method includes connecting a vessel containing a hydrogen peroxide complex to the lumen of the article, placing the article within a container, evacuating the container, and contacting the lumen of the article with hydrogen peroxide vapor released from the hydrogen peroxide complex. The hydrogen peroxide complex is a complex which does not decompose to form a hydrohalic acid. Any of a number of such complexes can be used, such as a complex of a phosphate or condensed phosphate salt, an oxalate salt, a carbonate salt, a sulfate salt and a silicate salt. Optionally, the exterior of the article can be contact with a second source of sterilant, which can be any of a number of suitable sterilants, such as the same hydrogen peroxide complex as in the vessel, a different hydrogen peroxide complex as in the vessel, liquid hydrogen peroxide or chlorine dioxide. Another optional step is to expose the article to plasma.

BRIEF DESCRIPTION OF THE DRAWINGS

FIG. 4 is a graph depicting the release of hydrogen peroxide vapor from a vacuum unstable non-aqueous glycine anhydride peroxide complex.

FIG. 10 shows the effect of an open aluminum pan and a pan with two holes on a lid covering the complex on the DSC curves of $K_2C_2O_4.H_2O_2$ at atmospheric pressure.

DETAILED DESCRIPTION OF THE INVENTION

Figure 1:
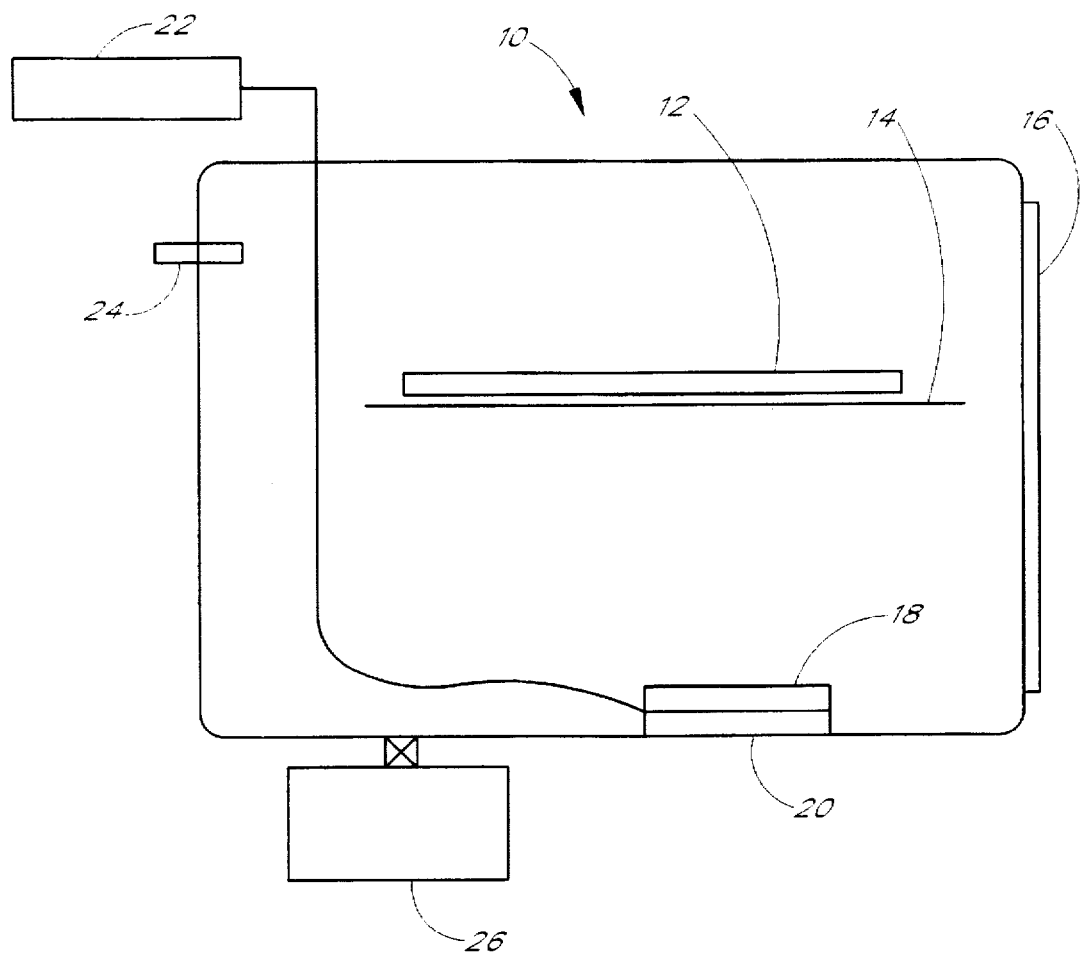
FIG. 1 is a schematic of a vapor sterilization apparatus of the present invention.

Hydrogen peroxide sterilizers that have been used in the past invariably used an aqueous solution of hydrogen peroxide as their source of sterilant. These sterilizers have disadvantages caused by the presence of water in the system. At higher pressure, such as atmospheric pressure, the excess water in the system can cause condensation. This requires that an extra step be performed to reduce the relative humidity of the atmosphere in an enclosure to be sterilized to an acceptable level before the aqueous hydrogen peroxide vapor is introduced. These sterilizers also have drawbacks caused by the facts that water, having a higher vapor pressure, vaporizes more quickly than hydrogen peroxide from an aqueous solution; and water, having a lower molecular weight, diffuses faster than hydrogen peroxide. When a medical device or the like is enclosed in a sterilizer, the initial sterilant that reaches the device from the hydrogen peroxide source is diluted in comparison to the concentration of the source. The dilute sterilant can be a barrier to sterilant that arrives later, particularly if the device being sterilized is an article, such as an endoscope, that has narrow lumens. Using a concentrated solution of hydrogen peroxide as the source in an attempt to overcome these drawbacks is unsatisfactory, because such solutions are hazardous.

In the present invention, the shortcomings of hydrogen peroxide sterilizers of the prior art are overcome by using a substantially non-aqueous (i.e., substantially anhydrous) source of hydrogen peroxide which releases a substantially non-aqueous hydrogen peroxide vapor. In a preferred embodiment, the substantially non-aqueous hydrogen peroxide vapor is produced directly from a substantially non-aqueous hydrogen peroxide complex. However, the substantially non-aqueous hydrogen peroxide vapor can also be generated from an aqueous complex which is processed during vaporization to remove water, such as under vacuum. Thus, where an aqueous hydrogen peroxide complex is used, the aqueous complex can be converted to a substantially non-aqueous hydrogen peroxide complex while carrying out the process of the present invention. Preferably, the substantially non-aqueous hydrogen peroxide complexes contain less than about 20% water, more preferably no more than about 10% water, still more preferably no more than about 5% water, and most preferably no more than about 2% water.

As is apparent from the preferred percentages of water in the substantially non-aqueous hydrogen peroxide complexes used in the present invention, as provided above, the most preferred hydrogen peroxide complex and the peroxide vapor generated therefrom are substantially water-free. Nevertheless, as is also apparent from these figures, some water can be present in the system. Some of this water may derive from the decomposition of hydrogen peroxide to form water and oxygen as byproducts and some hydrogen binding of this water to the complex can occur.

The effect of water was measured in a series of tests, with a sterilization chamber maintained at various relative humidities. Test conditions were those described in Example 1, below, with spores supported on stainless steel (SS) blades in 3 mm×50 cm stainless steel lumens. As shown in Table 2, under the test conditions, 5% relative humidity has no effect on efficacy but 10% relative humidity decreases the sterilization rate. This example shows that small amounts of moisture can be allowed in the system with the hydrogen peroxide generated from the non-aqueous peroxide complex and the presence of water in the system can be overcome by increasing the exposure time.

TABLE 2

Effects of Relative Humidity on Efficacy
SS Blades in 3 mm × 50 cm SS Lumens

| Diffusion Time | Sterility Results (Positive%Samples) | | |
|---|---|---|---|
| | 1% RH | 5% RH | 10% RH |
| 5 | 0/3 | 0/3 | 3/3 |
| 10 | 0/3 | 0/3 | 2/3 |
| 15 | 0/3 | 0/3 | 0/3 |
| 30 | 0/3 | 0/3 | 0/3 |

A primary criterion for the composition of the hydrogen peroxide source is the relationship between its stability and hydrogen peroxide evaporation rate as a function of temperature and pressure. Depending on the parameters of the sterilization process—e.g. pressure, temperature, etc.—a higher or lower peroxide evaporation rate may be preferred, and heating the peroxide source may or may not be required. The need for heating of the peroxide complex depends on the vapor pressure of the complex. Some peroxide complexes have a sufficiently high vapor pressure that a significant amount of hydrogen peroxide vapor can be released without heating the complex. In general, heating the complex increases the vapor pressure of hydrogen peroxide and accelerates the release of peroxide from the complex.

To provide a desirably high evaporation rate, the source should preferably have a large surface area. Thus the source may be a fine powder or a coating on a material that has a large surface area. Of course, safety, availability, and cost of the material are also important criteria. The release of hydrogen peroxide from hydrogen peroxide complexes with urea, polyvinylpyrrolidone, nylon-6, glycine anhydride, and 1,3 dimethyl urea were evaluated. The complexes of hydrogen peroxide with urea, polyvinylpyrrolidone, nylon-6, and glycine anhydride are solids. The 1,3 dimethyl urea peroxide complex is a liquid. The glycine anhydride hydrogen peroxide complex is a less stable complex under reduced pressure than the other complexes evaluated, and under vacuum conditions, most of the hydrogen peroxide can be released from the complex without the need for additional heating.

Urea hydrogen peroxide complex is available in tablet form from Fluka Chemical Corp., Ronkonkoma, N.Y. and in powder form from Aldrich Chemical Co., Milwaukee, Wis. This complex is also known as urea peroxide, hydrogen peroxide urea complex, peroxide urea, peroxide urea adduct, urea peroxide adduct, percarbamide, carbamide perhydrate, and carbamide peroxide. As used herein, the term "urea peroxide" encompasses all of the foregoing terms.

The polyvinylpyrrolidone-hydrogen peroxide complex ($PVP-H_2O_2$) can be prepared by the method disclosed in International Application Pub. No. WO 92/17158. Alternatively, the complexes with PVP, with nylon-6, with 1,3 dimethylurea and with glycine anhydride, as well as with other organic and inorganic compounds can be prepared by the method disclosed in detail below.

Achieving suitable evaporation rates of anhydrous peroxide vapor from the source may be facilitated by elevated temperatures and/or reduced pressure. Thus, a heater for the peroxide source and/or a vacuum pump to evacuate the sterilization chamber are preferably a part of the sterilizer. Preferably, the source is covered with a layer of gas permeable material, such as TYVEK™ nonwoven polyethylene fabric, nonwoven polypropylene such as SPUNGUARD™, or similar material, which permits the peroxide vapor to pass but not the peroxide complexing material. Perforated aluminum or other suitable perforated material could also be used as a cover.

Figure 3A:
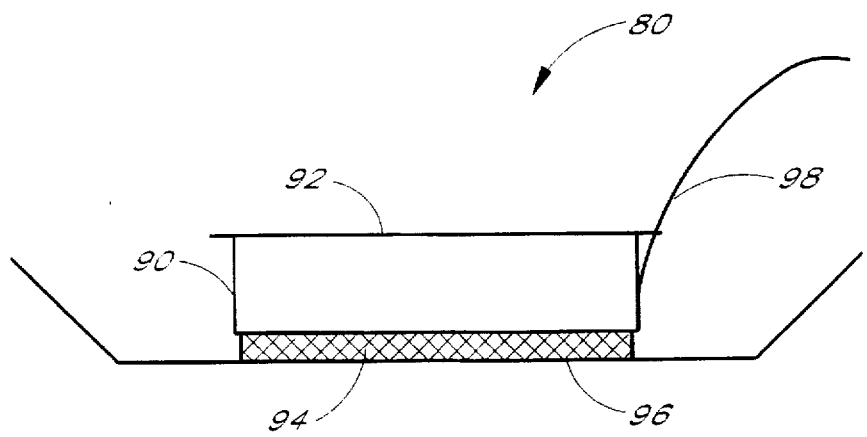
FIG. 3A is a schematic of a device which can be used for heating peroxide complexes.

FIG. 3A shows a device 80 that can be used to measure release of hydrogen peroxide from hydrogen peroxide complexes under various temperature conditions. In this device, an aluminum pan 90 is covered with a gas permeable layer 92, such as a layer of medical grade TYVEK™. The pan 90 is placed on top of a heating pad 94 which is placed in a pyrex pan 96. A thermocouple thermometer 98 is placed on the outside of the pan 90 approximately 1 cm from the bottom thereof. In a preferred embodiment, aluminum pan 90 is open to the atmosphere to allow greater release of the postassium oxalate hydrogen peroxide complex at atmospheric pressure.

Figure 3B:
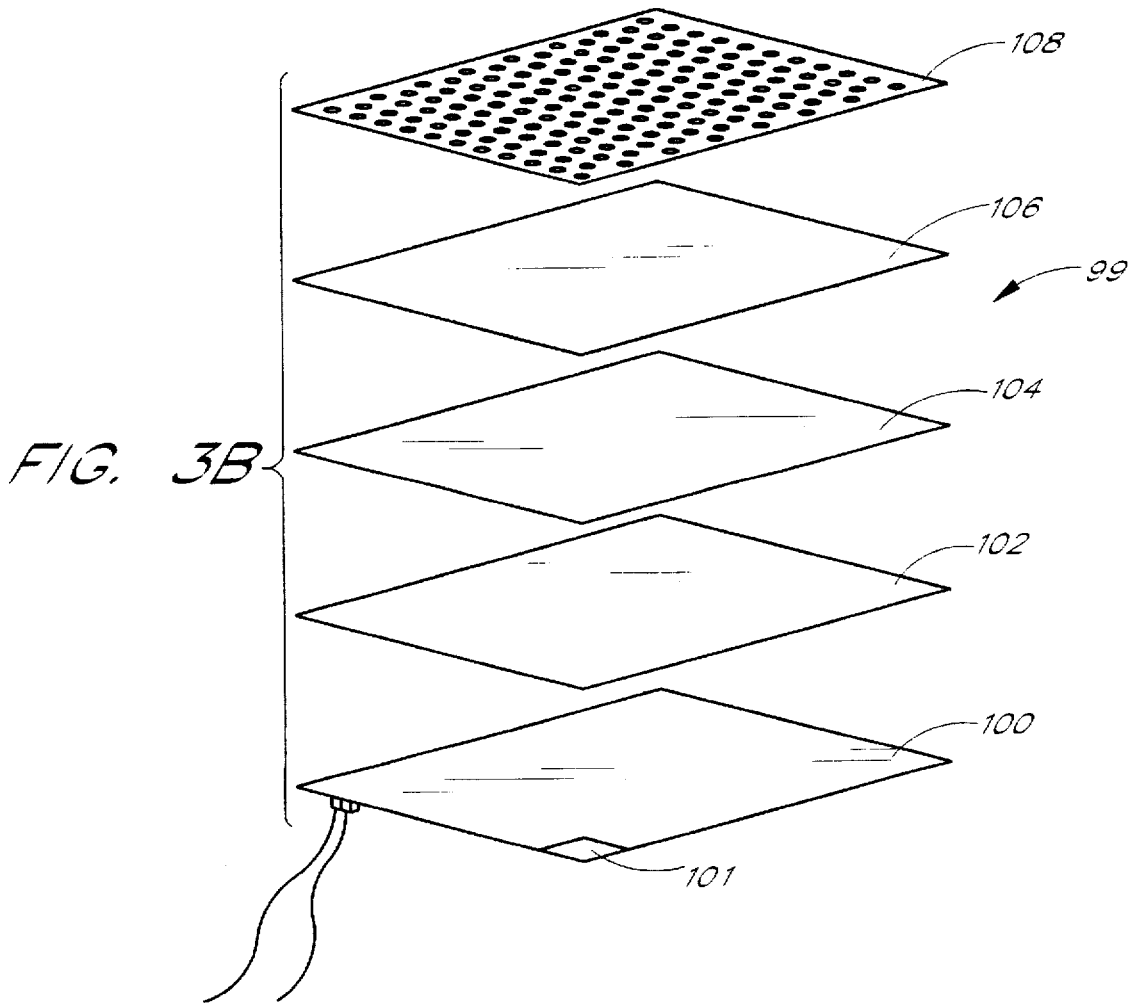
FIG. 3B is a schematic of a preferred container for holding the peroxide source for sterilization according to the present invention.

A preferred container 99 for holding the peroxide source is illustrated in FIG. 3B. The container 99 comprises a metal plate 100, e.g. an aluminum plate, with an optional attached heater used to heat the solid peroxide complex. A temperature monitor 101, such as a thermometer, can be placed on the plate 100 to monitor the temperature. The peroxide complex is placed directly on the plate 100. Alternatively, in order to provide even heating of all the peroxide complex, the peroxide complex can be placed between one or more aluminum screens 102, 104 placed on top of the plate 100. The aluminum screens 102, 104 provide greater surface area and even heating of the complex when larger amounts of peroxide complex are being used. The peroxide complex, or the screen or screens 102, 104, are then covered with a gas permeable layer 106, such as a layer of medical grade TYVEK™ or SPUNGUARD™, so that the hydrogen peroxide released from the complex passes through the covering 106 before diffusing into the rest of the chamber. A perforated aluminum plate 108 is optionally placed on top of the TYVEK™ or SPUNGUARD™ layer 106 to provide pressure to keep the complex in contact with the heated plate 100 and to ensure even heating of the peroxide complex.

The device just described provides even heating of the complex, which results in an increased amount of hydrogen peroxide vapor being released from the peroxide complex.

FIG. 1 depicts a schematic of a hydrogen peroxide vapor sterilization apparatus of the present invention. Chamber 10 holds an article 12 which is to be sterilized and which, for convenience, is placed on shelf 14. Door 16 provides access to the interior of chamber 10. A non-aqueous source of hydrogen peroxide 18 is depicted on optional heater 20, which is controlled by temperature controller 22. The peroxide concentration can be monitored by optional monitor 24. If desired, chamber 10 can be evacuated using pump 26; however, sterilization can also be accomplished at atmospheric pressure.

The container that holds the articles to be sterilized can be a conventional sterilization chamber, which is evacuated, or it can be a container (or a room) at atmospheric pressure.

The time required to sterilize the articles depends on the nature, number and packaging of the articles and their placement in the chamber. Alternatively, it may be the chamber itself (or an entire room) that is being sterilized. In any case, optimum sterilization times can be determined empirically.

The use of pressure pulsing to enhance the penetration and antimicrobial activity of sterilant gases, which is well known in the sterilization art, can also be applied to the non-aqueous hydrogen peroxide process. One exemplary process of pressure pulsing, which can be adapted for use in connection with the methods and apparatuses described herein, is described in U.S. Pat. No. 5,527,508, the disclosure of which is hereby incorporated by reference. As described in additional detail hereinbelow, plasma can also be used to further enhance activity and/or to remove residuals.

At the conclusion of the sterilization process excess hydrogen peroxide can be removed from devices that have an affinity for peroxide by exchanging the air in contact with the devices. This can be accomplished by flowing warm air over the devices for an extended time or by evacuating the chamber.

Articles that have previously been sterilized by exposure to hydrogen peroxide vapor may also be exposed to the plasma to remove residual hydrogen peroxide that may remain on the articles. Since the hydrogen peroxide is decomposed into non-toxic products during the plasma treatment, the sterilized articles may be used without the need for any additional steps.

It may be desirable to isolate the peroxide source from the sterilizer after the peroxide vapor is released to avoid reabsorption of the vapor or, when a plasma is used, to avoid exposing the source to the plasma. Isolation is also advantageous when the complex used is not stable under vacuum. Isolation can be accomplished using valves or other isolating devices well known in the art.

Figure 2:
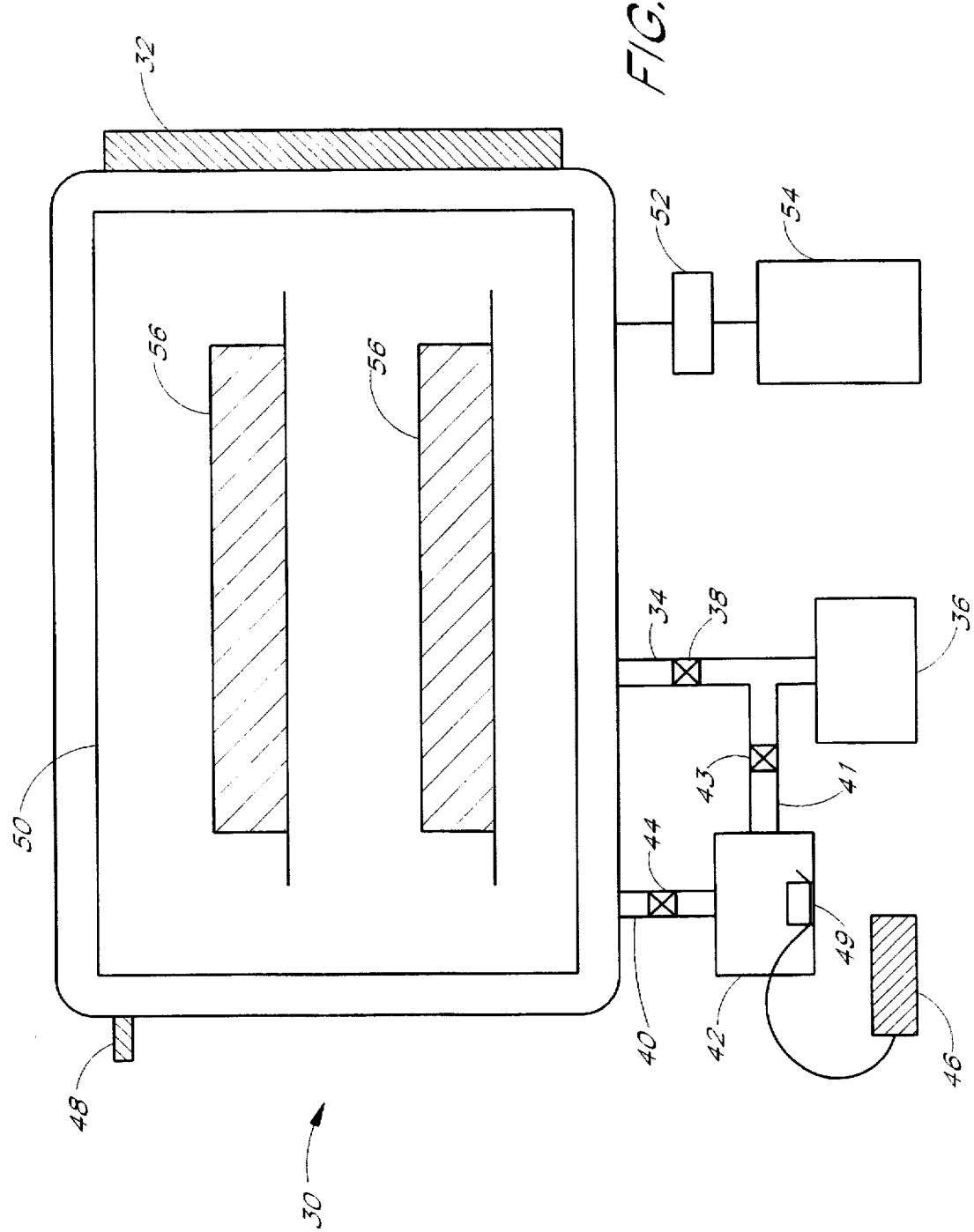
FIG. 2 is a schematic of a vapor sterilization apparatus of the present invention which includes an electrode which is optionally used to generate plasma.

FIG. 2 depicts a schematic of a hydrogen peroxide plasma sterilization system of the present invention. Sterilization can be achieved with or without the use of plasma. The plasma can be used to enhance the sporicidal activity of the peroxide vapor, and/or to remove any residual hydrogen peroxide remaining on the sterilized articles.

Sterilization is carried out in chamber 30, which includes a door or opening 32 through which articles to be sterilized can be introduced. The chamber 30 includes an outlet 34 to a vacuum pump 36, through which the chamber can be evacuated. The outlet 34 contains a valve 38 to isolate the chamber from the vacuum pump 36. The chamber 30 also includes an inlet 40 attached to an enclosure 42 that contains the hydrogen peroxide complex. Inlet 40 contains a valve 44 that allows enclosure 42 to be isolated from the chamber. The sterilization system also contains an inlet 41 which connects the enclosure 42 and the vacuum pump 36, which contains a valve 43. This system allows the simultaneous evacuation of both enclosure 42 and chamber 30, or the independent evacuation of either enclosure 42 or chamber 30. Evacuation is controlled by the opening and closing of the valves 38, 44, and 43. As will be apparent to one having ordinary skill in the art, two pumps, one for each chamber, could also be employed in this system.

The enclosure 42 contains an optional heater 49 attached to a temperature controller 46 to control the temperature of the hydrogen peroxide complex. The hydrogen peroxide complex concentration in the vapor state can be monitored by an optional peroxide monitor 48. The interior of the chamber contains a radio frequency (RF) electrode 50, to which is attached a matching network 52 and an RF power supply 54. A convenient form for the electrode is a perforated cylinder, surrounding the samples and open at both end. The general operation of the present process is as follows:

1. The articles 56 to be sterilized are placed in the chamber 30.

2. The chamber 30 may be at atmospheric pressure or, alternatively, may be evacuated to facilitate penetration of the hydrogen peroxide. Evacuation is accomplished by opening valve 38 and turning on vacuum pump 36. Alternatively, both the chamber 30 and the enclosure 42 may be evacuated by opening valves 38 and 44, and/or 43.

3. The valves 38 and 43 are closed to isolate the vacuum pump 36 from the chamber 30 and enclosure 42, and the valve 44 is opened. Hydrogen peroxide vapor is delivered into chamber 30 from the hydrogen peroxide source, which may be heated to facilitate the release of the hydrogen peroxide vapor. Optionally, air or an inert gas may also be added.

4. The articles 56 to be sterilized are either treated with peroxide vapor until sterilized or pretreated with peroxide vapor in the chamber 30 before plasma with sufficient power to sterilize is generated. If necessary, chamber 30 may be evacuated at this time to facilitate generation of the plasma. The duration of the pre-plasma holding period depends on the type of package used, the nature and number of items to be sterilized, and the placement of the items in the chamber. Optimum times can be determined empirically.

5. The articles 56 are subjected to a plasma by applying power from the RF power supply 54 to the RF electrode 50. The RF energy used to generate the plasma may be pulsed or continuous. The articles 56 remain in the plasma for a period to effect complete sterilization and/or to remove residual hydrogen peroxide. In certain embodiments, 5 to 30 minutes of plasma is used. However, optimum times can be determined empirically.

When used in the present specification and claims, the term "plasma" is intended to include any portion of the gas or vapor that contains electrons, ions, free radicals, dissociated and/or excited atoms or molecules produced as a result of an applied electric field, including any accompanying radiation that might be produced. The applied field may cover a broad frequency range; however, a radio frequency or microwaves are commonly used.

The non-aqueous hydrogen peroxide delivery system disclosed in the present invention can also be used with plasmas generated by the method disclosed in the previously mentioned U.S. Pat. No. 4,643,876. Alternatively, it may be used with plasmas described in U.S. Pat. No. 5,115,166 or 5,087,418, in which the article to be sterilized is located in a chamber that is separated from the plasma source.

The device just described is particularly advantageous when using peroxide complexes that are not stable under vacuum. There are at least two possible methods that can be used to minimize the loss of hydrogen peroxide during the vacuum stage. First, the small chamber can be evacuated independently. Second, if a small enough chamber is used, there is no need to evacuate the small chamber at all.

One such unstable non-aqueous peroxide complex is glycine anhydride-peroxide. This compound releases hydrogen peroxide vapor when placed under vacuum. FIG. 4 is a graph illustrating the release of hydrogen peroxide vapor from glycine anhydride-peroxide complex under vacuum. The procedure used to release the hydrogen peroxide from the glycine anhydride complex is as follows: (1) The main chamber 30 was evacuated with valves 43 and 44 closed. (2) The chamber containing the hydrogen peroxide complex 42 was evacuated with valves 38 and 44 closed and valve 43 open. (3) Valve 43 was closed and valve 44 was opened and hydrogen peroxide vapor was allowed to diffuse into chamber 30.

As shown by the graph, hydrogen peroxide vapor is released from the complex as the pressure is reduced, even without additional heating. As illustrated in FIG. 4, release of peroxide vapor is significantly increased by heating the complex to a higher temperature. Thus, even unstable peroxide complexes are useful in the sterilization method of the present invention.

The present invention provides at least four advantages over earlier hydrogen peroxide sterilization systems:

1. The use of concentrated, potentially hazardous hydrogen peroxide solutions is circumvented.

2. The need to reduce beforehand the relative humidity of areas to be sterilized in order to prevent condensation is eliminated.

3. Water is substantially eliminated from the system, so that there is little competition between water and hydrogen peroxide for diffusion into long narrow lumens.

4. The need to attach a special vessel to deliver sterilant gases into long narrow lumens can often be eliminated.

That sterilization can be effected using hydrogen peroxide vapor in the substantial absence of moisture is one of the surprising discoveries of the present invention. The prior art teaches that the presence of water is required to achieve sterilization in chemical gas or vapor state sterilization processes. Advantageously, the present invention substantially eliminates water from the system, which results in faster, more efficient and effective sterilization.

The sterilization efficacy of various non-aqueous hydrogen peroxide complexes was determined as described below in Examples 1-4.

EXAMPLE 1

Efficacy data was obtained with hydrogen peroxide vapor released from substantially anhydrous urea peroxide complex using *Bacillus subtilis* var. (niger) spores in metal and TEFLON™ plastic lumens as the biological challenge.

A. Test Procedures
 1. Equipment

Four grams of crushed hydrogen peroxide urea adduct tablet (Fluka Chemical Corp, Ronkonkoma, N.Y.) were placed in an aluminum pan 90, as described in FIG. 3A. The top of the pan 90 was covered with medical grade TYVEK™ 92 (a breathable spunbond polyethylene fabric) so that any hydrogen peroxide released from the complex would need to pass through the TYVEK™ covering before diffusing into the rest of the chamber. The aluminum pan 90 was placed on a heating pad 94 in a pyrex dish 96 located in the bottom of an aluminum sterilization chamber (see FIG. 1). The sterilization chamber, which had an approximate volume of 173 liters, also contained:

A hydrogen peroxide monitor for measuring hydrogen peroxide concentration in the vapor phase.

A temperature controller for controlling the temperature of the heating pad.

An injection port through which liquid hydrogen peroxide could be injected into the chamber.

A metal shelf on which a plastic tray containing lumen devices were placed for testing.

Electrical resistance heaters on the exterior of the chamber walls, which maintained the chamber temperature at 45° C. during the efficacy testings.

2. Biological Challenge and Test

To evaluate the efficacy of the non-aqueous peroxide delivery system, a biological challenge consisting of 1.04× $10^6$ *B. subtilis* var. (niger) spores on a stainless steel scalpel blade was placed equally distant from each end of the stainless steel lumens of dimensions 3 mm ID×40 cm length, 3 mm ID×50 cm length, and 1 mm ID×50 cm length. These ID's and lengths are typical for metal lumens used in medical devices. The compartment in the middle of each lumen that contained the biological test piece had the dimensions 13 mm ID×7.6 cm length. In the biological testing with metal lumens, a total of 9 lumens were evaluated per test. These included 3 lumens from each of the 3 different sets of ID's and lengths available.

Similar tests were conducted with a biological challenge consisting of 4.1×$10^5$ *B. subtilis* var. (niger) spores on a paper strip (6 mm×4 mm Whatman #1 chromatography paper) located equally distant from the ends of TEFLON™ paper) lumens of dimensions 1 mm ID×1 meter length, 1 mm ID×2 meter length, 1 mm ID×3 meter length, and 1 mm ID×4 meter length. The center compartment of these lumens that contained the biological test piece had the dimensions 15 mm ID×7.6 cm length. In the biological testing with TEFLON™ lumens, a total of 12 lumens were evaluated per test, 3 lumens from each of the 4 different lengths available.

The lumens containing the biological test samples were placed in a plastic tray that was then placed on the shelf in the sterilization chamber. The chamber door was then closed and the chamber evacuated to 0.2 Torr pressure with a vacuum pump. The aluminum pan containing the hydrogen peroxide urea adduct was then heated to 80° to 81° C. for a period of 5 minutes, as measured by a thermocouple thermometer placed on the side wall of the aluminum pan approximately 1 cm from the bottom of the pan. During this time the concentration of hydrogen peroxide in the chamber increased to 6 mg/L as measured by the peroxide monitor.

The biological test samples were exposed to the hydrogen peroxide vapor for periods of 5, 10, 15, 20, and 25 minutes. After exposure to the hydrogen peroxide vapor, the biological test samples were aseptically transferred into 15 mL of trypticase soy broth containing 277 units of catalase to neutralize any hydrogen peroxide residuals that may remain on the test samples. All samples were incubated for 7 days at 32° C. and observed for growth.

Comparative studies were also conducted in which a 50% aqueous solution of hydrogen peroxide was injected into the sterilization chamber and vaporized from a heated injector (a heated metal surface). The volume of hydrogen peroxide solution injected produced a vapor phase concentration of hydrogen peroxide of 6 mg/L. The test lumens and biological test samples used in these tests were identical to those used in the non-aqueous hydrogen peroxide tests. The handling of the biological test samples after exposure to the hydrogen peroxide was also identical.

B. Test Results

The results of these tests with stainless steel and TEFLON™ lumens, which are presented in Tables 3 and 4, respectively, illustrate the advantages of the non-aqueous peroxide delivery system with both metal and non-metal lumens. Total kill of the bacterial spores was achieved within 5 minutes with the non-aqueous peroxide delivery system for the smallest ID and the longest lumens evaluated. At the same time, total kill was not achieved even after 25 minutes of diffusion time with the 50% hydrogen peroxide solution.

TABLE 3

Aqueous/Non-Aqueous Efficacy Comparison
SS Blades in SS Lumens

| SOURCE OF PEROXIDE | DIFFUSION TIME (MIN) | STERILITY RESULTS (POSITIVE/SAMPLES) | | |
|---|---|---|---|---|
| | | 3 mm × 40 cm | 3 mm × 50 cm | 1 mm × 50 cm |
| 50% SOLUTION | 5 | 3/3 | 3/3 | 3/3 |
| | 10 | 0/3 | 2/3 | 3/3 |
| | 15 | 1/3 | 1/3 | 1/3 |
| | 20 | 0/3 | 0/3 | 1/3 |
| | 25 | 0/3 | 0/3 | 1/3 |
| UREA PEROXIDE | 5 | 0/3 | 0/3 | 0/3 |
| | 10 | 0/3 | 0/3 | 0/3 |
| | 15 | 0/3 | 0/3 | 0/3 |
| | 20 | 0/3 | 0/3 | 0/3 |
| | 25 | 0/3 | 0/3 | 0/3 |

TABLE 4

Aqueous/Non-Aqueous Efficacy Comparison
6 mm × 4 mm Paper strip in TEFLON ™ Lumens

| SOURCE OF PEROXIDE | DIFFU- SION TIME (MIN) | STERILITY RESULTS (POSITIVE/SAMPLES) | | | |
|---|---|---|---|---|---|
| | | 1 mm × 1 m | 1 mm × 2 m | 1 mm × 3 m | 1 mm × 4 m |
| 50% SOLUTION | 5 | 3/3 | 3/3 | 3/3 | 3/3 |
| | 10 | 3/3 | 3/3 | 3/3 | 3/3 |
| | 15 | 0/3 | 1/3 | 1/3 | 2/3 |
| | 20 | 0/3 | 0/3 | 1/3 | 1/3 |
| | 25 | 0/3 | 0/3 | 0/3 | 1/3 |
| UREA PEROXIDE | 5 | 0/3 | 0/3 | 0/3 | 0/3 |
| | 10 | 0/3 | 0/3 | 0/3 | 0/3 |
| | 15 | 0/3 | 0/3 | 0/3 | 0/3 |
| | 20 | 0/3 | 0/3 | 0/3 | 0/3 |
| | 25 | 0/3 | 0/3 | 0/3 | 0/3 |

The fact that rapid sterilization can be accomplished in the absence of substantial amounts of water is surprising, in light of the fact that moisture has generally been present during chemical gas/vapor phase sterilization by various sterilants other than hydrogen peroxide. Since vapor phase hydrogen peroxide sterilization systems have used aqueous solutions of hydrogen peroxide, there has been moisture present in those systems as well.

To test the sterilization efficacy of various other peroxide complexes, the following experiments were performed.

EXAMPLES 2, 3 and 4

The apparatus of Example 1 was used to test the efficacy of polyvinylpyrrolidone-hydrogen peroxide complex (Example 2), nylon 6-hydrogen peroxide complex (Example 3), and 1,3 dimethylurea hydrogen peroxide complex (Example 4). These compounds were synthesized according to the method disclosed below in Examples 12 and 13. Test parameters were as follows:

| | Example | | |
|---|---|---|---|
| | 2 | 3 | 4 |
| Chamber Temp. | 45° C. | 45° C. | 45° C. |
| Initial Pressure | 0.2 Torr | 1.0 Torr | 1.0 Torr |
| Wt. % of peroxide | 17% | 10.5% | 26.6% |
| Peroxide concentration | 6 mg/L | 6 mg/L | 6 mg/L |
| Wt. of complex used per cycle | 8 g | 18 g | 6 g |
| Temp to release peroxide | 110° C. | 110° C. | 80° C. |

In each case, spore supports were 6 mm×4 mm paper substrates in plastic lumens and stainless steel blades in stainless steel lumens. The results of this efficacy testing appear below in Table 5.

TABLE 5

Efficacy of Complexes with PVP,
nylon 6, and 1,3-dimethylurea

| TYPE OF LUMEN | SIZE OF LUMENS | STERILITY RESULTS (POSITIVE/SAMPLES) With 5 Minutes Exposure | | |
|---|---|---|---|---|
| | | Example 2 | Example 3 | Example 4 |
| TEFLON ™ | 1 mm × 1 m | 0/3 | 0/3 | 0/3 |
| | 1 mm × 2 m | 0/3 | 0/3 | 0/3 |
| | 1 mm × 3 m | 0/3 | 0/3 | 0/3 |
| | 1 mm × 4 m | 0/3 | 0/3 | 0/3 |
| STAINLESS STEEL | 3 mm × 40 cm | 0/3 | 0/3 | 0/3 |
| | 3 mm × 50 cm | 0/3 | 0/3 | 0/3 |
| | 1 mm × 50 cm | 0/3 | 0/3 | 0/3 |

The results appearing in Table 5 show that each of the tested hydrogen peroxide complexes generate peroxide vapor which provides efficient sterilization after only five minutes exposure.

The temperature required to release the hydrogen peroxide vapor from the solid complex which is shown above is the temperature measured by a thermocouple thermometer located on the outside of the aluminum pan approximately 1 cm from the bottom of the pan. Further testing using a thermometer, such as a fluoroptic thermometer, placed on the inside bottom of the pan indicated that the temperature at the bottom of the pan was approximately 30°–35° C. higher, as described in Example 5 below. Thus, in the previous example, the temperature at the bottom of the pan was approximately 110°–115° C. when the thermocouple thermometer read 80° C., and the temperature at the bottom of the pan was approximately 140°–145° C. when the thermocouple thermometer read 110° C.

EXAMPLE 5

To determine the temperature at the bottom of the aluminum pan used to contain the solid peroxide complex, a fluoroptic thermometer was taped to the inside bottom of the aluminum pan. An Omega™ thermocouple thermometer was placed on the outside of the aluminum pan approximately 1 cm from the bottom of the pan. Three different readings of the thermometers were taken. Each time the pan was heated to the desired temperature indicated by the thermometer placed on the side of the pan, allowed to cool, and then re-heated to the desired temperature. The recorded temperatures are listed below:

| Temp. at side of pan | Temp. at bottom of pan (°C.) | | | |
|---|---|---|---|---|
| | 1st | 2nd | 3rd | avg |
| 80° C. | 110.9 | 110.6 | 110.6 | 110.7 |
| 100° C. | 131.5 | 132.6 | 132.0 | 132.0 |

The results show that the temperature at the bottom of the aluminum pan was approximately 30°–35° C. higher than the temperature indicated by the thermocouple thermometer located at the side of the pan.

Further testing was performed to compare the efficacy data obtained using an aqueous and non-aqueous source of peroxide in an open (non-lumen) system. The experiments are described in detail below.

EXAMPLE 6

The apparatus of Example 1 was used with a biological challenge that consisted of $6.8 \times 10^5$ B. subtilis var (niger) spores on a 6 mm×4mm strip of Whatman #1 chromatography paper packaged in a TYVEK™/MYLAR™ envelope. (TYVEK™ is a gas permeable fabric made of polyethylene. MYLAR™ is a non-gas permeable polyester material). Packaged biological challenge strips were placed in the front, middle and back of a polyphenylene oxide tray that contained a flexible fiberoptic sigmoidoscope. The tray was placed in a polyphenylene oxide container that had one port in the top and two ports in the bottom to allow for diffusion. The four-inch diameter ports were covered with a breathable polypropylene packaging material (SPUNGUARD™ Heavy Duty Sterilization Wrap, Kimberly-Clark, Dallas, Tex.) to maintain the sterility of the contents of the container after sterilization. The container was placed in the apparatus of Example 1 and the pressure in the chamber was reduced to 0.2 Torr. The aluminum pan containing 2 grams of hydrogen peroxide urea adduct (Fluka Chemical Corp.) was then heated to 80° to 81° C., as measured by a thermocouple thermometer placed on the outside of the aluminum pan approximately 1 cm from the bottom of the aluminum pan, for 5 minutes to provide 3 mg/L of hydrogen peroxide vapor in the chamber. The biological test samples were exposed to the hydrogen peroxide vapor for periods of 5 and 10 minutes. After exposure the test samples were handled in the same way as were those in Example 1.

Comparative studies were also conducted in which a 50% aqueous solution of hydrogen peroxide was injected into the sterilization chamber and vaporized from a heated injector. The volume of hydrogen peroxide solution injected produced a vapor phase concentration of 3 mg/L. The test configuration, the composition of the biological test samples, and the handling of the biological test samples after exposure were all identical to those used in the non-aqueous hydrogen peroxide tests. The results of these tests are presented in Table 6.

TABLE 6

Aqueous/Non-Aqueous Efficacy Comparison in Open System (Non-Lumen Test)

| Source of Peroxide | Diffusion Time (min) | Sterility Results (positive/samples) |
|---|---|---|
| 50% solution | 5 | 3/3 |
| | 10 | 3/3 |
| Urea Peroxide | 5 | 1/3 |
| | 10 | 0/3 |

The results of these tests demonstrate the greater efficacy of the nonaqueous when compared with the aqueous hydrogen peroxide process in an "open" system in which the biological sample was not placed in a lumen. Again, it was surprisingly discovered that a non-aqueous system provided superior sterilization even when diffusion of hydrogen peroxide into a long and narrow lumen is not required. This suggests that the mode of action of hydrogen peroxide is not the same for systems with and without water.

Further testing was performed to determine the efficacy a non-aqueous peroxide vapor at normal, not reduced, pressure. This testing is detailed below.

EXAMPLE 7

Efficacy tests were conducted with the hydrogen peroxide vapor released from the urea peroxide complex in an open system at atmospheric pressure. In this test the biological challenge of $1.04 \times 10^6$ B. subtilis var. (niger) spores on the stainless steel surgical blades were packaged in a TYVEK™/MYLAR™ envelope. Packaged biological challenge blades were placed on the front, middle, and back of a polyphenylene oxide tray. The tray was placed in the apparatus of Example 1 and the chamber door was closed. The aluminum pan containing 4.0 gm of urea peroxide (Fluka Chemical Corp.) was heated to 80° to 81° C., as measured by a thermocouple thermometer placed on the side of the aluminum pan approximately 1 cm from the bottom of the pan, for the duration of the test. The biological test samples were exposed to the hydrogen peroxide vapor for periods of 5, 10, 20 and 30 minutes. After exposure the test samples were handled the same way as those in Example 1. The results of these tests are presented in Table 7 and demonstrate the efficacy of the nonaqueous peroxide process in an open system at atmospheric pressure.

TABLE 7

Efficacy of non-aqueous peroxide process in open system at atmospheric pressure

| Source of Peroxide | Diffusion Time (minutes) | Sterility Results (positive/samples) |
|---|---|---|
| Urea Peroxide | 5 | 3/3 |
| | 10 | 1/3 |
| | 20 | 0/3 |
| | 30 | 0/3 |

Further tests were conducted to determine the approximate amount of peroxide released from the hydrogen peroxide urea complex at various temperatures. This testing is described in Example 8.

EXAMPLE 8

Urea peroxide powder, obtained from crushing the commercially available tablets (Fluka Chemical Corp.), was placed between two aluminum screens in an apparatus according to FIG. 3B having dimensions 12.7 cm×12.7 cm. The aluminum plate was then heated and the temperature was monitored using a thermometer located near a corner of the aluminum plate. Table 8 lists the approximate percent of peroxide released at various temperatures after heating for five minutes. The data show that approximately 100% of the peroxide is released from the complex at a temperature of 140° C. Lesser percentages of peroxide are released at lower temperatures.

TABLE 8

Release of non-aqueous peroxide at various temperatures

| Heating Temperature | % Peroxide Released |
|---|---|
| 80° C. | ~25% |
| 100° C. | ~65% |
| 120° C. | ~80% |
| 130° C. | ~90% |
| 140° C. | ~100% |

Peroxide complexes having the ability to release hydrogen peroxide vapor at room temperature and atmospheric pressure, such as the urea peroxide complex, allows them to be effective for use in various sterilization applications. Not only can they be used in the sterilization apparatus of the present invention described above, the compounds of the present invention can also be used as part of self-sterilizing packaging materials, or applied onto supports such as gauze, sponge, cotton, and the like. The compounds allow for sterilization of sealed packages at room temperature or at elevated temperatures, and are particularly useful for the sterilization of packaged medical or surgical products.

Particular uses of the compounds of the present invention are described in the examples which follow. The peroxide complex used in the following examples was urea peroxide in the form of a tablet (Fluka Chemical Corp.) or in the form of a powder obtained by crushing the tablets.

EXAMPLE 9

A self-sterilizing pouch was assembled as follows: A surgical scalpel having $3.8 \times 10^5$ B. subtilis var. niger spores on its surface was placed in a sterile petri dish. The dish was placed in a larger petri dish, together with 1 gm urea peroxide complex in either tablet or powder form. The larger petri dish was then inserted into a pouch formed of TYVEK™/MYLAR™ (gas permeable, Table 9), MYLAR™/MYLAR™ (non-gas permeable, Table 10) or Paper/MYLAR™ (gas permeable, Table 10). The pouch was then sealed.

Each pouch was exposed to various temperatures for various time periods, as shown in Tables 9 and 10 below. The biological test samples were evaluated for sterilization as described in Example 1. The results are included in Tables 9 and 10, with a "+" sign indicating bacterial growth.

TABLE 9

Self-Sterilizing Pouches With Breathable Barrier (TYVEK ™/MYLAR ™)

| Temperature | Peroxide Type | 1 hr. | 2 hr. | 3 hr. | 4 hr. |
|---|---|---|---|---|---|
| 23° C. | powder | + | − | − | − |
|  | tablet | + | + | − | − |
| 40° C. | powder | − | − | − | − |
|  | tablet | − | − | − | − |

TABLE 9-continued

Self-Sterilizing Pouches With Breathable Barrier (TYVEK ™/MYLAR ™)

| Temperature | Peroxide Type | 1 hr. | 2 hr. | 3 hr. | 4 hr. |
|---|---|---|---|---|---|
| 60° C. | powder | − | − | − | − |
|  | tablet | − | − | − | − |

Table 10 lists the efficacy data for self-sterilizing pouches with (Paper/MYLAR™) and without (MYLAR™/MYLAR™) a breathable barrier. The pouches were assembled as described above, however the peroxide vapor source was urea peroxide in powder form only.

TABLE 10

Self-Sterilizing Pouches With & Without Breathable Barrier

| Temperature | Packaging Type | 2 hr. | 4 hr. |
|---|---|---|---|
| 23° C. | MYLAR/MYLAR | − | − |
|  | Paper/MYLAR | + | − |
| 40° C. | MYLAR/MYLAR | − | − |
|  | Paper/MYLAR | − | − |
| 60° C. | MYLAR/MYLAR | − | − |
|  | Paper/MYLAR | − | − |

Results from this testing show that the urea peroxide complex of the present invention included in a pouch with and without a breathable barrier provides effective sterilization to an article inside the pouch in the absence of moisture at room temperature and atmospheric pressure after only 2 to 3 hours. At higher temperatures, sterilization is effected after only one hour.

To determine the efficacy of the sterilization system of the present invention in a closed container, the following experiment was performed.

EXAMPLE 10

A self-sterilizing container was assembled as follows: A stainless steel support having either $3.8 \times 10^5$ B. subtilis var. niger spores on its surface (Table 11) or having $9.2 \times 10^5$ B. subtilis var. niger spores on its surface (Table 12), was placed inside a small polyethylene (PE) vial having 20 holes (3/16" in size) in its surface. The vial was placed in a larger PE vial, which was covered with either an air tight cap, or a gas permeable layer of SPUNGUARD® (CSR Wrap). Also included in the larger vial was a second PE vial, also having 20 holes (3/16" in size) in its surface. This vial contained 1 gm urea peroxide in either powder or tablet form, and was sealed in either a SPUNGUARD™ (CSR wrap) or TYVEK™ pouch.

Each container was exposed to various temperatures for various time periods, as shown in Tables 11 and 12 below. The biological test samples were evaluated for sterilization as described in Example 1. The results are included in Tables 11 and 12, with a "+" sign indicating bacterial growth.

TABLE 11

Self-Sterilizing Containers Without Breathable Window

| Temperature | Packaging Type | 2 hr. | 6 hr. |
|---|---|---|---|
| 23° C. | Unpackaged tablet | + | − |
|  | C/C* packaged tablet | + | − |
|  | C/C packaged powder | + | − |

TABLE 11-continued

Self-Sterilizing Containers Without Breathable Window

| Temperature | Packaging Type | 2 hr. | 6 hr. |
|---|---|---|---|
| 40° C. | Unpackaged tablet | – | – |
| | C/C packaged tablet | – | – |
| | C/C packaged powder | – | – |
| 60° C. | Unpackaged tablet | – | – |
| | C/C packaged tablet | – | – |
| | C/C packaged powder | – | – |

*pouch formed from CSR wrap

TABLE 12

Self-Sterilizing Containers With Breathable CSR Window

| Temperature | Packaging Type | 0.5 hr. | 1.0 hr. | 1.5 hr. | 2.0 hr. | 3.0 hr. | 4.0 hr. |
|---|---|---|---|---|---|---|---|
| 23° C. | Unpackaged tablet | | + | + | + | – | – |
| | Unpackaged powder | | + | + | + | – | – |
| | T/T* packaged tablet | | + | + | + | + | – |
| | T/T packaged powder | | + | + | + | – | – |
| | C/C** packaged tablet | | + | + | + | – | – |
| | C/C packaged powder | | + | + | + | – | – |
| 40° C. | Unpackaged tablet | – | – | – | – | | |
| | Unpackaged powder | – | – | – | – | | |
| | T/T packaged tablet | + | – | – | – | | |
| | T/T packaged powder | – | – | – | – | | |
| | C/C packaged tablet | – | – | – | – | | |
| | C/C packaged powder | – | – | – | – | | |
| 60° C. | Unpackaged tablet | – | – | – | – | | |
| | Unpackaged powder | – | – | – | – | | |
| | T/T packaged tablet | – | – | – | – | | |
| | T/T packaged powder | – | – | – | – | | |
| | C/C packaged tablet | – | – | – | – | | |
| | C/C packaged powder | – | – | – | – | | |

*pouch formed from TYVEK ™
**pouch formed from CSR wrap

Results from this testing show that the non-aqueous urea peroxide complex included in a container with and without a breathable barrier provides effective sterilization at room temperature after only 3–4 hours. At higher temperatures, sterilization is effected after as little as one half hour.

The non-aqueous peroxide complexes which release peroxide vapor have been found to be useful in the sterilization of articles at room temperature, and more effectively, at higher temperatures. These complexes can be placed in a pouch, container, chamber, room or any area capable of being sealed, where they release peroxide vapor which effectively sterilizes the articles. The complexes can be heated to facilitate the release of vapor, and to provide sterilization in less time than that required for room temperature sterilization. The compounds of the present invention are therefore useful in a variety of applications where sterilization is desired. Simply by placing the complex in a sealed area containing an article or articles to be sterilized, sterilization can be achieved. By contrast with prior art methods, there is no need for contact with moisture to provide activation of the hydrogen peroxide.

To confirm that sterilization can be effected using non-aqueous peroxide complexes in less time at lower pressures, the following experiment was performed.

EXAMPLE 11

A self-sterilizing container was assembled as follows: A stainless steel support having $9.2 \times 10^5$ B. subtilis var. niger spores on its surface was placed inside a small PE vial having 20 holes (3/16" in size) in its surface. The vial was placed in a larger PE vial, which was covered with a gas permeable layer of CSR wrap (SPUNGUARD™). Also included in the larger vial was a second PE vial, also having 20 holes (3/16" in size) in its surface. This vial contained 1 gm urea peroxide in either powder or tablet form. The vial was then sealed in a CSR wrap or TYVEK™ pouch.

The large vials were placed in either a 4.5 L sterilization chamber or a 173 L sterilization chamber. Each container was exposed to 100 torr pressure and 23° C. temperature for 2 hours, as shown in Table 13. The biological test samples were evaluated for sterilization as described in Example 1. The results are included in Table 13.

TABLE 13

Self-Sterilizing Containers With Breathable Window In Reduced Pressure Conditions

| Temperature | Packaging Type | 4.5 L chamber | 173 L chamber |
|---|---|---|---|
| 23° C. | Unpackaged powder | – | – |
| | T/T packaged powder | – | – |
| | C/C packaged powder | – | – |

These results show that non-aqueous urea peroxide complex included in a container with a breathable barrier provides effective sterilization at 100 torr and room temperature after only 2 hours. These results, when compared with the results in Table 12, demonstrate that the peroxide complexes of the present invention provide sterilization at reduced pressures in less time than that required to effect sterilization at atmospheric pressure.

Thus, the hydrogen peroxide complexes of the present invention can provide effective sterilization in significantly shorter periods of time. In addition, as discussed above, plasma can also be used to enhance the sterilization activity of the hydrogen peroxide vapor. The articles to be sterilized are subjected to a plasma after exposure to the peroxide vapor, and remain in the plasma for a period of time sufficient to effect complete sterilization.

Articles that have been sterilized by exposure to hydrogen peroxide vapor can be exposed to a plasma to remove any residual hydrogen peroxide remaining on the articles. Because the residual hydrogen peroxide is decomposed into non-toxic products during the plasma treatment, the sterilized articles are ready for use following treatment, without the need for any additional steps.

Non-aqueous peroxide complexes are useful in a variety of applications, including as a component of self-sterilizing packaging. In addition, the complexes are suitable for use in various methods for vapor sterilization of articles, such as the method disclosed in U.S. Pat. No. 4,943,414. This patent discloses a process in which a vessel containing a small amount of a vaporizable liquid sterilant solution is attached to a lumen, and the sterilant vaporizes and flows directly into the lumen of the article as the pressure is reduced during the sterilization cycle. The method disclosed in the patent can be modified to allow for use of a non-aqueous peroxide compound. The compound is placed in a vessel and connected to the lumen of the article to be sterilized. The article is then placed within a container and the container evacuated. The lumen of the article and the exterior of the article are contacted by the hydrogen peroxide vapor released from the non-aqueous compound. A plasma can optionally be generated and used to enhance sterilization and/or to remove any residual hydrogen peroxide form the article.

Use of non-aqueous peroxide complexes in the system just described overcomes the disadvantage that the water in the aqueous solution is vaporized faster and precedes the hydrogen peroxide vapor into the lumen. Thus, more effective sterilization is achieved and less time is required to effect sterilization. Hydrogen peroxide complexes such as glycine anhydride are especially advantageous since they release a significant amount of hydrogen peroxide at reduced pressure without the need for additional heating of the complex.

Synthesis of Non-Aqueous Hydrogen Peroxide Complexes

The present invention further provides a process for preparing nonaqueous hydrogen peroxide complexes that are useful as the source in a hydrogen peroxide vapor sterilizer, or as a component of self-sterilizing packaging, as was described above. Of course, the hydrogen peroxide complexes can be used for other applications, such as for bleaching agents, contact lens solutions, catalysts, and other applications which will be well known by those having ordinary skill in the art.

The general procedure for preparing the hydrogen peroxide complexes of this invention is as follows:

(1) Place the reactant material in the chamber.

The material to be reacted with the hydrogen peroxide can be a solid in various forms, (e.g., powder, crystal, film etc., preferably having high surface area to increase the reaction rate). The reactant material can also be present as a solution in water or another solvent, if sufficient time is allowed to evaporate the solvent after the pressure is reduced in the chamber. The material may also be a liquid whose boiling point is higher than that of hydrogen peroxide (150° C.). Since reaction rates are faster at elevated temperature, the chamber is preferably heated whether before or after the reactant composition is introduced. However, the temperature should not be so high that the reactant boils or vaporizes.

The reactant composition may be contained in any container that provides access to the peroxide vapor. If it is in the form of a powder or other form that may be blown about when the chamber is evacuated, then the reactant may be retained in a permeable container, which allows hydrogen peroxide to diffuse into the container.

(2) Evacuate the chamber.

In certain embodiments, the chamber is evacuated to a pressure below atmospheric pressure, such as a pressure that is below the vapor pressure of the hydrogen peroxide (which depends on its concentration and temperature), in order to assure that all of the peroxide is in the vapor phase. The vapor pressure increases with increasing temperature and decreases with increasing peroxide concentration. For most of the experiments, the chamber was evacuated to about 0.2 Torr and the temperature was ambient or above.

(3) Generate hydrogen peroxide vapor.

The hydrogen peroxide vapor can be generated from a hydrogen peroxide solution or from a substantially anhydrous hydrogen peroxide complex. The latter yields dry hydrogen peroxide in the vapor state, which is an advantage if either the material to be reacted with the vapor or the complex to be formed is hygroscopic. Another advantage of generating the hydrogen peroxide vapor from a substantially water-free complex is that the percent of hydrogen peroxide in the complex being formed is higher than if the vapor is generated from an aqueous solution of $H_2O_2$. This is probably due to the competition between water molecules and $H_2O_2$ molecules for bonding sites on the complex when an aqueous solution is used to generate the $H_2O_2$ vapor.

The peroxide vapor can be generated within the same chamber that houses the reactant material or in another chamber separated from it by a vacuum valve.

(4) React the reactant material with hydrogen peroxide.

The time required for the reaction depends, of course, on the reaction rate of the reactant with hydrogen peroxide. It can be empirically determined by monitoring the pressure, which decreases during the binding of peroxide to the reactant material. Typically, the reaction time is about 5–30 minutes. The concentration of vaporized hydrogen peroxide and the weight of the starting material determine the weight percentage of peroxide in the final reaction product. As the weight ratio of reactant to hydrogen peroxide increases, the weight percentage of hydrogen peroxide in the complex decreases. The reaction can be repeated multiple times to increase the concentration of hydrogen peroxide in the complex.

(5) Evacuate the chamber again.

At the end of the reaction period, the chamber is further evacuated to about 2 Torr to remove any unreacted hydrogen peroxide.

(6) Vent the chamber and retrieve the hydrogen peroxide complex.

The mechanism by which the hydrogen peroxide forms a complex with the reactant material is not completely understood. The formation of the complex is believed to involve hydrogen bond formation between the hydrogen peroxide and electron-rich functional groups containing oxygen and/or nitrogen on the reactant material. It is not known if this is the only mode of binding; however, materials with a wide range of functional groups have been found to form complexes with hydrogen peroxide.

The advantages of the vapor phase reaction over earlier methods of hydrogen peroxide complex formation include:

1. The ratio of hydrogen peroxide to reactant material can be accurately controlled by varying the amount of hydrogen peroxide present in the vapor state or the amount of reactant material exposed to the vapor.

2. The need to remove solvent from the reaction product is eliminated.

3. Peroxide complexes can be formed that are liquid or solids, such as powders, crystals, films, etc.

4. Peroxide complexes of hygroscopic materials can be prepared.

The synthesis of the non-aqueous peroxide complexes according to the present invention is further described in the following examples. Many of these compounds have utility as catalysts, in addition to having the utilities described in greater detail herein, as will be readily appreciated by those having ordinary skill in the art. The examples represent embodiments of the compositions and processes of the invention, but they are not in any way intended to limit the scope of the invention.

EXAMPLE 12

A hydrogen peroxide complex of glycine anhydride was prepared as follows: A 1.0 gram sample of glycine anhydride (Aldrich Chemical Co., Milwaukee, Wis.) was placed in an aluminum tray in a 173 liter chamber maintained at a temperature of 45° C. The top of the aluminum tray was covered with TYVEK™ nonwoven fabric, which prevented the glycine anhydride from coming out of the tray when the pressure in the chamber was reduced but was breathable and did not absorb hydrogen peroxide. The chamber door was closed and the pressure in the chamber was reduced to 0.2 Torr by evacuating the chamber with a vacuum pump. A hydrogen peroxide concentration of 10 mg/liter was created by evaporation of an appropriate volume of a 70% aqueous solution of hydrogen peroxide (FMC Corp., Philadelphia, Pa.) into the chamber. The hydrogen peroxide vapor was maintained in contact with the glycine anhydride for 20 minutes. At the end of the reaction period, the chamber pressure was reduced to 2 Torr and then returned to atmospheric pressure. The reaction product was removed from the chamber and analyzed for weight percent hydrogen peroxide by the following iodometric titration reactions.

$$H_2O_2 + 2\ KI + H_2SO_4 \rightarrow I_2 + K_2SO_4 + 2\ H_2O$$

$$I_2 + 2\ Na_2S_2O_3 \rightarrow Na_2S_4O_6 + 2\ NaI$$

A starch indicator was used in the iodine-sodium thiosulfate titration reaction to enhance the color change at the end point. The percentage by weight of hydrogen peroxide was calculated by the following equation:

wt % $H_2O_2$ = [(ml of $Na_2S_2O_3$)*(normality of $Na_2S_2O_3$)*1.7]/(sample weight in grams)

The weight percentage of hydrogen peroxide in the glycine anhydride complex was found to be 24.3%.

EXAMPLE 13

The hydrogen peroxide complexes of a wide variety of organic and inorganic complexes were prepared using the procedure of Example 12. In each case, the reaction conditions were the same as those in Example 12, except 1.0 gram of each one of the compounds presented in Table 14 was used in place of glycine anhydride.

TABLE 14

COMPOUNDS EVALUATED AND WEIGHT PERCENT HYDROGEN PEROXIDE PRESENT IN COMPLEXES FORMED BY VAPOR PHASE SYNTHESIS PROCESS

| Chemical Name | Chemical Structure | Wt % After Peroxide Treatment | Category |
|---|---|---|---|
| Poly(vinyl alcohol) | $[-CH_2CH(OH)-]_n$ | 18.9% | Alcohol |
| Poly(vinyl methyl ether) | $[-CH_2CH(OCH_3)-]_n$ | 22.0% | Ether |
| Poly(vinyl methyl Ketone) | $[-CH_2-CH(COCH_3)-]_n$ | 13.9% | Ketone |
| Poly(acrylic acid) | $[-CH_2CH(COOH)-]_n$ | 5.1% | Acid |
| Glycine | $H_2C(NH_2)(COOH)$ | 20.7% | Amino Acid |
| L-Histidine | [N=CHNHCH=C]$CH_2CH(NH_2)COOH$ | 14.1% | Amino Acid |
| Poly(vinyl acetate) | $[-CH_2CH(OCOCH_3)-]_n$ | 9.1% | Ester |
| Cellulose acetate |  | 10.9% | Ester |
| Sodium alginate |  | 27.7% | Organic Salt |
| Cellulose sulfate, sodium salt |  | 18.2% | Organic Salt |
| Poly(4-Vinylpyridine) | $[-CH_2CH(p-C_5H_4N)-]_n$ | 21.8% | Aromatic amine |
| Histamine | [N=CHNHCH=C—]$CH_2CH_2(NH_2)$ | 13.2% | Amine |
| Propionamide | $(C_2H_5)CONH_2$ | 31.8% | Amide |
| Urea | $(H_2N)_2CO$ | 17.9% | Urea |
| 1,3-dimethylurea | $(H_3C)HNCONH(CH_3)$ | 31.7% | Urea |
| Biuret | $(H_2N)CO(NH)CO(NH_2)$ | 13.7% | Biuret |
| Polyacrylamide | $[-CH_2CH(CONH_2)-]_n$ | 30.1% | Polyamide |
| Polyvinylpyrrolidone | $[-CH_2CH(-N(CH_2)_3CO)-]_n$ | 29.9% | Polyamide |
| Nylon 6 | $[-NH(CH_2)_5CO-]_n$ | 17.1% | Polyamide |
| Nylon 6,6 film | $[-NH(CH_2)_6NHCO(CH_2)_4CO-]_n$ | 16.6% | Polyamide |
| Polyetherpolyurethane | $[-RHNCOOR'-]_n$ | 9.5% | Polyurethane |
| Sodium carbonate | $Na_2CO_3$ | 14.3% | Inorganic |
| Potassium carbonate | $K_2CO_3$ | 33.9% | Inorganic |
| Rubidium carbonate | $Rb_2CO_3$ | 37.0% | Inorganic |
| Calcium hydroxide | $Ca(OH)_2$ | 23.4% | Inorganic |

TABLE 14-continued

COMPOUNDS EVALUATED AND WEIGHT PERCENT HYDROGEN PEROXIDE PRESENT IN COMPLEXES FORMED BY VAPOR PHASE SYNTHESIS PROCESS

| Chemical Name | Chemical Structure | Wt % After Peroxide Treatment | Category |
|---|---|---|---|
| Sodium bicarbonate | $NaHCO_3$ | 10.7% | Inorganic |
| Tetrasodium pyrophosphate | $Na_4P_2O_7$ | 18.9% | Inorganic |

The organic complexes formed cover the following range of functional groups that are capable of forming hydrogen bonds with hydrogen peroxide: alcohols, ethers, ketones, acids, amino acids, esters, organic salts, amines, amides, polyamides, polyurethanes, ureas, and biuret. The inorganic complexes include carbonates with sodium, potassium, and rubidium cations, as well as sodium bicarbonate. In addition, the hydrogen peroxide complexes of calcium hydroxide and tetrasodium pyrophosphate were also prepared. The starting materials were finely divided powers or slightly larger crystalline materials, except for nylon 6,6, which was processed as a film with a thickness of 0.12 mm, and polyvinyl methyl ether, which was a 50% by weight aqueous solution.

The hydrogen peroxide complexes obtained with these materials under the test conditions were solids, except for polyvinylpyrrolidone, histamine, poly(vinyl methyl ether), poly(vinyl methyl ketone),propionamide, and 1,3-dimethylurea. The 1,3-dimethylurea and propionamide hydrogen peroxide complexes were free flowing liquids that were easily handled in the vapor phase synthesis process, since no solvent needed to be removed to obtain the final product. The histamine, polyvinylpyrrolidone, poly(vinyl methyl ether), and poly(vinyl methyl ketone) complexes were gummy materials that were not as easy to handle.

Examples 14 and 15 describe additional studies with polyvinylpyrrolidone under different process conditions to obtain the peroxide complex as a free flowing solid product.

EXAMPLE 14

Hydrogen peroxide complexes with polyvinylpyrrolidone were prepared in which the percent hydrogen peroxide in the polyvinylpyrrolidone complex was varied by changing the ratio of the weight of polyvinylpyrrolidone to the concentration of hydrogen peroxide in the vapor state. The conditions in these tests were identical to those in Example 12, except the weight of polyvinylpyrrolidone was increased from 1.0 gram to 3.0 grams to 5.0 grams. In all tests, the concentration of hydrogen peroxide was held constant at 10.0 mg/liter of chamber volume. The results of these tests are presented in Table 15.

EXAMPLE 15

A hydrogen peroxide complex of PVP was prepared in which the hydrogen peroxide was delivered from a complex of hydrogen peroxide with urea. When hydrogen peroxide is delivered in this manner, it is substantially water free. In this test, 5 grams of PVP was placed in the reaction chamber and 10 mg $H_2O_2$/liter of chamber volume was delivered into the reaction chamber by heating about 7 grams of a 35% complex of $H_2O_2$ with urea to a temperature of about 110° C. for approximately 5 minutes. The rest of the conditions in this test were the same as those in Example 12. The percentage hydrogen peroxide in the PVP complex and the physical state of the complex are presented in Table 15.

TABLE 15

EFFECT OF RATIO OF POLYVINYLPYRROLIDONE TO HYDROGEN PEROXIDE IN THE VAPOR STATE ON % HYDROGEN PEROXIDE IN COMPLEX AND PHYSICAL STATE OF PRODUCT

| | Weight PVP (g) | Wt % $H_2O_2$ in Complex | Physical State of Product |
|---|---|---|---|
| Ex. 14 | 1 | 29.9 | Soft gummy product |
| | 3 | 23.5 | Hard gummy product |
| | 5 | 17.7 | Free flowing solid |
| Ex. 15 | 5 | 19.7 | Free flowing solid |

The results of these tests demonstrate that a free flowing solid can be obtained with the PVP hydrogen peroxide complex by controlling the ratio of PVP to hydrogen peroxide in the vapor state and, alternatively, by using a substantially water-free hydrogen peroxide vapor source.

INORGANIC HYDROGEN PEROXIDE COMPLEXES

Inorganic hydrogen peroxide complexes are also suitable for use as sterilants as described in detail hereinabove for organic hydrogen peroxide complexes. Peroxide vapor can be released from these inorganic complexes at atmospheric pressure and room temperature. However, as described in greater detail below, substantial amounts of hydrogen peroxide vapor can be released from inorganic peroxide complexes upon rapid heating to a particular release temperature under both atmospheric and reduced pressure. In order to effectively release hydrogen peroxide from inorganic peroxide, the heating rate of the inorganic peroxide complexes is preferably at least 5° C./min; more preferably it is at least 10° C. per minute; still more preferably at least 50° C./min.; and most preferably, it is at least 1000° C. per minute.

A representative listing of these inorganic peroxide complexes, and the weight percent hydrogen peroxide, is presented in Table 16. Preferred inorganic complexes are those which do not decompose to form a hydrohalic acid. Thus, especially preferred complexes contain no halogens. It is also possible to provide a mixture of peroxide complexes as a source of peroxide vapor. Such a mixture can be a "physical mixture" in which two different pre-prepared peroxide complexes are physically mixed, or a "chemical mixture" in which the compounds in the complex are mixed prior to preparation of peroxide complexes therefrom.

The titration procedure used to determine the weight percent of $H_2O_2$ in the complexes was as described in Example 12. Sodium carbonate $H_2O_2$ complex was purchased from Fluka Chemical Corp. The vapor-phase synthesis procedure used for synthesizing the inorganic peroxide complexes was the same as that disclosed in Example 12, with the exceptions that 10 g of the solid inorganic sample instead of 1–5 g, and two reaction cycles versus one, were employed.

EXAMPLE 16

The reaction procedure for liquid-phase synthesis of inorganic hydrogen peroxide complexes was essentially as described by Jones et al. (*J. Chem. Soc., Dalton,* 12:2526–2532, 1980). Briefly, inorganic solids were first dissolved in a 30% aqueous solution of hydrogen peroxide to make a saturated solution, followed by dropwise addition of ethanol. For the potassium oxalate and rubidium carbonate complexes, the white peroxide precipitates were formed as the amount of ethanol added was gradually increased. For potassium carbonate, potassium pyrophosphate and sodium pyrophosphate, the saturated solutions were incubated at −10° C. for several hours to facilitate crystalline peroxide complex formation. The complexes were separated from the liquid by vacuum filtration, washed with ethanol at least three times and dried by vacuum.

TABLE 16

COMPOUNDS EVALUATED AND WEIGHT PERCENT HYDROGEN PEROXIDE PRESENT IN COMPLEXES

| Chemical Name | Chemical Formula | Wt % $H_2O_2$ in Complexes[1] | | |
|---|---|---|---|---|
| | | Purchased[2] | Vapor[3] | Liquid[3] |
| Sodium Carbonate | $Na_2CO_3$ | 27.35 | | |
| Potassium Carbonate | $K_2CO_3$ | | 7.43 | 22.70 |
| Robidium Carbonate | $Rb_2CO_3$ | | 20.31 | 26.78 |
| Potassium Oxalate | $K_2C_2O_4$ | | 16.13 | 16.42 |
| Sodium Pyrophosphate | $Na_4P_2O_7$ | | 11.48 | 23.49 |
| Potassium Pyrophosphate | $K_4P_2O_7$ | | 20.90 | 32.76 |
| Sodium Orthophosphate | $Na_3PO_4$ | | 15.67 | |
| Potassium Orthophosphate | $K_3PO_4$ | | 16.11 | |

[1]The titration procedure employed to determine the weight percent of $H_2O_2$ in the complexes is the same as the one stated herein above.
[2]Sodium carbonate hydrogen peroxide complex was purchased from Fluka Chemical Corp.
[3]The vapor and liquid phase procedures were used for synthesizing the inorganic peroxide.

Figure 5:
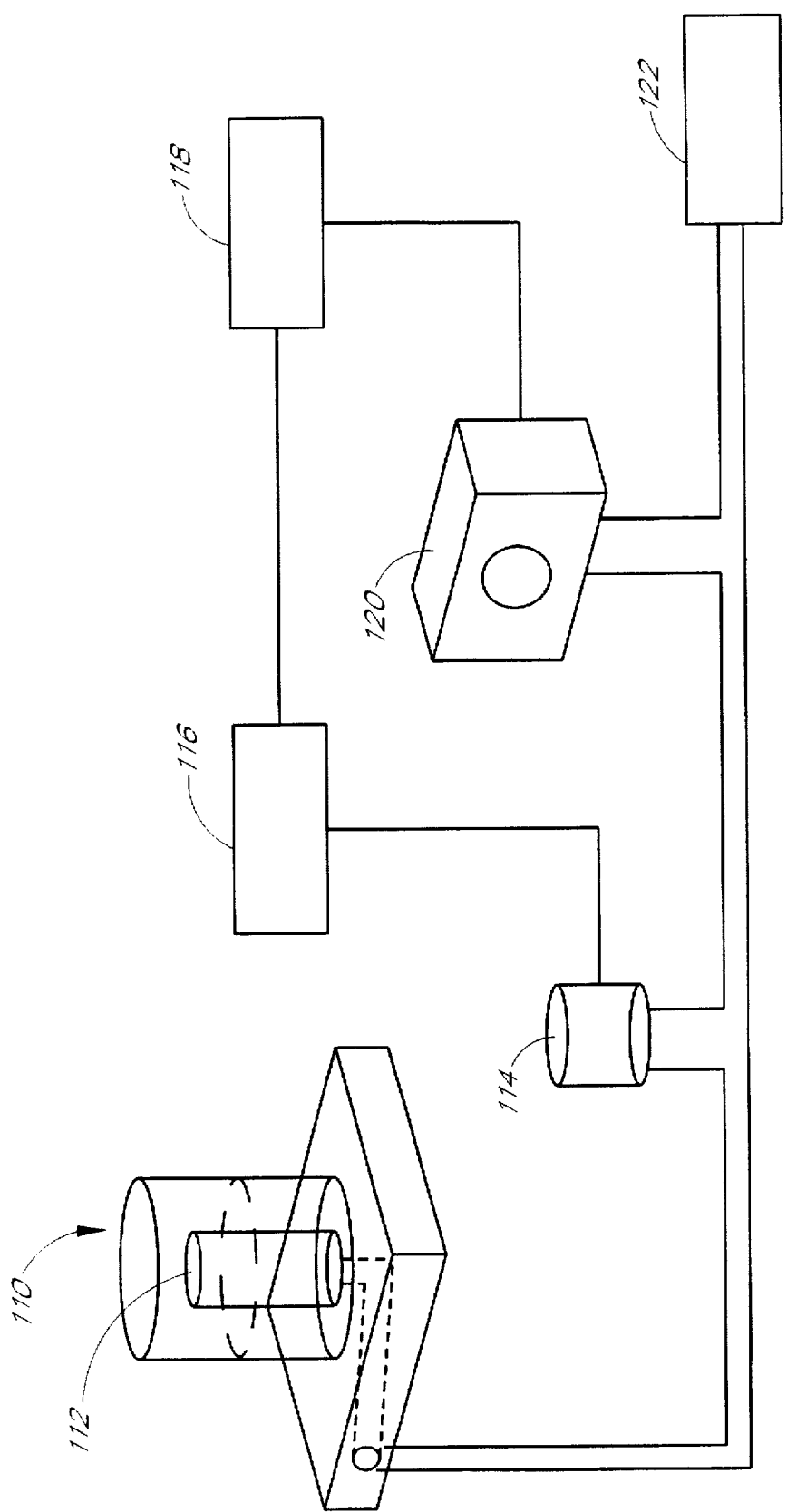
FIG. 5 is a schematic of a pressure control system of a differential scanning calorimeter (DSC) used to determine hydrogen peroxide release or decomposition properties of inorganic peroxide complexes according to the present invention.

A differential scanning calorimeter (DSC) (Model PDSC 2920, TA and Metiler-Toledo Model DSC 27HP instruments) was used to determine $H_2O_2$ release or decomposition properties of the inorganic peroxide complexes. The DSC was run at a heating ramp of 10° C./min and at a temperature range of between 30° C. and 220° C. under both atmospheric and varying vacuum pressure conditions. Referring now to FIG. 5, the DSC comprises a sample chamber 110, heating plate 112 and pressure control system. The pressure control system comprises a pressure transducer 114 connected to a pressure gauge 116. The pressure gauge 116 is connected to a controller 118 which is, in turn, connected to a pressure control valve 120. The pressure transducer 114 is in fluid communication with pressure control valve 120 and with pump 122.

Figure 6:
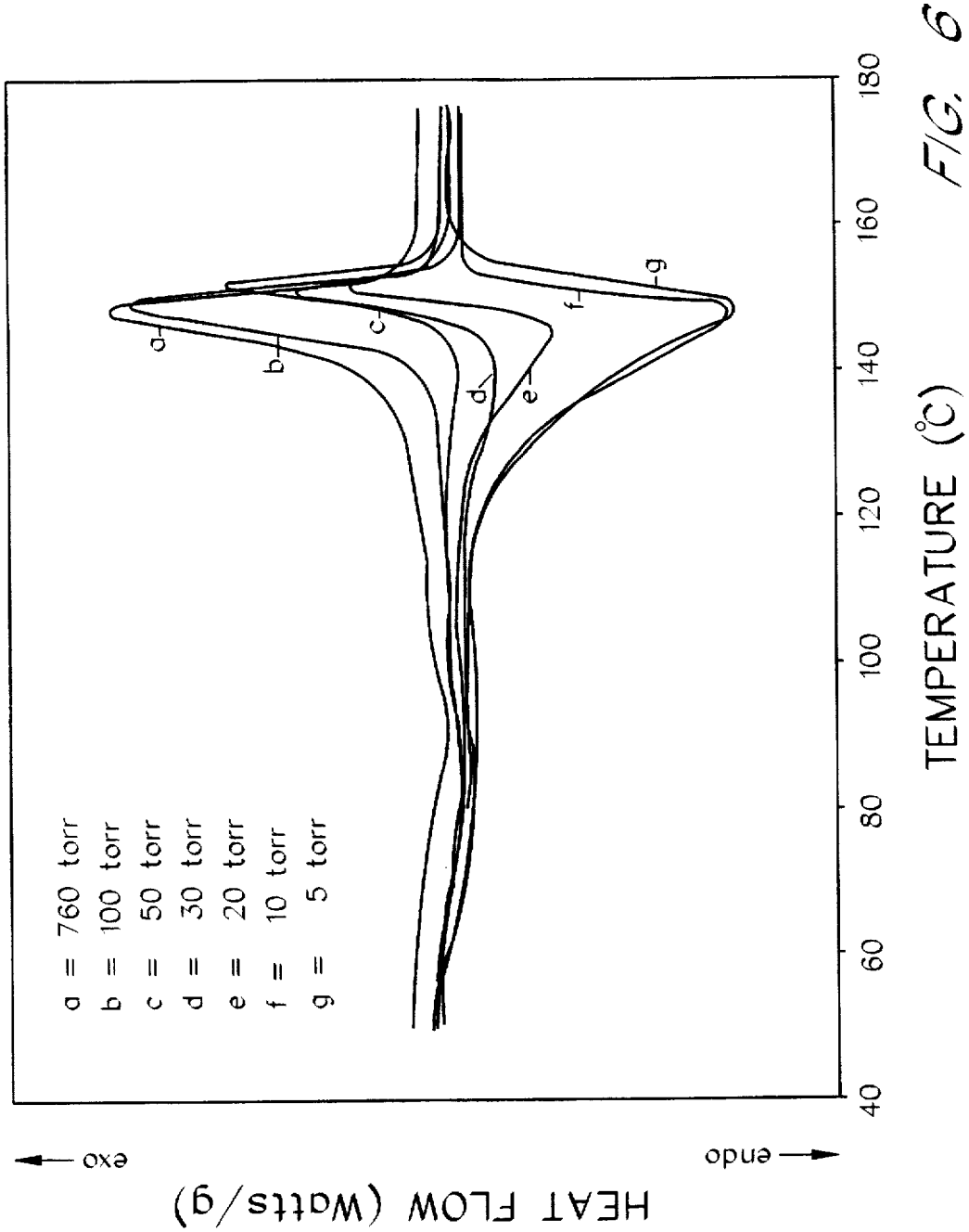
FIG. 6 is a graph showing the effect of pressure on hydrogen peroxide release from potassium oxalate peroxide complex with one small hole on a lid covering the complex.

Potassium oxalate hydrogen peroxide complex synthesized as described hereinabove was placed in a DSC and subjected to a particular vacuum pressure over a temperature range of 50° C. to 170° C. As can be seen in FIG. 6, under these DSC conditions with one hole on the lid of the sample pan, greater release of $H_2O_2$, an endothermic process, occurred at lower pressures, while the exothermic decomposition of $H_2O_2$ was favored at higher pressures. However, as shown in FIG. 10, partial release of peroxide may also occur at atmospheric pressure when the same experiment was repeated without any cover on the pan (i.e. open pan). Thus, for certain hydrogen peroxide complexes, a more open system and/or reduced pressure can facilitate release of $H_2O_2$ from the complex.

In the use of the inorganic peroxide complexes for sterilization, it is critical to complex stability that heating occur rapidly which may be effected by preheating the aluminum plate prior to contacting with the inorganic peroxide composition. In the use of the inorganic peroxide compounds, it is also preferred that the temperature be higher than 86° C.

Figure 7A:
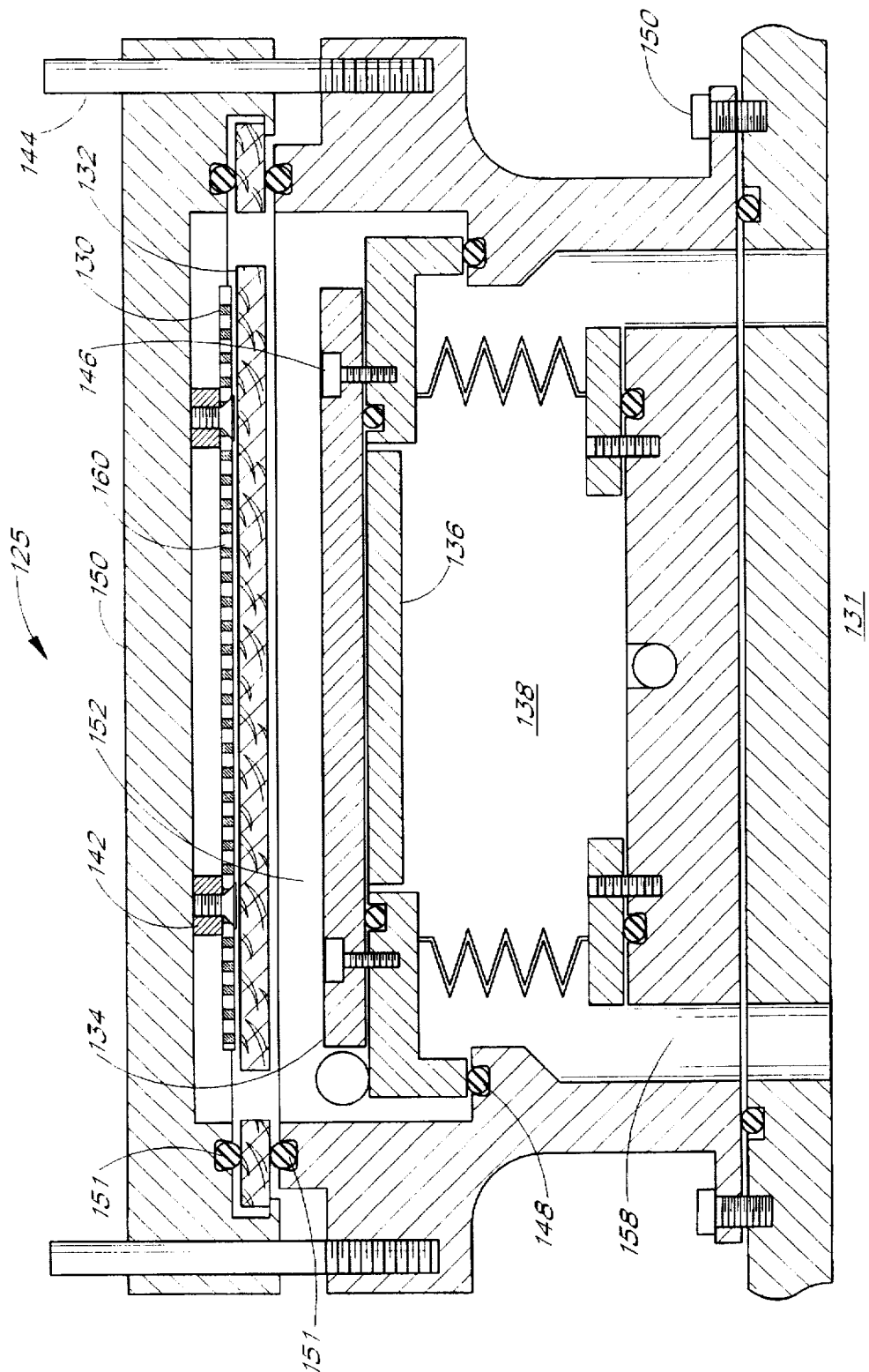
FIG. 7A is a schematic view of a bellows for introducing peroxide vapor into a chamber in accordance with the present invention before introduction of the peroxide vapor.
Figure 7B:
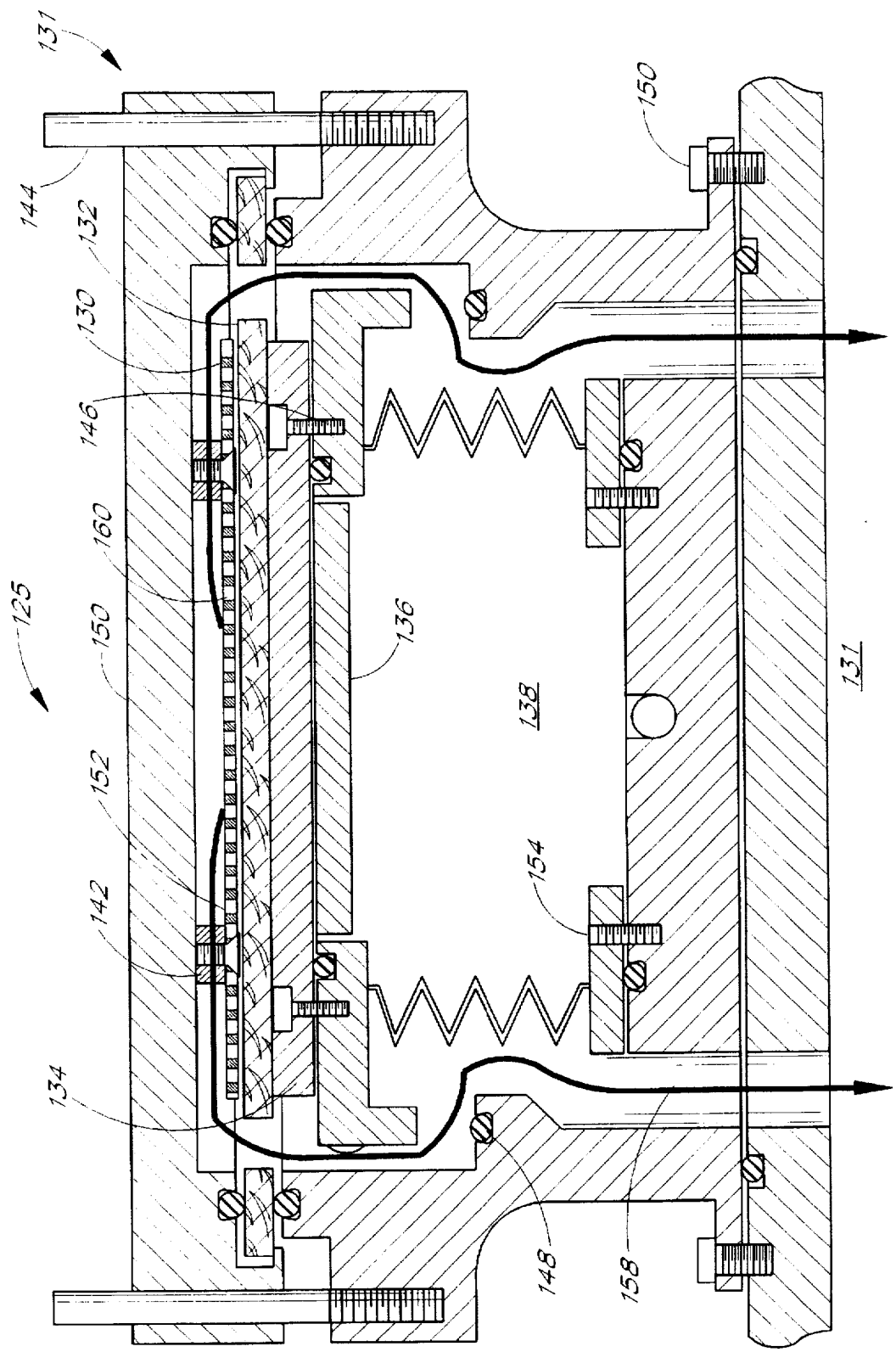
FIG. 7B is a schematic view of the bellows of FIG. 7A showing a heated plate in contact with a peroxide complex during introduction.

As discussed above, it is preferred that the inorganic hydrogen peroxide complex be heated rapidly, i.e. as rapidly as 1000° C./minute or more. This can be accomplished by contacting the peroxide with a pre-heated heating plate. A preferred embodiment for accomplishing such rapid heating is shown in FIGS. 7A and 7B. Referring to FIG. 7A, there is shown an apparatus 125 for injecting peroxide vapor into a sterilization chamber 131 in a closed position. The inorganic hydrogen peroxide complex is incorporated into a peroxide disk 132. The disk 132 comprises five layers: three layers of CSR wrap, peroxide complex powder and aluminum foil coated with polypropylene. The disk 132 is heat sealed around its edge to retain the peroxide complex powder. The peroxide disk 132 is placed underneath a perforated aluminum plate 130 which is attached to housing 150 by aluminum attachment pieces 142. The disk 132 is loosely held in place between O-rings 151. Prior to introduction of peroxide vapor into the chamber, a heated aluminum platen 134 is apart from the peroxide disk 132 and is attached to an aluminum plate 136. A spring (not shown) within the bellow 138 holds the plate 136 down in the closed position. When the chamber 131 is evacuated, the bellow 138 is also evacuated. The plate 136 is seated against O-rings 148, thus separating a peroxide release chamber 152 from passageways 158. The apparatus is held in place and attached to a sterilization chamber 131 by bolts 144, 146, 154 and 156.

Referring to FIG. 7B, in order to bring the platen 134 up to contact the peroxide disk 132, the bellow 138 is vented. Once the pressure is increased, the bellow 138 moves upward, thereby propeling the heated aluminum platen 134 against the peroxide disk 132. In a preferred embodiment, the aluminum platen 134 is pre-heated to 175° C.; however other temperatures can be used. Peroxide vapor is then released from the powder through the CSR layers, passes through the perforations 160 in the perforated aluminum plate 130, and enters the peroxide release chamber 152. The upward movement of the heated aluminum platen 134 also opens the peroxide release chamber 152, allowing peroxide vapor to enter passageways 158 which are in fluid communication with the sterilization chamber.

Figure 8:
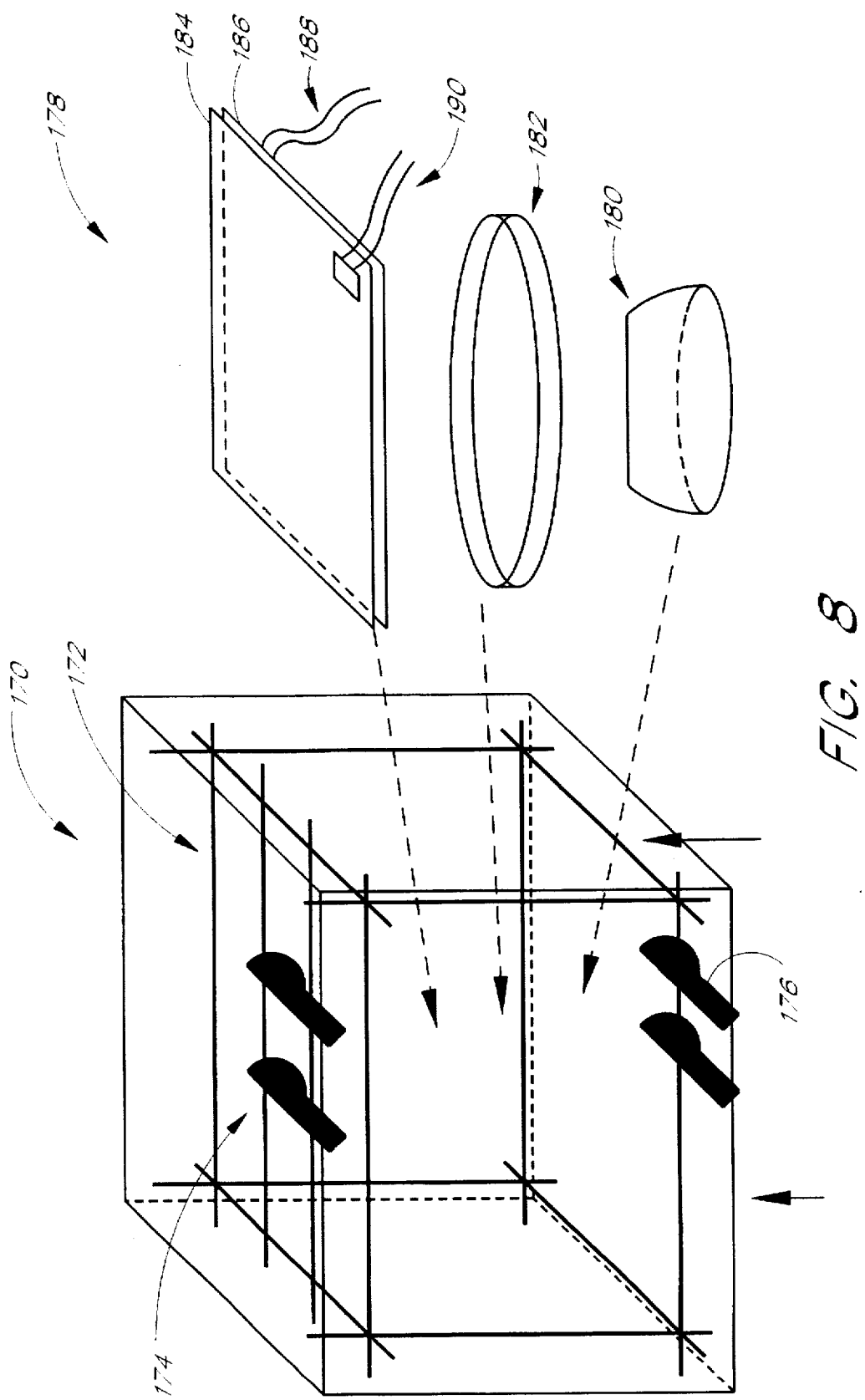
FIG. 8 is a schematic view of a sterilization chamber and heating appratus for inorganic hydrogen peroxide complexes.

Referring now to FIG. 8, there is illustrated a sterilization chamber 170 containing a plurality of glass rods 172 orthogonally arranged therein. Stainless steel scalpel blades 174 and 176 placed at the top and bottom, respectively, of chamber 170 contain *Bacillus stearothermophilus* inoculated thereon. Contained within the sterilization chamber 170 and shown to the right thereof is an apparatus 178 used for heating the hydrogen peroxide complexes, which for exemplary purposes were sodium pyrophosphate ($Na_4P_2O_7.3\ H_2O_2$) and potassium oxalate ($K_2C_2O_4.H_2O_2$) hydrogen peroxide complexes. An apparatus 178 comprises a pyrex bowl 180 at the bottom of chamber 170. A pyrex dish 182 is disposed on top of the pyrex bowl 180. An aluminum plate 184 with a heating pad 186 is placed on top of the pyrex dish 182. The peroxide complex is placed on the aluminum plate 184. A power cord 188 is attached to the heating pad 186 and a thermocouple 190 is attached to the aluminum plate 184. Scalpel blades 174 are placed two inches above the aluminum plate 184.

In certain embodiments, the hydrogen peroxide complexes are provided within a separate enclosure in fluid communication with the container in which the article to be sterilized is located. The pressures within the enclosure and the container can be the same or different. A positive pressure difference in the enclosure will facilitate movement of the peroxide vapor released from the peroxide complex within the enclosure into the container. Such positive pressure would be particularly useful where the container is large, such as when it is an entire room.

In another preferred embodiment, the peroxide complex in powder form is applied to an adhesive surface. Preferred adhesive surfaces include high temperature rated adhesive tapes such as A10 and A25 adhesive tapes (3M Corp., Minneapolis, Min.). These peroxide complex powder-coated adhesive tapes are then heated to effect peroxide release therefrom using the apparatus shown in, for example, FIGS. 3A, 7A and 8.

Figure 9:
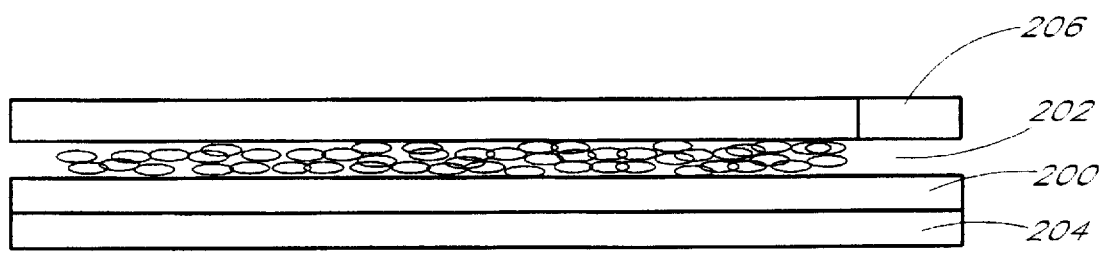
FIG. 9 is a schematic view of a diffuse packaged layer of hydrogen peroxide complex for use in vapor sterilization.

Referring to FIG. 9, high temperature rated adhesive tape 200 having peroxide complex powder 202 is disposed on aluminum foil layer 204. One or more CSR layers 206 is layered on top of adhesive tape layer 200. This arrangement can take the form of individual sheets of material, or a roll can be formed from the material.

The inorganic peroxide complexes used in Examples 17 and 18 to determine the amount of peroxide release and sterilization efficacy were potassium pyrophosphate ($K_4P_2O_7 \cdot 3\ H_2O_2$: PP), potassium oxalate ($K_2C_2O_4 \cdot 1\ H_2O_2$: PO) and sodium carbonate ($Na_2CO_3 \cdot 1.5\ H_2O_2$: SC).

EXAMPLE 17

Release of Peroxide from SC, PO and PP

The ideal temperature at which $H_2O_2$ was released from SC, PO and PP was determined by DSC. The actual amount of $H_2O_2$ released from 2 g of each of these complexes was determined at various temperatures using a 75 liter chamber and the apparatus shown in FIGS. 7A and 7B. The amount of $H_2O_2$ released from PP at 175° C. was greater than for SC and PO. Although SC released the least amount of $H_2O_2$ at 175° C., significantly more release was seen when the amount of sample was increased.

TABLE 17

RELEASE OF PEROXIDE IN 75 LITER CHAMBER

|  | SC | PO | PP |
|---|---|---|---|
| Temp. to release $H_2O_2$ |  |  |  |
| (by DSC) | 170° C. | 150° C. | 130° C. |
| With 2 grams sample |  |  |  |
| At 125° C. | 0.3 mg/L | 0.8 mg/L | 1.0 mg/L |
| At 150° C. | 1.2 mg/L | 2.0 mg/L | 1.5 mg/L |
| At 175° C. | 1.8 mg/L | 2.5 mg/L | 3.4 mg/L |
| With 3 grams sample |  |  |  |
| At 175° C. | 2.3 mg/L |  |  |
| With 4 grams sample |  |  |  |
| At 175° C. | 2.9 mg/L |  |  |

EXAMPLE 18

Efficacy Tests Using SC, PO and PP $2 \times 10^6$ B. subtilis var. niger spores were inoculated on a SS blade. Three inoculated blades were first placed in the front, middle and back positions of a Spunguard wrapped 10"×21"×3.5" polyphenylene oxide tray. The wrapped tray was then placed in a 75 liter vacuum chamber having an initial vacuum pressure of 0.2 torr. A 5.5" peroxide disk was made by heat-sealing the SC, SO or PP inorganic peroxide powders between three layers of Spunguard and one layer of aluminum foil coated with polypropylene film. The peroxide was released by contacting the disk for 2 minutes with an aluminum plate which had been preheated to 175° C., followed by an additional diffusion time of 8 minutes for a total exposure time of 10 minutes. After treatment, the three blades were separately placed in Trypticase Soy Broth (TSB) at 32° C. for 7 days and scored for bacterial growth. The results are summarized in Table 18.

TABLE 18

EFFICACY TEST RESULTS

| Peroxide Complex | Weight of Complex | Peroxide Conc. | Sterility (+/n) |
|---|---|---|---|
| PP | 2 grams | 3.4 mg/l | 0/3 |
| PO | 2 grams | 2.5 mg/l | 0/3 |
| SC | 2 grams | 1.8 mg/l | 1/3 |
| SC | 3 grams | 2.3 mg/l | 0/3 |
| SC | 4 grams | 2.9 mg/l | 0/3 |

As can be seen in Table 18, no growth of spores was observed with the exception of 2 g SC (1/3). However, when the amount of SC subjected to vaporization was increased to 3 grams, no bacterial growth was observed. These results underscore the efficacy of sterilization using inorganic hydrogen peroxide complexes.

Inorganic hydrogen peroxide complexes can be readily incorporated into the sterilization procedures described hereinabove in connection with organic peroxide complexes. For example, inorganic complexes can be used in connection with a plasma sterilization method, or in connection with a self-sterilizing enclosure where peroxide is slowly released from the complex. Similarly, inorganic complexes can also be used in the sterilization of articles having narrow lumens, whereby a vessel containing the inorganic peroxide complex is connected to the lumen. In addition, pressure pulsing of the vapor released from inorganic peroxide complexes can be employed. Other examples of the use of inorganic complexes for sterilization will be apparent to one having ordinary skill in the art upon reference to the present specification.

Synthesis of Phosphate and Condensed Phosphate Peroxide Complexes

Some phosphate and condensed phosphate peroxide complexes, along with procedures for their synthesis reported in the literature, are summarized in Table 19. In general, these complexes can be synthesized by mixing the phosphate salts with aqueous hydrogen peroxide solution (either adding solid to peroxide solution or adding the peroxide solution to the solid). Since the heat generated by the reaction may result in decomposition of hydrogen peroxide, attempts have been made to control the reaction temperature by slowly mixing solid with the peroxide solution or using cooled peroxide solution (e.g., 0° C.). Peroxide complexes have also been formed by dissolving the hydrate of phosphate or condensed phosphate salts in peroxide solution.

TABLE 19

| Starting Compounds | | | Complex | |
|---|---|---|---|---|
| solids | $H_2O_2$ | Synthesis | Formula | Ref. |
| $Na_4P_2O_7$ | ≧65% | adding $Na_4P_2O_7$ to $H_2O_2$ sol. slowly to control temp. below 50° C. | $Na_4P_2O_7 \cdot nH_2O_2$ n = 2, 3 or higher | 1 |
| $Na_4P_2O_7$ | ≧50% | reacting 3 mol. 50% $H_2O_2$ with 1 mol. $Na_4P_2O_7$, drying in fluidized bed at lower temp. | $Na_4P_2O_7 \cdot 3H_2O_2$ | 2 |
| $Na_4P_2O_7 \cdot 10H_2O$ | 30–90% | adding $Na_4P_2O_7 \cdot 10H_2O$ to $H_2O_2$ sol and drying in vacuum at 20° C. | $Na_4P_2O_7 \cdot 3H_2O_2$ | 3 |
| $Na_3PO_4 \cdot 12H_2O$ | 30% | adding $Na_3PO_4 \cdot 12H_2O$ to $H_2O_2$ sol and drying in vacuum at 20° C. | $Na_3PO_4 \cdot 5H_2O_2$ | 4 |
| $Na_2HPO_4 \cdot 12H_2O$ | 4–76% | adding $Na_2HPO_4 \cdot 12H_2O$ to $H_2O_2$ sol and drying in vacuum at 20° C. | $Na_2HPO_4 \cdot nH_2O_2$ n = 1, 2 | 4 |
| $Na_5P_3O_{10}$ | 60% | spraying $H_2O_2$ sol onto $Na_5P_3O_{10}$ in fluidized bed at 40–50° C., then drying in the bed. | $Na_5P_3O_{10} \cdot nH_2O_2$ n<1 | 5 |
| $K_3PO_4 \cdot 7H_2O$ | 65–70% | dissolving $K_3PO_4 \cdot 7H_2O$ to $H_2O_2$ sol at 0° C., maintaining temp. below 70° C. | $K_3PO_4 \cdot nH_2O_2$ n = 1, 2, 4 | 6 |
| $K_4P_2O_7$ | 60–90% | adding $K_4P_2O_7$ slowly to $H_2O_2$ sol to maintain temp. below 50° C. The results showed that no complex was formed using this procedure when large quantity of staring solid (e.g. 174 g)was employed. | $K_4P_2O_7 \cdot nH_2O_2$ n = 5.35, 7 | 7 |

1 Richmond, Howard, PCT Publication No. WO 95/05341
2 Xiao et al., Faming Zhuanli Shenqing Gongkai Shoumingshu, CN 1,097,798, 25 Jan 1995.
3 Titova et al. Russ. J. Inorg. Chem. 40[3]:384 (1995).
4 Titova et al., Russ. J Inorg. Chem. 39[5]:754 (1994).
5 Kudo, I., Japan Kokai, (C1.CO1B), Aug. 29, 1975, Appl. 74 15,389, Feb. 08, 1974.
6 Kirsanova, M. P., Bogdanov, G.A., Dymova, Z.N., Safonov, V.V., Izv. Vyssh. Ucheb. Zaved. Kjim. Khim. Tekhnol. 15(2):183–6 (1972).
7 Majewski, H.W., U.S. Pat. No. 3,650,750.

Spray Method

Procedures similar to those previously described in the literature were performed to determine the ease and limitations of the procedures for preparing phosphate and condensed phosphate complexes. In general, complexes were prepared by spraying peroxide solution onto evenly spread solid salts, followed by vacuum or oven drying. Table 20 summarizes the complexes synthesized by the spray method. $Na_4P_2O_7 \cdot 3 H_2O_2$ could not be synthesized using a 30% $H_2O_2$ solution which is consistent with the prior art. The $K_3PO_4$ peroxide complex could not be prepared by directly adding $H_2O_2$ solution to anhydrous $K_3PO_4$ at room temperature. Detailed synthesis conditions are provided in Examples 21 to 36 below.

TABLE 20

| Starting Compounds | | | | Ex- |
|---|---|---|---|---|
| solids | $H_2O_2$ | Synthesis | Complex Formula | amples |
| $Na_4P_2O_7$ | >50% | spraying $H_2O_2$ sol. onto $Na_4P_2O_7$ | $Na_4P_2O_7 \cdot nH_2O_2$ n = 3, or higher | 21–27 |
| $Na_4P_2O_7$ | 30% | spraying $H_2O_2$ sol. onto $Na_4P_2O_7$ | $Na_4P_2O_7 \cdot nH_2O_2$ n<=2 | 26 |
| $Na_3PO_4$ | 30–70% | spraying $H_2O_2$ sol. onto $Na_3PO_4$ | $Na_3PO_4 \cdot 5H_2O_2$ | 28 |
| $Na_2HPO_4$ | 30–70% | spraying $H_2O_2$ sol. onto $Na_2HPO_4$ | $Na_2HPO_4 \cdot nH_2O_2$ n = 1, 2 | 29 |
| $Na_5P_3O_{10}$ | 30–70% | spraying $H_2O_2$ sol. onto $Na_5P_3O_{10}$ | $Na_5P_3O_{10} \cdot nH_2O_2$ n = 1–2 | 30 |

TABLE 20-continued

| Starting Compounds | | | | Ex- |
|---|---|---|---|---|
| solids | $H_2O_2$ | Synthesis | Complex Formula | amples |
| $K_3PO_4$ | 59% | spraying $H_2O_2$ sol. onto $K_3PO_4$ | no complex formed | 31 |
| $K_4P_2O_7$ | 59–70% | spraying $H_2O_2$ sol. onto $K_4P_2O_7$ | $K_4P_2O_7 \cdot nH_2O_2$ n = 4–7 | 32 |
| $K_2HPO_4$ | 59% | spraying $H_2O_2$ sol. onto $K_2HPO_4$ | $K_2HPO_4 \cdot 3.15H_2O_2$ | 33 |
| $KH_2PO_4$ | 59% | spraying $H_2O_2$ sol. onto $KH_2PO_4$ | $KH_2PO_4 \cdot 1H_2O_2$ | 34 |
| $Ca_2P_2O_7$ | 59% | spraying $H_2O_2$ sol. onto $Ca_2P_2O_7$ | $Ca_2P_2O_7 \cdot 3.42H_2O_2$ | 35 |
| $Mg_2P_2O_7$ | 59% | spraying $H_2O_2$ sol. onto $Mg_2P_2O_7$ | $Mg_2P_2O_7 \cdot 4.60H_2O_2$ | 36 |

Liquid-Spray Synthesis of $Na_4P_2O_7 \cdot nH_2O_2$

In general, an anhydrous complex of sodium pyrophosphate and hydrogen peroxide ($Na_4P_2O_7 \cdot nH_2O_2$) was synthesized using a liquid-solid phase reaction followed by vacuum and/or oven drying. A number of parameters were varied in connection with the liquid-spray synthesis of a complex of sodium pyrophosphate and hydrogen peroxide, as described below in Examples 21–27. Concentrated hydrogen peroxide solution (30–90% $H_2O_2$) was sprayed onto sodium pyrophosphate (98%, Aldrich) dropwise. The mixture was incubated at 10° C., 25° C. or 45° C. for 1–16 hours, followed by vacuum drying at 25° C.–60° C. and/or oven drying at 60° C. $H_2O_2$ concentration, starting $H_2O_2$ to $Na_4P_2O_7$ molar ratio, solid to liquid ratio, incubation time and temperature, drying mode, drying temperature and quantity of starting materials were varied as described in the following examples to determine their effect on product composition.

Examples 21 to 23 show the effect of drying processes (vacuum drying at 30° C., vacuum drying at 60° C., and oven drying at 60° C., respectively) on final wt % of $H_2O_2$ in the resulting complex with a 2 hour reaction time at 25° C.

Example 24 shows the reaction time effect with vacuum drying at 25° C. The results indicate that a one hour reaction period is sufficient for forming a 1:3 ratio of sodium pyrophosphate to $H_2O_2$ in the complex.

Example 25 shows the reaction temperature effect on peroxide complex formation. The results indicate that the complex with about a 1:3 ratio could still be formed at a temperature below 45° C. when a small quantity of starting materials was employed.

Example 26 shows the effect of hydrogen peroxide concentration on the composition of the resulting peroxide complex using liquid-spray synthesis. As indicated in Table 26, when 30% $H_2O_2$ was sprayed onto sodium pyrophosphate solid, even at a starting $H_2O_2$ to SP molar ratio of 4:1, the resulting complex, $Na_4P_2O_7 \cdot 1.64\ H_2O_2$, had a $H_2O_2$ to SP ratio of less than 2:1 (bis-peroxyhydrate). The tris-peroxyhydrate ($Na_4P_2O_7 \cdot 3\ H_2O_2$) could be formed when the concentration of $H_2O_2$ was greater than 45%, preferably greater than 50%. The composition of $Na_4P_2O_7 \cdot 4\ H_2O_2$, with a $H_2O_2$ to SP ratio of 4:1, was only stable at a temperature below 60° C.

Example 27 shows that the sodium pyrophosphate tris-peroxyhydrate complex could not be successfully prepared by the liquid-spray method when a larger quantity of $Na_4P_2O_7$ was used.

EXAMPLE 21

Vacuum Frying at 30° C.

$H_2O_2$ (59%) was mixed with sodium pyrophosphate (SP) at a solid to liquid ratio of 1:0.8, 1:0.9 and 1:1.1 by weight, incubated at 25° C. for 2 hours and dried under vacuum at 30° C. for 4 hours or at 30° C. for 4 hours followed by 60° C. for 15 hours. The product yield ranged from 84% to 99%. The results are summarized in Table 21.

TABLE 21

| Starting Compounds | | | | | Weight % $H_2O_2$ | | |
|---|---|---|---|---|---|---|---|
| | | | | | | Vac-30° C. 4 h + | |
| | | | | | Vacuum | 60° C. 15 h | |
| SP (g) | 59% $H_2O_2$ (g) | $H_2O_2$/SP molar ratio | Reaction Time at 25° C. | Product Weight (g) | dry at 30° C. 4 hs | Sealed[1] | Open[2] |
| 10 g | 8 g | 3.7 | 2 h | 13.5 | 26.81 | 26.11 | 26.18 |
| 10 g | 9 g | 4.2 | 2 h | 13.9 | 27.75 | 26.95 | 26.98 |
| 10 g | 11 g | 5.1 | 2 h | 11.7 | 27.75 | 26.61 | 26.88 |

[1]For sealed condition, the complex was in a tightly capped plastic bottle;
[2]For open condition, the complex was in an open petri dish.

EXAMPLE 22

Vacuum Drying at 60° C.

$H_2O_2$ (59%) was mixed with sodium pyrophosphate at a solid to liquid ratio of 1:0.8, 1:0.9 and 1:1.1 by weight, incubated at 25° C. for 2 hours and dried under vacuum at 60° C. for 4 hours. The results are summarized in Table 22.

TABLE 22

| Starting Compounds | | | | | Weight % $H_2O_2$ | |
|---|---|---|---|---|---|---|
| SP (g) | 59% $H_2O_2$ (g) | $H_2O_2$/SP molar ratio | Reaction Time (hrs) | Reaction Temp. (°C.) | Vacuum dry at 60° C. 4 h | Vac-60° C. 4 h + 60° C. 15 h Open |
| 10 | 8 | 3.7 | 2 | 25 | 26.54 | 25.53 |
| 10 | 9 | 4.2 | 2 | 25 | 26.92 | 26.38 |
| 10 | 11 | 5.1 | 2 | 25 | 26.83 | 26.28 |

EXAMPLE 23

Oven Drying at 60° C.

$H_2O_2$ (59%) was mixed with sodium pyrophosphate at a solid to liquid ratio of 1:0.8, 1:0.9 and 1:1.1 by weight, incubated at 25° C. for 2 hours and oven dried at 60° C. for either 6 hours or 21 hours. The results are summarized in Table 23.

TABLE 23

| Starting Compounds | | | | | Weight % $H_2O_2$ Oven-dry at 60° C. | |
|---|---|---|---|---|---|---|
| SP (g) | 59% $H_2O_2$ (g) | $H_2O_2$/SP molar ratio | Reaction Time (hrs) | Reaction Temp. (°C.) | 6 h | 21 h |
| 10 | 8 | 3.7 | 2 | 25 | 27.22 | 26.63 |
| 10 | 9 | 4.2 | 2 | 25 | 27.10 | 26.87 |
| 10 | 11 | 5.1 | 2 | 25 | 29.57 | 26.74 |

EXAMPLE 24

Reaction Time Effect $H_2O_2$ (59%) was mixed with sodium pyrophosphate at a solid to liquid ratio of 1:0.8 by weight, incubated at 25° C.

for 1, 2 and 16 hours and dried under vacuum at 25° C. for 4 hours. The results are summarized in Table 24.

TABLE 24

| Starting Compounds | | | | | Weight % $H_2O_2$ | |
|---|---|---|---|---|---|---|
| | | | | | Vacuum | |
| SP (g) | 59% $H_2O_2$ (g) | $H_2O_2$/SP molar ratio | Reaction Time (hrs) | Reaction Temp (°C.) | dry at 25° C. 4 h | Vac-25° C. 4 h + 60° C. 15 h Open |
| 10 | 8 | 3.7 | 1 | 25 | 27.45 | 26.77 |
| 10 | 8 | 4.2 | 2 | 25 | 26.81 | 26.18 |
| 10 | 8 | 5.1 | 16 | 25 | 27.01 | 26.96 |
| 25* | 20 | 3.7 | 16 | 25 | 27.12 | 26.90 |

*This sample was used for the thermal stability study in Example 39.

EXAMPLE 25

Reaction Temperature Effect $H_2O_2$ (59%) was mixed with sodium pyrophosphate at a solid to liquid ratio of 1:0.8, 1:1.1 or 1:1.3 by weight, incubated at 10° C., 25° C. or 45° C., and dried under vacuum. The results are summarized in Table 25.

TABLE 25

| Starting Compounds | | | | | Weight % $H_2O_2$ | |
|---|---|---|---|---|---|---|
| SP (g) | 59% $H_2O_2$ (g) | $H_2O_2$/ SP molar ratio | Reaction Time (hrs) | Reaction Temp (°C.) | Vacuum dry at 25° C. 4 h | Vacuum dry at 45° C. 2 h |
| 10 | 8 | 3.7 | 2 | 10 | 27.81 | |
| 10 | 8 | 4.2 | 2 | 25 | 26.81 | |
| 25 | 27 | 5.0 | 1.5 | 45 | | 26.07 |
| 25 | 32.5 | 6.0 | 1.5 | 45 | | 27.23 |

EXAMPLE 26

Effect of $H_2O_2$ Concentration $H_2O_2$ solution having different concentrations was added to sodium pyrophosphate (Aldrich, 98%) dropwise. The mixture was incubated at 25° C. for 2 hours, then vacuum dried at 25° C. for 4 hours, followed by oven drying at 60° C. for 15 hours with the exception of the sample in the last row of Table 26, which was vacuum dried at 25° C. for 4 hours, then oven dried at 40° C. for 9 hours. The results are summarized in Table 26 and indicate that higher concentrations of peroxide are required to make a peroxide complex having a $H_2O_2$ to SP molar ratio of about 1:3.

TABLE 26

| Starting Compounds | | | | Complexes | |
|---|---|---|---|---|---|
| SP (g) | wt of $H_2O_2$ (g) | $H_2O_2$ conc. (%) | $H_2O_2$/SP molar ratio | Weight % $H_2O_2$ | Composition |
| 10 | 15.8 | 30 | 3.7 | 15.69 | $Na_4P_2O_7 \cdot 1.46H_2O_2$ |
| 10 | 17.2 | 30 | 4.0 | 17.36 | $Na_4P_2O_7 \cdot 1.64H_2O_2$ |
| 10 | 11 | 45 | 4.0 | 25.48 | $Na_4P_2O_7 \cdot 2.67H_2O_2$ |
| 10 | 8 | 59 | 3.7 | 26.18 | $Na_4P_2O_7 \cdot 2.78H_2O_2$ |
| 10 | 9 | 59 | 4.2 | 26.98 | $Na_4P_2O_7 \cdot 2.89H_2O_2$ |
| 10 | 12 | 90 | 5.6 | 27.16 | $Na_4P_2O_7 \cdot 2.92H_2O_2$ |
| 10 | 12 | 90 | 5.6 | 34.44* | $Na_4P_2O_7 \cdot 4.11H_2O_2$ |

*The sample was dried under vacuum at 25° C. for 4 hours and then in an oven at 40° C. for 9 hours.

EXAMPLE 27

Effect of Quantity of Starting Compound

59% $H_2O_2$ solution at room temperature was slowly sprayed onto sodium pyrophosphate solid; however, the temperature of the mixture increased. When 59% $H_2O_2$ was added to 300 grams SP, the temperature of the mixture climbed to over 60° C. thus, larger quantities of SP do not appear to work as well as smaller quantities. The results are summarized in Table 27.

TABLE 27

| SP (g) | 59% $H_2O_2$ (g) | $H_2O_2$/SP molar ratio | Temp. during mixing (°C.) | Incubation Time at 25° C. (hours) | Drying condition | Weight % $H_2O_2$ |
|---|---|---|---|---|---|---|
| 10 | 8 | 3.7 | ~35 | 1 | vac-25° C. 3.5 h + oven –60° C. 15 h | 26.77 |
| 100 | 80 | 3.7 | ~45 | 3 | vac-25° C. 3.5 h + oven –60° C. 15 h | 25.86 |
| 300 | 250 | 3.7 | over 60 | 3 | vac-45° C. 15 h | 19.98 |

Several additional liquid-spray syntheses of additional peroxide complexes are described in Examples 28–34 below.

EXAMPLE 28

Liquid-Spray Synthesis of $Na_3PO_4.5\ H_2O_2$

Aqueous hydrogen peroxide solutions having hydrogen peroxide concentrations of 30%, 59% and 70% were sprayed onto solid sodium orthophosphate, tribasic (SPT; 96%, Aldrich) to form a paste. The mixture was incubated for 2 hours at 25° C., then vacuum dried at 25° C. The results are summarized in Table 28.

EXAMPLE 29

Liquid Synthesis of $Na_2HPO_4.H_2O_2$ and $Na_2HPO_4.2\ H_2O_2$

Sodium phosphate, dibasic solid (99.95%, Aldrich) was dissolved in aqueous hydrogen peroxide solution and incubated at 25° C. for 1 hour, then dried under vacuum at 25° C. The resulting product was a gel having a $Na_2HPO_4/H_2O_2$ ratio of about 1:2. Further drying of the gel resulted in a powder having a $Na_2HPO_4/H_2O_2$ ratio of about 1:1. The results are summarized in Table 29.

TABLE 29

| Starting Compounds | | | | Complexes | | | |
|---|---|---|---|---|---|---|---|
| $Na_2HPO_4$ (g) | wt of $H_2O_2$ (g) | $H_2O_2$ conc. (%) | $H_2O_2$/ $Na_2HPO_4$ molar ratio | Weight % $H_2O_2$ | Composition in gel form | Weight % $H_2O_2$ | Composition in powder form |
| 5 | 12.0 | 30 | 3.0 | | | 20.37 | $Na_2HPO_4.1.07H_2O_2$ |
| 5 | 19.8 | 30 | 5.0 | 33.72 | $Na_2HPO_4.2.12H_2O_2$ | 23.01 | $Na_2HPO_4.1.25H_2O_2$ |
| 5 | 6.1 | 59 | 3.0 | 27.88 | $Na_2HPO_4.1.61H_2O_2$ | 22.28 | $Na_2HPO_4.1.20H_2O_2$ |
| 5 | 10.2 | 59 | 5.0 | 35.33 | $Na_2HPO_4.2.28H_2O_2$ | 20.85 | $Na_2HPO_4.1.10H_2O_2$ |
| 5 | 5.1 | 70 | 3.0 | 31.31 | $Na_2HPO_4.1.92H_2O_2$ | | |
| 5 | 8.5 | 70 | 5.0 | 35.13 | $Na_2HPO_4.2.26H_2O_2$ | 21.49 | $Na_2HPO_4.1.14H_2O_2$ |

TABLE 28

| Starting Compounds | | | | Complexes | |
|---|---|---|---|---|---|
| $Na_3PO_4$ (g) | wt of $H_2O_2$ (g) | $H_2O_2$ conc. (%) | $H_2O_2$/ $Na_3PO_4$ molar ratio | Weight % $H_2O_2$ | Composition |
| 5 | 34.6 | 30 | 10 | 51.70 | $Na_3PO_4.5.16H_2O_2$ |
| 5 | 17.6 | 59 | 10 | 52.23 | $Na_3PO_4.5.27H_2O_2$ |
| 5 | 14.8 | 70 | 10 | 48.81 | $Na_3PO_4.4.60H_2O_2$ |

EXAMPLE 30

Liquid-Spray Synthesis of $Na_5P_3O_{10}.1–2\ H_2O_2$

Concentrated hydrogen peroxide solution was sprayed onto sodium tripolyphosphate (85%, Aldrich) (STP) dropwise. The mixture was incubated at 25° C. for 1 hour, vacuum dried at 25° C., and then oven dried at 60° C. Results are shown in Table 30.

TABLE 30

| Starting Compounds | | | | Complexes | |
|---|---|---|---|---|---|
| $Na_5P_3O_{10}$ (g) | $H_2O_2$ (g) | $H_2O_2$ conc. (%) | $H_2O_2$/ $Na_5P_3O_{10}$ molar ratio | Weight % $H_2O_2$ | Composition |
| 10 | 13.0 | 30 | 5.0 | 10.58 | $Na_5P_3O_{10} \cdot 1.40H_2O_2$ |
| 10 | 6.6 | 59 | 5.0 | 12.58 | $Na_5P_3O_{10} \cdot 1.62H_2O_2$ |
| 10 | 5.6 | 70 | 5.0 | 13.40 | $Na_5P_3O_{10} \cdot 1.73H_2O_2$ |

EXAMPLE 31

Liquid-Spray Synthesis of $K_3PO_4 \cdot nH_2O_2$

59% $H_2O_2$ at room temperature was added dropwise to potassium phosphate, tribasic (97%, Aldrich). The temperature of the reaction mixture during the spraying climbed to about 80° C. The paste mixture was dried under vacuum for 4 hours. The results are summarized in Table 31 and indicate that the majority of peroxide in the complex decomposed due to the high reaction temperature.

TABLE 31

| Starting Compounds | | | | Reaction product | |
|---|---|---|---|---|---|
| $K_3PO_4$ (g) | $H_2O_2$ (g) | $H_2O_2$ conc. (%) | $H_2O_2$/ $K_3PO_4$ molar ratio | Weight % $H_2O_2$ | Composition |
| 10 | 8 | 59 | 3.0 | 0.34 | $K_3PO_4 \cdot 0.02H_2O_2$ |

EXAMPLE 32

Liquid-Spray Synthesis of $K_4P_2O_7 \cdot nH_2O_2$

Aqueous hydrogen peroxide solution having a concentration of 59% or 70% was sprayed onto potassium pyrophosphate (PP) (97%, Aldrich) to form a paste, the temperature of which was about 30° C. to 35° C. during spraying. The mixture was incubated at 25° C. for 2 hours, then dried under vacuum at 25° C. The results are summarized in Table 32.

TABLE 32

| Starting Compounds | | | | Complexes | |
|---|---|---|---|---|---|
| $K_4P_2O_7$ (g) | $H_2O_2$ (g) | $H_2O_2$ conc. (%) | $H_2O_2$/ $K_4P_2O_7$ molar ratio | Weight % $H_2O_2$ | Composition |
| 10 | 8.0 | 59 | 4.6 | 28.74 | $K_4P_2O_7 \cdot 3.91H_2O_2$ |
| 10 | 9.5 | 59 | 5.4 | 33.70 | $K_4P_2O_7 \cdot 4.74H_2O_2$ |
| 10 | 11.0 | 59 | 6.4 | 36.30 | $K_4P_2O_7 \cdot 5.67H_2O_2$ |
| 10 | 17.5 | 59 | 10 | 41.64 | $K_4P_2O_7 \cdot 6.93H_2O_2$ |
| 10 | 21.0 | 59 | 12 | 41.48 | $K_4P_2O_7 \cdot 6.99H_2O_2$ |
| 10 | 14.7 | 70 | 10 | 42.80 | $K_4P_2O_7 \cdot 7.26H_2O_2$ |
| 10 | 17.6 | 70 | 12 | 41.11 | $K_4P_2O_7 \cdot 6.78H_2O_2$ |

EXAMPLE 33

Liquid-Spray Synthesis of $K_2HPO_4 \cdot 3 H_2O_2$

Concentrated hydrogen peroxide solution was sprayed onto potassium hydrogen phosphate (98%, Aldrich) (PHP) dropwise. The mixture was incubated at 25° C. for 1 hour and vacuum dried at 25° C. The results are shown in Table 33.

TABLE 33

| Starting Compounds | | | | Complex | |
|---|---|---|---|---|---|
| $K_2HPO_4$ (g) | $H_2O_2$ (g) | $H_2O_2$ conc. (%) | $H_2O_2$/ $K_2HPO_4$ molar ratio | Weight % $H_2O_2$ | Composition |
| 5 | 4.97 | 59 | 3.0 | 38.04 | $K_2HPO_4 \cdot 3.15H_2O_2$ |

EXAMPLE 34

Liquid-Spray Synthesis of $KH_2PO_4 \cdot H_2O_2$

Concentrated hydrogen peroxide solution was sprayed onto potassium dihydrogen phosphate (98%, Aldrich) (PDHP) dropwise. The mixture was incubated at 25° C. for 1 hour and vacuum dried at 25° C. The results are shown in Table 34.

TABLE 34

| Starting Compounds | | | | Complex | |
|---|---|---|---|---|---|
| $KH_2PO_4$ (g) | $H_2O_2$ (g) | $H_2O_2$ conc. (%) | $H_2O_2$/ $KH_2PO_4$ molar ratio | Weight % $H_2O_2$ | Composition |
| 5 | 6.23 | 59 | 3.0 | 20.18 | $KH_2PO_4 \cdot H_2O_2$ |

EXAMPLE 35

Liquid-Spray Synthesis of $Ca_2P_2O_7 \cdot 3.42\ H_2O_2$

59% aqueous hydrogen peroxide solution was sprayed onto solid calcium pyrophosphate (Aldrich). The mixture was incubated for 1 hour at 25° C., then vacuum dried at 25° C. The results are summarized in Table 35.

TABLE 35

| Starting Compounds | | | | Complex | |
|---|---|---|---|---|---|
| $Ca_2P_2O_7$ (g) | $H_2O_2$ (g) | $H_2O_2$ conc. (%) | $H_2O_2$/ $Ca_2P_2O_7$ molar ratio | Weight % $H_2O_2$ | Composition |
| 5 | 10 | 59 | 8.82 | 31.41 | $Ca_2P_2O_7 \cdot 3.42H_2O_2$ |

EXAMPLE 36

Liquid-Spray Synthesis of $Mg_2P_2O_7 \cdot 4.60\ H_2O_2$

59% aqueous hydrogen peroxide solution was sprayed onto solid magnesium pyrophosphate (Aldrich). The mixture was incubated for 1 hour at 25° C., then vacuum dried at 25° C. The results are summarized in Table 36.

TABLE 36

| | Starting Compounds | | | Complex | |
|---|---|---|---|---|---|
| $Mg_2P_2O_7$ (g) | wt of $H_2O_2$ $H_2O_2$ (g) | $H_2O_2$ conc. (%) | $H_2O_2/$ $Mg_2P_2O_7$ molar ratio | Weight % $H_2O_2$ | Composition |
| 5 | 10 | 59 | 7.72 | 41.28 | $Mg_2P_2O_7\cdot4.60H_2O_2$ |

Although several phosphate peroxide complexes have been described, no general method of synthesis for producing stable complexes is known. The reaction between hydrogen peroxide solution and a phosphate or condensed phosphate is an exothermic reaction. The heat produced by this exothermic reaction can result in decomposition of the hydrogen peroxide. As a result, the complex may be unstable, or may have a lower ratio of peroxide to phosphate or condensed phosphate than desired. This problem is particularly pronounced when a large quantity of complex is prepared.

Paste Method

In an effort to control the heat produced by reaction of hydrogen peroxide solution with the phosphate or condensed phosphate, we have developed a variety of synthesis methods. One such method we call the "paste" method because a paste is initially formed from the phosphate or condensed phosphate with water. This paste-liquid synthetic method for inorganic hydrogen peroxide complexes comprises mixing the desired inorganic compound with water to form a soft paste. The paste is allowed to cool, and aqueous hydrogen peroxide solution is added to the inorganic paste. The resulting mixture is dried to remove water, yielding the inorganic hydrogen peroxide complex.

The main advantage of this synthetic scheme is that while the reaction of inorganic compound with water is exothermic, very little heat is generated during formation of the inorganic peroxide complex, thus avoiding the degradation of hydrogen peroxide during the synthesis. This is a significant improvement over previous methods in which significant amounts of heat are generated which degrade the hydrogen peroxide. The resulting crystals of the inorganic peroxide complex are finer and more stable than those produced according to other procedures and lower concentrations of $H_2O_2$ can also be used.

Without wishing to be bound by any particular theory or mechanism of action, we believe that a hydrate is initially formed upon formation of the paste, and that the water from these hydrates is then replaced with peroxide to form the inorganic peroxide complexes. Examples 37 and 38 provide exemplary methods for the production of two different phosphate peroxide complexes.

EXAMPLE 37

Paste-Liquid Synthesis of $Na_4P_2O_7\cdot2$–$3\ H_2O_2$ Using Different $H_2O_2$ Concs.

Sodium pyrophosphate solid (98%, Aldrich) was mixed with deionized water and slowly stirred, resulting in formation of a soft paste. Because this reaction is exothermic, the paste was allowed to cool to room temperature. Aqueous $H_2O_2$ solution having different $H_2O_2$ concentrations was mixed with the paste. No temperature increase occurred. The mixture was incubated at 25° C. for 1 hour, then vacuum dried at 25° C. The vacuum dried samples were further oven dried at 60° C. to remove any remaining water. The results are summarized in Table 37.

TABLE 37

| | Starting Compounds | | | | Complexes | |
|---|---|---|---|---|---|---|
| SP (g) | wt of $H_2O$ (g) | wt of $H_2O_2$ (g) | $H_2O_2$ conc. (%) | $H_2O_2/SP$ molar ratio | Weight % $H_2O_2$ | Composition |
| 5 | 5 | 24.4 | 12 | 4.6 | 26.60 | $Na_4P_2O_7\cdot2.84H_2O_2$ |
| 5 | 5 | 9.8 | 30 | 4.6 | 27.92 | $Na_4P_2O_7\cdot3.03H_2O_2$ |
| 5 | 5 | 2.4 | 59 | 2.2 | 17.16 | $Na_4P_2O_7\cdot1.62H_2O_2$ |
| 5 | 5 | 3.0 | 59 | 2.8 | 19.67 | $Na_4P_2O_7\cdot1.92H_2O_2$ |
| 5 | 5 | 3.2 | 59 | 3.2 | 24.43 | $Na_4P_2O_7\cdot2.53H_2O_2$ |
| 5 | 5 | 4 | 59 | 3.7 | 26.02 | $Na_4P_2O_7\cdot2.75H_2O_2$ |
| 5 | 5 | 5 | 59 | 4.6 | 28.10 | $Na_4P_2O_7\cdot3.06H_2O_2$ |
| 50* | 50 | 50 | 59 | 4.6 | 27.40 | $Na_4P_2O_7\cdot2.95H_2O_2$ |
| 200 | 200 | 200 | 59 | 4.6 | 28.31 | $Na_4P_2O_7\cdot3.01H_2O_2$ |

*This sample was used for the thermal stability study in Example 39.

Table 37 shows several advantages of the paste method for the preparation of hydrogen peroxide complexes:

1. The starting concentration of $H_2O_2$ was not restricted to greater than 50% in order to prepare sodium pyrophosphate tris-peroxyhydrate ($Na_4P_2O_7\cdot3\ H_2O_2$). The complex could be prepared when as low as 12% $H_2O_2$ solution was employed.

2. $Na_4P_2O_7\cdot3\ H_2O_2$ could be successfully prepared using larger quantities of starting materials (e.g. 200 g SP), because no temperature increase occurred during mixing of $H_2O_2$ solution with SP-water paste.

3. Peroxide complexes having different compositions can easily be prepared by controlling the $H_2O_2$ to SP molar ratio in the starting mixture.

EXAMPLE 38

Paste-Liquid Synthesis of $K_3PO_4\cdot nH_2O_2$

Potassium phosphate, tribasic (97%, Aldrich) (PPT) was mixed with deionized water and slowly stirred, resulting in formation of a soft paste which was allowed to cool to room temperature. Aqueous $H_2O_2$ solution (59%) was mixed with the paste. No temperature increase was observed. The mixture was incubated at 25° C. for 2 hours and dried under vacuum at 25° C. The results are summarized in Table 38. Potassium phosphate peroxide could not be formed by the liquid-spray procedure (as shown in Example 31) which is used for most phosphate-peroxide complex syntheses. When a hydrogen peroxide solution was sprayed onto solid potassium phosphate, the temperature of the reaction mixture climbed to about 80° C. This high temperature most likely results in the decomposition of hydrogen peroxide so that minimal incorporation of hydrogen peroxide into potassium phosphate occurred. The paste method is clearly superior to the liquid-spray method for the preparation of the $K_3PO_4\cdot3\ H_2O_2$ complex.

TABLE 38

| | Starting Compounds | | | $H_2O_2$/ | | Complex | |
|---|---|---|---|---|---|---|---|
| $K_3PO_4$ (g) | wt of $H_2O$ (g) | wt of $H_2O_2$ (g) | $H_2O_2$ conc. (%) | $K_3PO_4$ molar ratio | Weight % $H_2O_2$ | Composition | |
| 5 | 2 | 6.6 | 59 | 5.0 | 34.57 | $K_3PO_4 \cdot 3.34H_2O_2$ | |

EXAMPLE 39

Thermal Stability of $Na_4P_2O_7 \cdot 3\ H_2O_2$ Prepared Using Spray Method and Paste Method Approximately 0.3 g complex sample was stored in a 5 ml plastic bottle which was either left unscrewed (open, condition 1) or tightly capped (sealed, condition 2). The open and sealed bottles were placed in a 23° C., 50% relative humidity (RH) incubator or a 60° C. oven. The $H_2O_2$ content of the complex was then determined. The results are summarized in Table 39.

TABLE 39

| Synthesis method | Storage condition* | Testing condition | wt % $H_2O_2$ | | | | |
|---|---|---|---|---|---|---|---|
| | | | 1w | 2w | 3w | 4w | 6w |
| SPRAY | (1) | 23° C., 50% RH | 26.35 | 27.04 | 26.10 | 26.38 | N/A |
| | | 60° C., in oven | 25.76 | 24.57 | 20.39 | 21.22 | N/A |
| | (2) | 23° C., 50% RH | 26.86 | 26.71 | 26.87 | 26.81 | 26.84 |
| | | 60° C., in oven | 26.70 | 25.10 | 23.61 | 21.33 | 17.70 |
| PASTE | (1) | 23° C., 50% RH | 26.85 | 26.93 | 26.73 | 26.64 | 26.98 |
| | | 60° C., in oven | 26.84 | 26.29 | 25.58 | 24.78 | 23.73 |
| | (2) | 23° C., 50% RH | 27.15 | 27.04 | 26.98 | 26.72 | 27.33 |
| | | 60° C., in oven | 26.87 | 27.74 | 26.17 | 26.10 | 25.71 |

*Storage condition: (1) unscrewed plastic bottle; (2) tightly capped plastic bottle.

Comparing the results reported in Table 39, the stability of the complex produced via the spray method was less stable at 60° C. than the complex prepared via the paste method. However, the stability at 23° C. and 50% relative humidity was roughly comparable. Thus, the paste method offers unexpected stability under adverse storage conditions, such as commonly occur during shipping.

Hydrate Method

As discussed above, we believe that the paste method initially produces a hydrate of the phosphate or condensed phosphate. For many phosphate or condensed phosphate compounds, hydrates can either be readily produced using techniques well known to those having ordinary skill in the art, or are commercially available. Thus, we tried a hydrate method of synthesis for peroxide complexes which omits the initial paste-formation of the past method, substituting instead a prepared hydrate. As is believed to occur in the past method, the water molecules of the hydrate are replaced by peroxide. Example 40 below provides an exemplary hydrate synthesis method.

EXAMPLE 40

Hydrate Synthesis of $Na_4P_2O_7 \cdot 3\ H_2O_2$

Sodium pyrophosphate decahydrate solid (99%, Aldrich) was mixed with 12%, 30% or 59% aqueous hydrogen peroxide solution, incubated for one hour at 25° C., then vacuum dried at 25° C. The results are summarized in Table 40. Thus, this complex can be prepared with less than 30% hydrogen peroxide solution.

TABLE 40

| Starting Compounds | | | | Complex | |
|---|---|---|---|---|---|
| $Na_4P_2O_7 \cdot 10H_2O$ (g) | wt of $H_2O_2$ (g) | $H_2O_2$ conc. (%) | $H_2O_2$/$Na_4P_2O_7$ molar ratio | Weight % $H_2O_2$ | Composition |
| 8.4 | 24.5 | 12 | 4.6 | 25.87 | $Na_4P_2O_7 \cdot 2.78H_2O_2$ |
| 8.4 | 10.0 | 30 | 4.6 | 28.04 | $Na_4P_2O_7 \cdot 3.05H_2O_2$ |
| 200 | 120 | 59 | 4.6 | 27.57 | $Na_4P_2O_7 \cdot 2.97H_2O_2$ |

Synthesis of Sulfate Peroxide Complexes

We have also synthesized hydrogen peroxide complexes of sulfate salts for use in connection with the sterilization methods described herein. Examples 41 and 42 provide synthetic details for two exemplary sulfate salt complexes.

EXAMPLE 41

Liquid-Spray Synthesis of $Na_2SO_4 \cdot 1.28\ H_2O_2$

59% aqueous hydrogen peroxide solution was sprayed onto solid sodium sulfate (99%+, Aldrich). The mixture was incubated for 1 hour at 25° C., then vacuum dried at 25° C. The results are summarized in Table 41.

TABLE 41

| Starting Compounds | | | | Complex | |
|---|---|---|---|---|---|
| $Na_2SO_4$ (g) | wt of $H_2O_2$ | | $H_2O_2$/ | | |
| | $H_2O$ (g) | conc. (%) | $Na_2SO_4$ molar ratio | Weight % $H_2O_2$ | Composition |
| 10 | 10 | 59 | 2.46 | 23.47 | $Na_2SO_4 \cdot 1.28H_2O_2$ |

EXAMPLE 42

Liquid-Spray Synthesis of $K_2SO_4 \cdot 0.62\ H_2O_2$

59% aqueous hydrogen peroxide solution was sprayed onto solid potassium sulfate (99%+, Aldrich). The mixture was incubated for 1 hour at 25° C., then vacuum dried at 25° C. The results are summarized in Table 42.

TABLE 42

| Starting Compounds | | | | Complex | |
|---|---|---|---|---|---|
| $K_2SO_4$ (g) | wt of $H_2O_2$ | | $H_2O_2$/ | | |
| | $H_2O$ (g) | conc. (%) | $K_2SO_4$ molar ratio | Weight % $H_2O_2$ | Composition |
| 10 | 7 | 59 | 2.12 | 10.82 | $K_2SO_4 \cdot 0.62H_2O_2$ |

Synthesis of Silicate Peroxide Complexes

We have also synthesized hydrogen peroxide complexes of silicate salts for use in connection with the sterilization methods described herein. Examples 43 and 44 provide synthetic details for two exemplary silicate salt complexes.

EXAMPLE 43

Paste-Liquid Synthesis of $Na_2SiO_3 \cdot nH_2O_2$

Solid sodium metasilicate ($Na_2SiO_3$, Aldrich) was mixed with water, resulting in formation of a soft paste, which was allowed to cool to room temperature. Aqueous hydrogen peroxide solution (12%) was mixed with the paste. The temperature during the mixing was 30°–35° C. The mixture was incubated for 1 hour at 25° C., then vacuum dried at 25° C. The results are summarized in Table 43.

TABLE 43

| Starting Compounds | | | | | Complexes | |
|---|---|---|---|---|---|---|
| wt of $Na_2SiO_3$ (g) | wt of $H_2O$ (g) | $H_2O_2$ (g) | $H_2O_2$ conc. (%) | $H_2O_2$/ $Na_2SiO_3$ molar ratio | Weight % $H_2O_2$ | Composition |
| 5 | 5 | 23.22 | 12 | 2.0 | 24.74 | $Na_2SiO_3 \cdot 1.18H_2O_2$ |
| 5 | 5 | 34.83 | 12 | 3.0 | 37.45 | $Na_2SiO_3 \cdot 2.15H_2O_2$ |
| 5 | 5 | 46.45 | 12 | 4.0 | 37.64 | $Na_2SiO_3 \cdot 2.17H_2O_2$ |

EXAMPLE 44

Hydrate Synthesis of $Na_2Si_3O_7 \cdot 0.68\ H_2O_2$

59% aqueous hydrogen peroxide solution was sprayed onto solid sodium trisilicate hydrate ($Na_2Si_3O_7 \cdot xH_2O$, Aldrich). The mixture was incubated for 1 hour at 25° C., then vacuum dried at 25° C. The results are summarized in Table 44.

TABLE 44

| Starting Compounds | | | | Complex | |
|---|---|---|---|---|---|
| $Na_2Si_3O_7 \cdot xH_2O$ (g) | wt of $H_2O_2$ (g) | $H_2O_2$ conc. (%) | $H_2O_2$/ $Na_2Si_3O_7$ molar ratio | Weight % $H_2O_2$ | Composition |
| 5 | 4.76 | 59 | 4.0 | 8.73 | $Na_2Si_3O_7 \cdot 0.68H_2O_2$ |

Thus, we have shown that hydrogen peroxide complexes of a wide variety of inorganic salts can be produced. We believe that successful release of $H_2O_2$ in connection with the sterilization methods disclosed herein can be achieved using a large number of salts of anions capable of hydrogen bonding, such as those that include at least one oxygen and/or nitrogen atom. See, Table 14, supra, for examples of organic complexes and additional inorganic complexes which can be used in connection with the methods of the present invention.

Release of Peroxide from Complexes

The DSC curves shown in previous examples, e.g. FIG. 6, were conducted with one hole on a covered pan at both atmospheric and reduced pressure. With only one small hole on the lid, an exothermic peak was observed in DSC at one atomphere for potassium oxalate peroxide complex. The same test was repeated under atmospheric pressure to determine whether more peroxide can be released using a more open system, as shown below in Example 45.

EXAMPLE 45

$H_2O_2$ Release from $K_2C_2O_4$ Peroxide Complex at Atmospheric Pressure

Potassium oxalate hydrogen peroxide complex ($K_2C_2O_4 \cdot H_2O_2$) was heated at atmospheric pressure using the apparatus shown in FIG. 5, having either two holes in the sealed lid of a sample pan on the heating plate 112 or with an aluminum pan open to the atmosphere. The DSC profile is shown in FIG. 10. A large endothermic peak followed by a small exothermic peak indicated partial release of $H_2O_2$ if the pan was open. A small endothermic peak followed by a large exothermic peak indicated that some release, but mostly degradation, had occurred when the pan had a lid with two holes.

In view of the results of Example 45 that a significant amount of $H_2O_2$ release could occur with an open pan but not using a lid with two holes, we conducted the remainder of our testing of release of peroxide from complexes at atmospheric pressure using an open pan and under reduced pressure using a pan covered with a lid with one hole in DSC. The DSC profiles of a number of inorganic complexes are shown in FIGS. 11–25 and a summary of the thermal behavior of peroxide complexes in DSC studies is shown in Table 45.

Figure 11A:
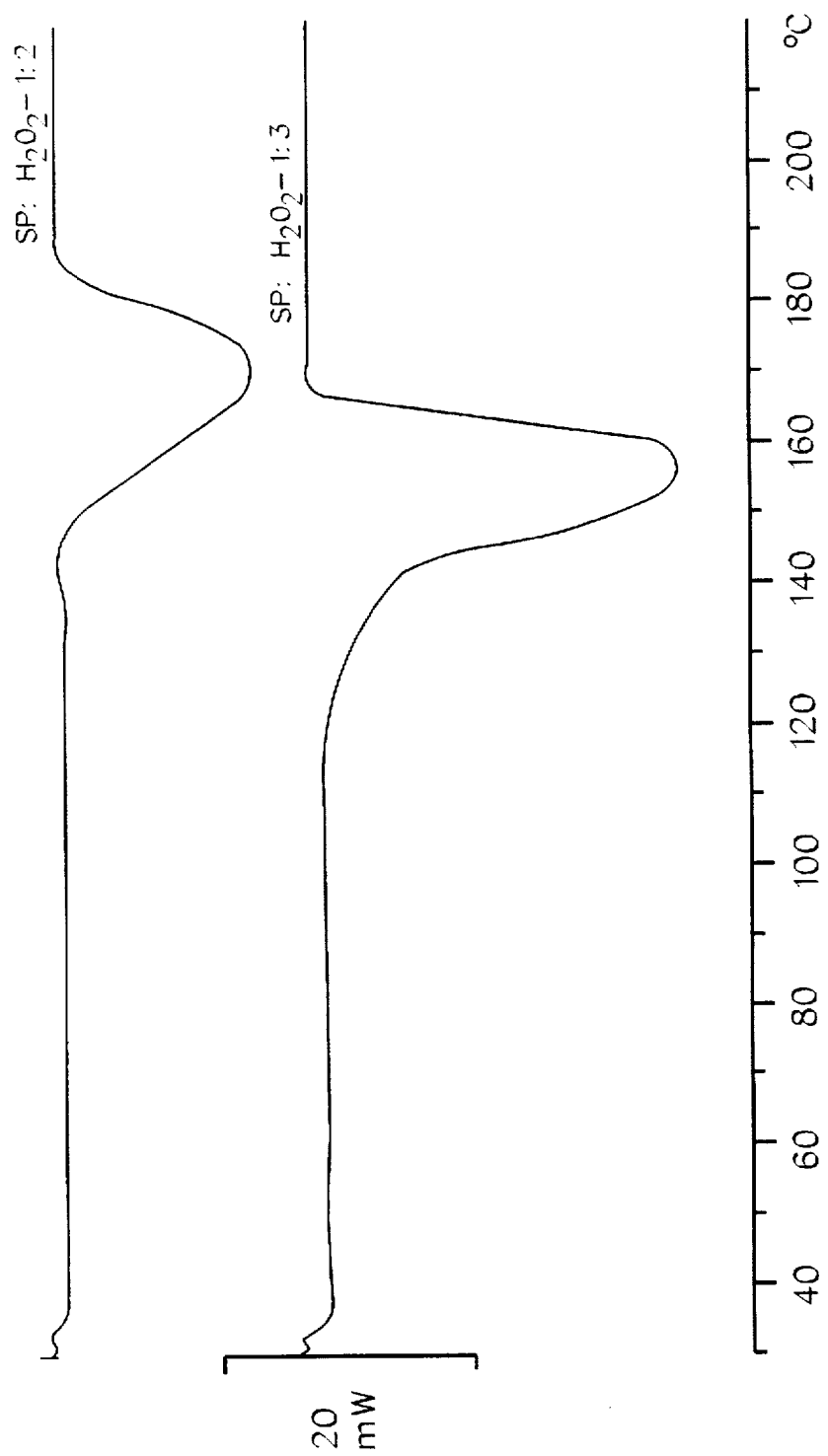
FIG. 11A is a DSC profile of $Na_4P_2O_7.2\ H_2O_2$ and $Na_4P_2O_7.3\ H_2O_2$ at 760 torr.

FIG. 11A is a DSC profile of $Na_4P_2O_7 \cdot 2\ H_2O_2$ and $Na_4P_2O_7 \cdot 3\ H_2O_2$ at 760 torr. As can be seen, one endothermic peak was observed, indicating that near complete release had occurred.

Figure 11B:
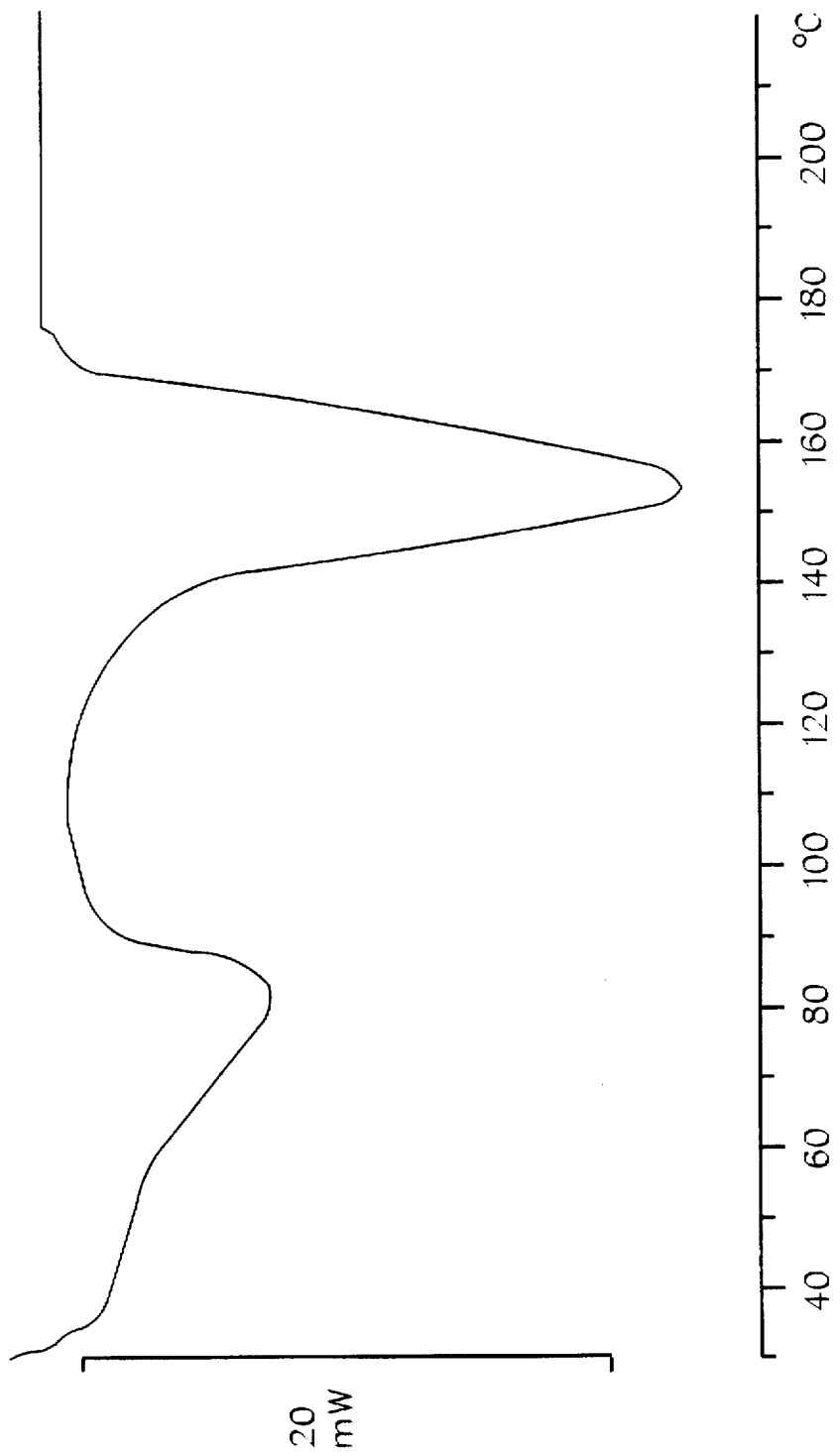
FIG. 11B is a DSC profile of $Na_4P_2O_7.4\ H_2O_2$ at 760 torr.

FIG. 11B is a DSC profile of $Na_4P_2O_7 \cdot 4\ H_2O_2$ at 760 torr. As can be seen, two endothermic peaks were observed, indicating near complete release occurred.

Figure 12:
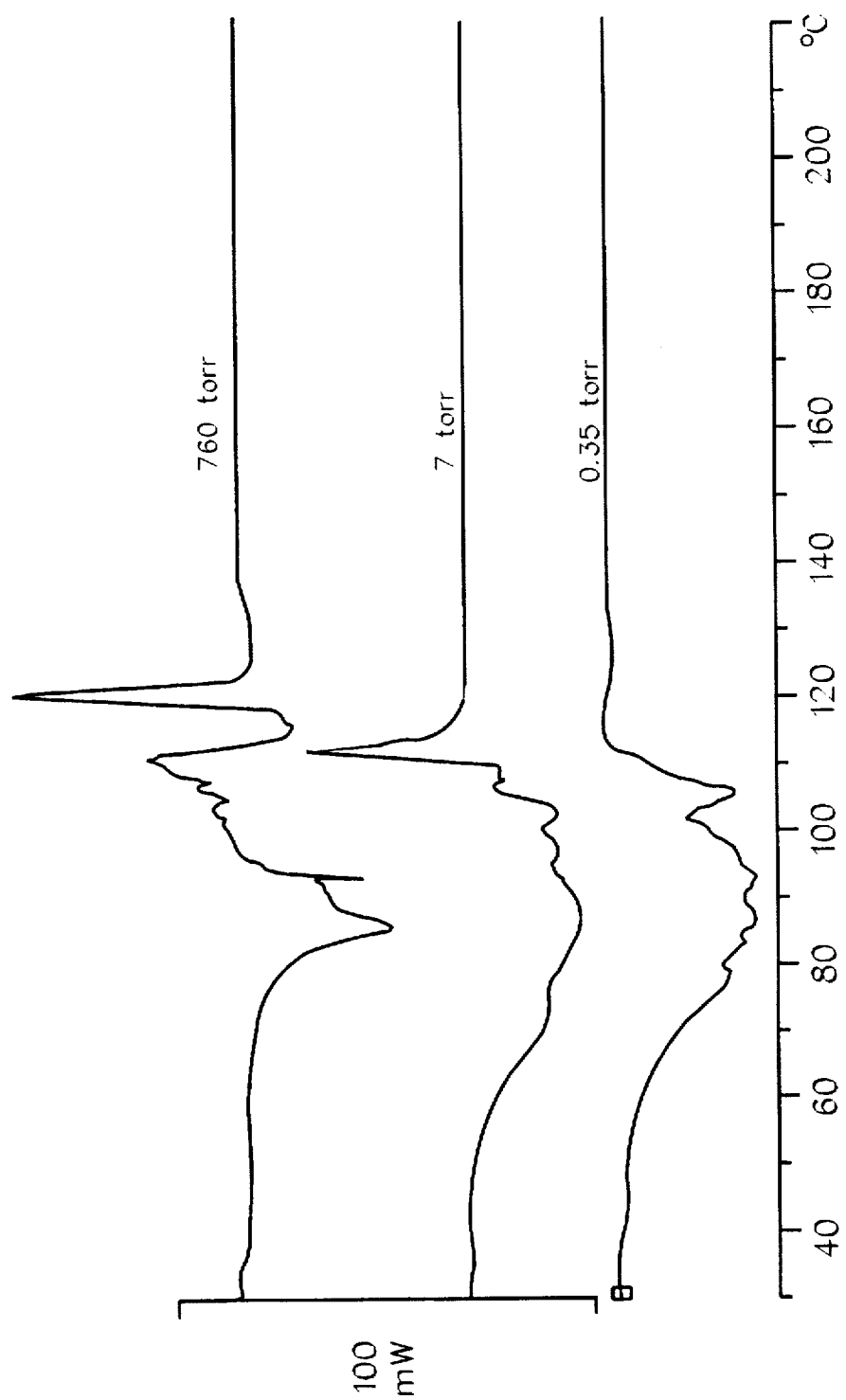
FIG. 12 is a DSC profile of $Na_3PO_4.5\ H_2O_2$ at 760 torr, 7 torr and 0.35 torr.

FIG. 12 is a DSC profile of $Na_3PO_4 \cdot 5\ H_2O_2$ at 760 torr, 7 torr and 0.35 torr. The complex was synthesized using the liquid-spray procedure. As can be seen, endothermic peaks followed by a small exothermic peak indicated that partial release had occurred at one atmosphere. But, under vacuum, a broad endothermic effect indicated near complete release had occurred.

Figure 13:
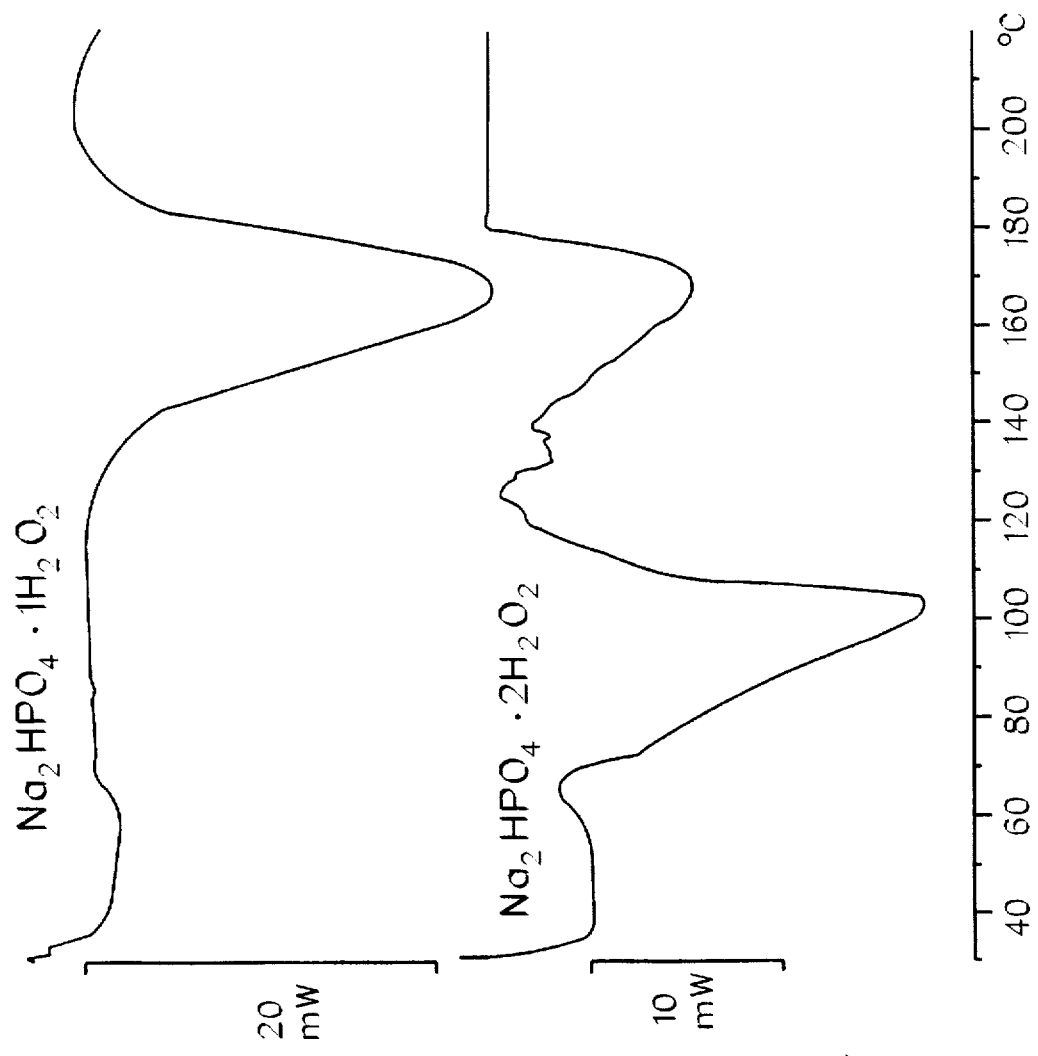
FIG. 13 shows DSC profiles of $Na_2HPO_4.1\ H_2O_2$ and $Na_2HPO_4.2\ H_2O_2$ at 760 torr.

FIG. 13 shows DSC profiles of $Na_2HPO_4 \cdot 1\ H_2O_2$ and $Na_2HPO_4 \cdot 2\ H_2O_2$ at 760 torr. Both complexes showed an endothermic effect in DSC, indicating near total release occurred at atmospheric pressure.

Figure 14:
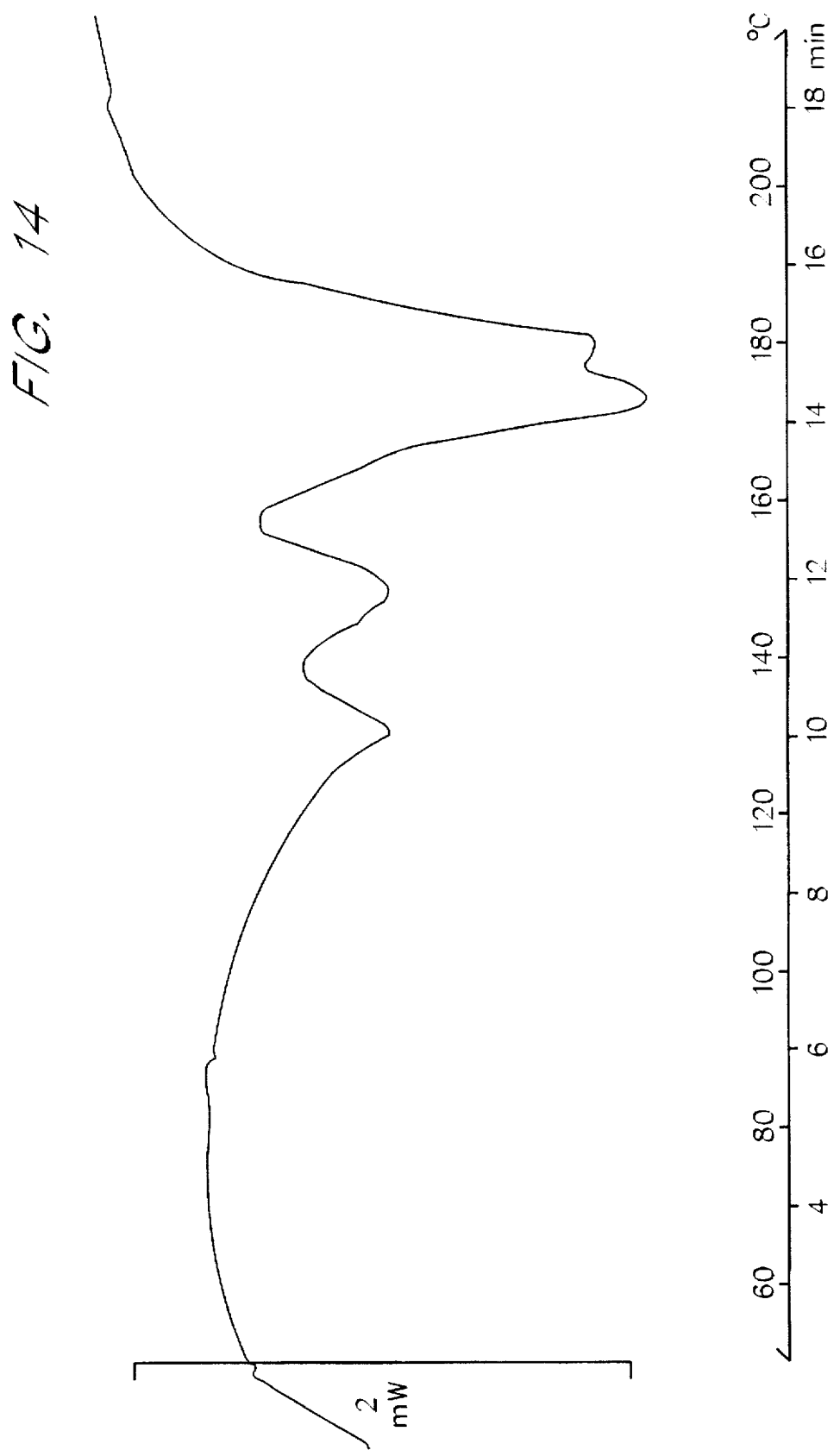
FIG. 14 shows a DSC profile of $Na_5P_3O_{10}.H_2O_2$ at 760 torr.

FIG. 14 shows a DSC profile of $Na_5P_3O_{10} \cdot H_2O_2$ at 760 torr. Several endothermic peaks indicated near total release had occurred under atmospheric pressure.

Figure 15:
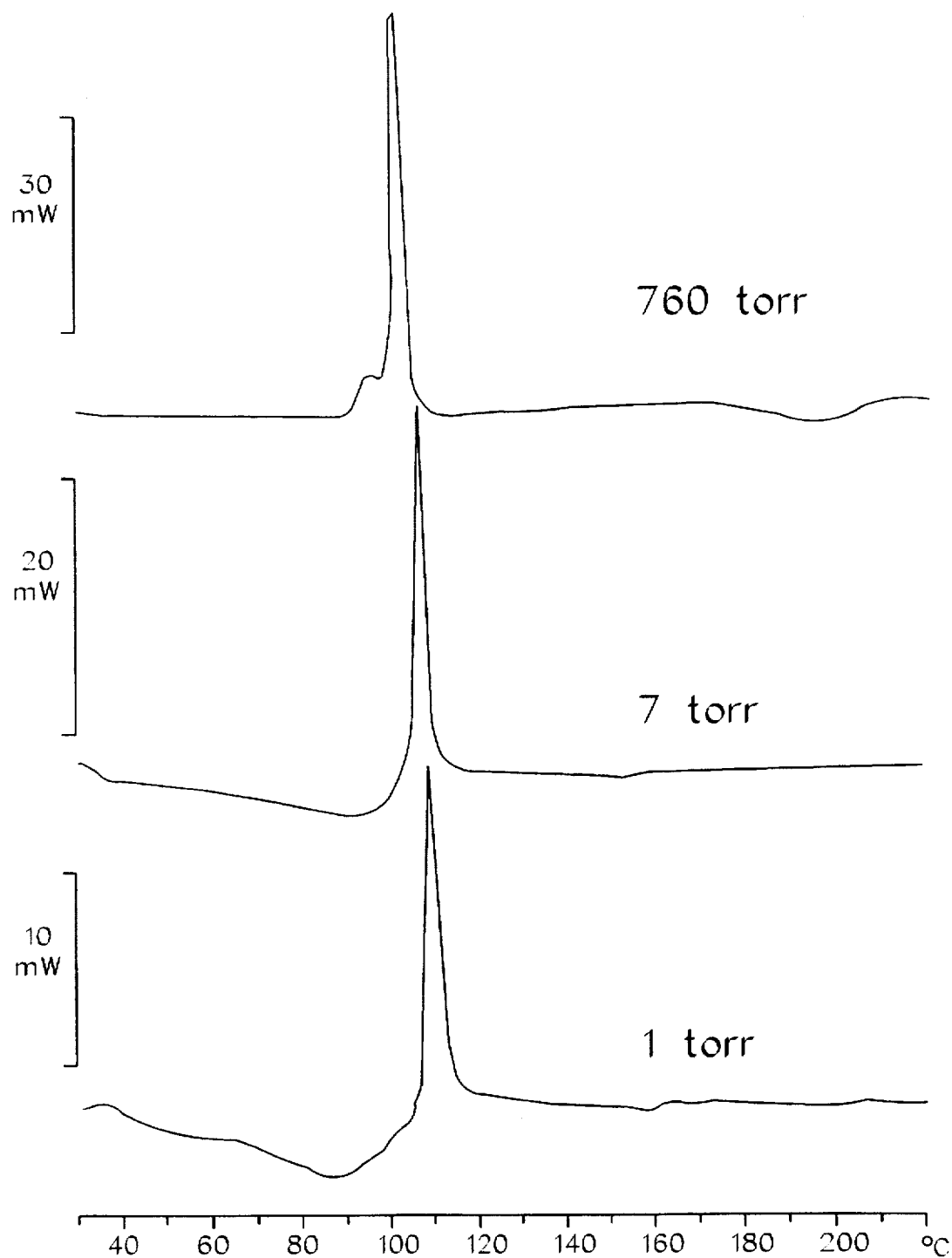
FIG. 15 shows a DSC profile of $K_3PO_4.3.34\ H_2O_2$ at 760 torr, 7 torr and 1 torr.

FIG. 15 shows a DSC profile of $K_3PO_4 \cdot 3.34\ H_2O_2$ at 760 torr, 7 torr and 1 torr. One exothermic peak in DSC at atmospheric pressure indicated that most $H_2O_2$ had decomposed at atmospheric pressure, but partial release occurred under vacuum since an endothermic peak was observed before the exothermic peak under vacuum.

Figure 16:
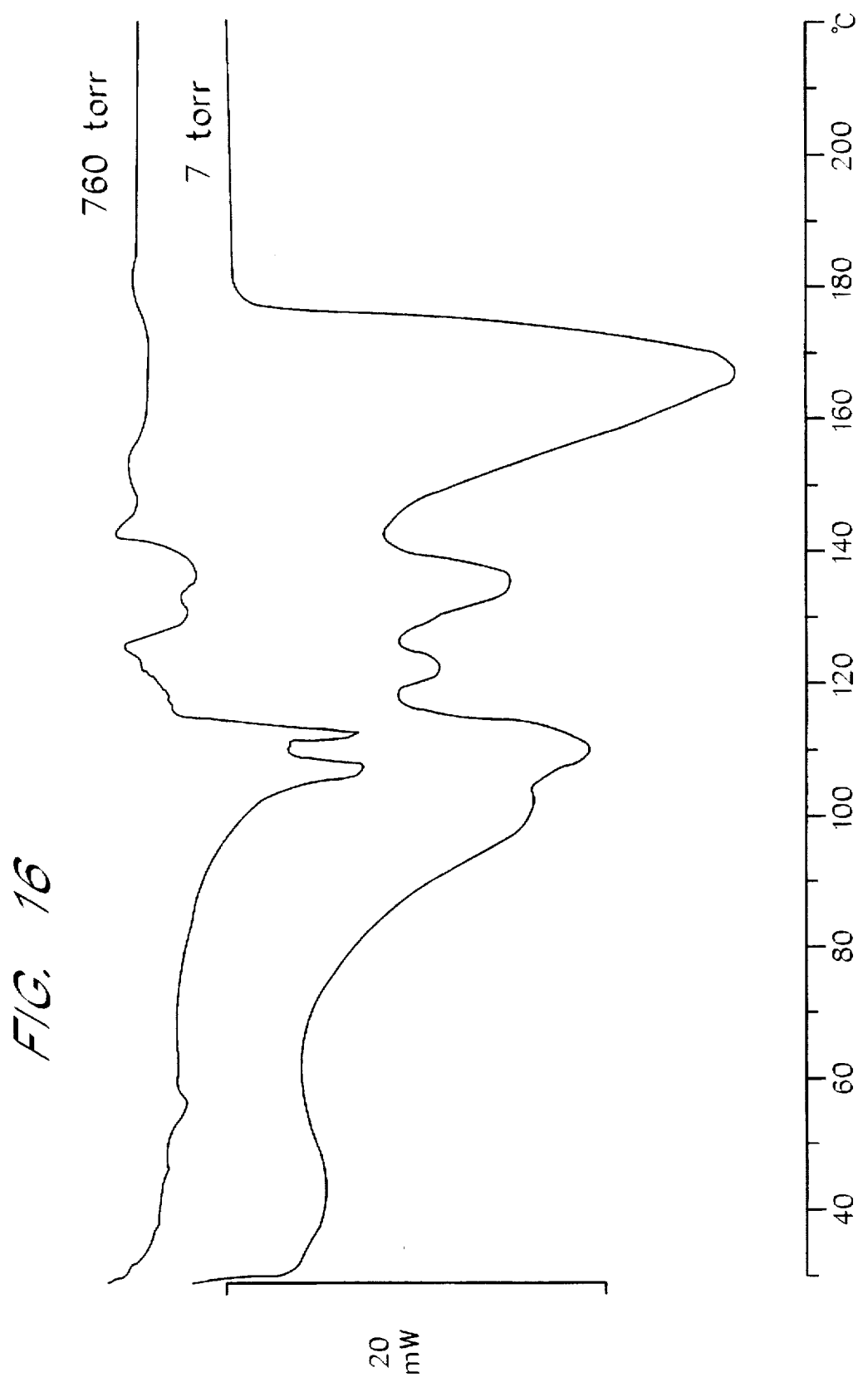
FIG. 16 is a DSC profile of $K_4P_2O_7.7\ H_2O_2$ at 760 torr and 7 torr.

FIG. 16 is a DSC profile of $K_4P_2O_7 \cdot 7\ H_2O_2$ at 760 torr and 7 torr. Based on independently obtained weight loss data, an endothermic peak is likely canceled out by an exothermic peak in the range 140° C.–180° C. at atmospheric pressure. Thus, the DSC shows that partial release occurred at atmospheric pressure. Several endothermic peaks under vacuum indicated near total release under those conditions.

Figure 17:
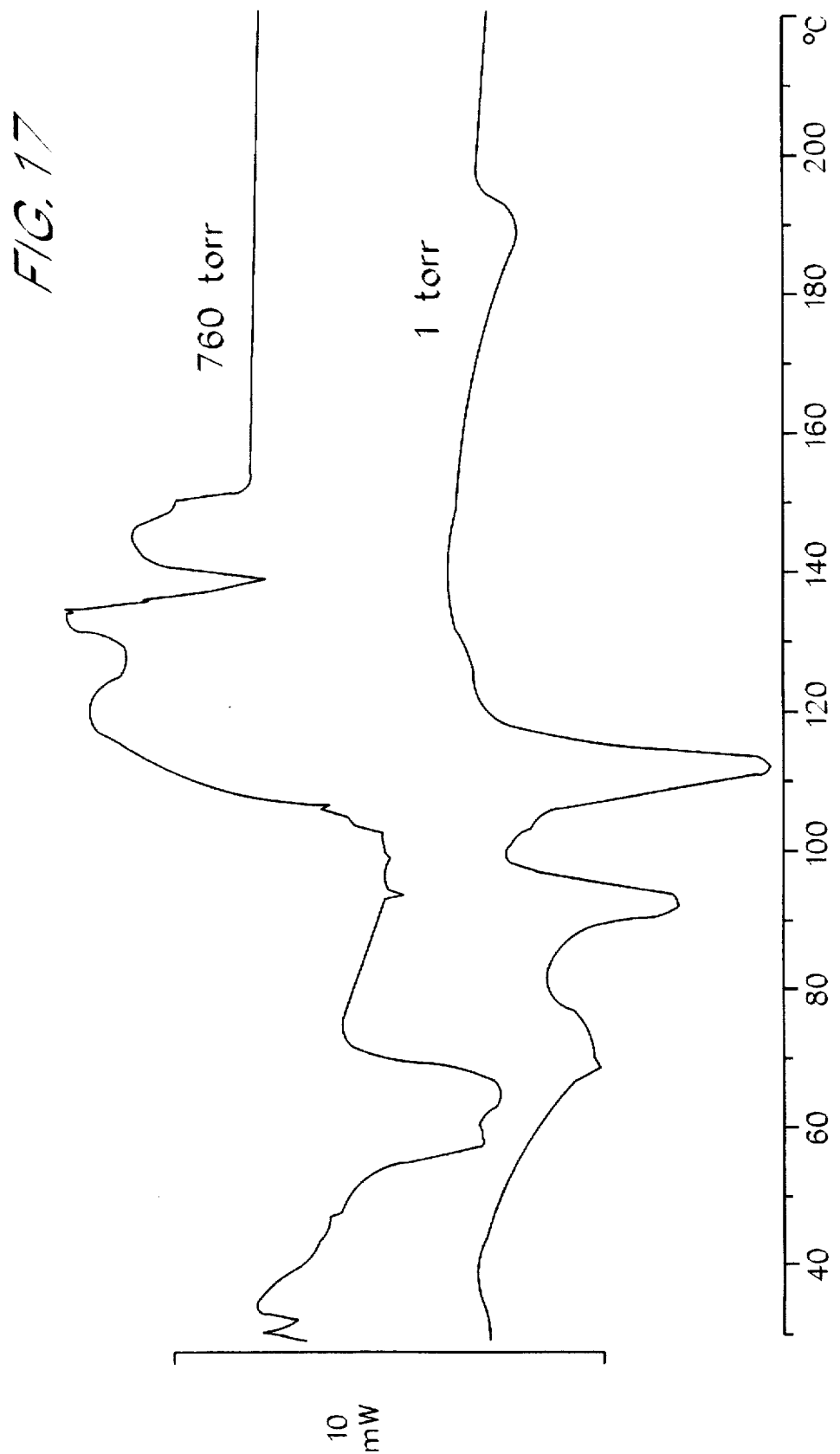
FIG. 17 shows a DSC profile of $K_2HPO_4.3.15\ H_2O_2$ at 760 torr and at 1 torr.

FIG. 17 shows a DSC profile of $K_2HPO_4 \cdot 3.15\ H_2O_2$ at 760 torr and at 1 torr. Several endothermic peaks followed by exothermic peaks indicated that partial release occurred at atmospheric pressure, but no exothermic peaks were observed under vacuum, indicating near total release under those conditions.

Figure 18:
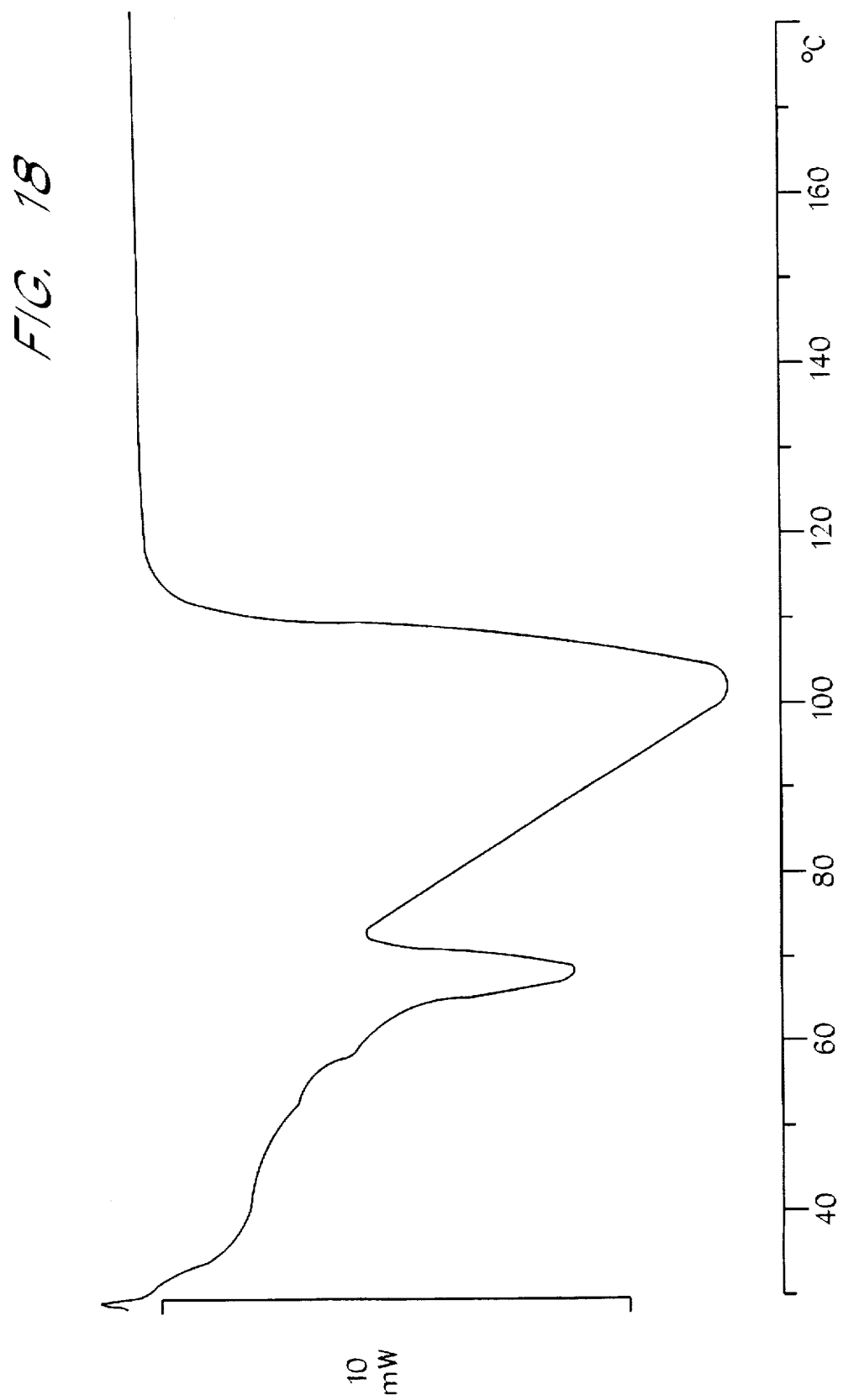
FIG. 18 shows a DSC profile of $KH_2PO_4.H_2O_2$ at 760 torr.

FIG. 18 shows a DSC profile of $KH_2PO_4 \cdot H_2O_2$ at 760 torr. Two endothermic peaks were observed, indicating near total release occurred under atmospheric pressure.

Figure 19:
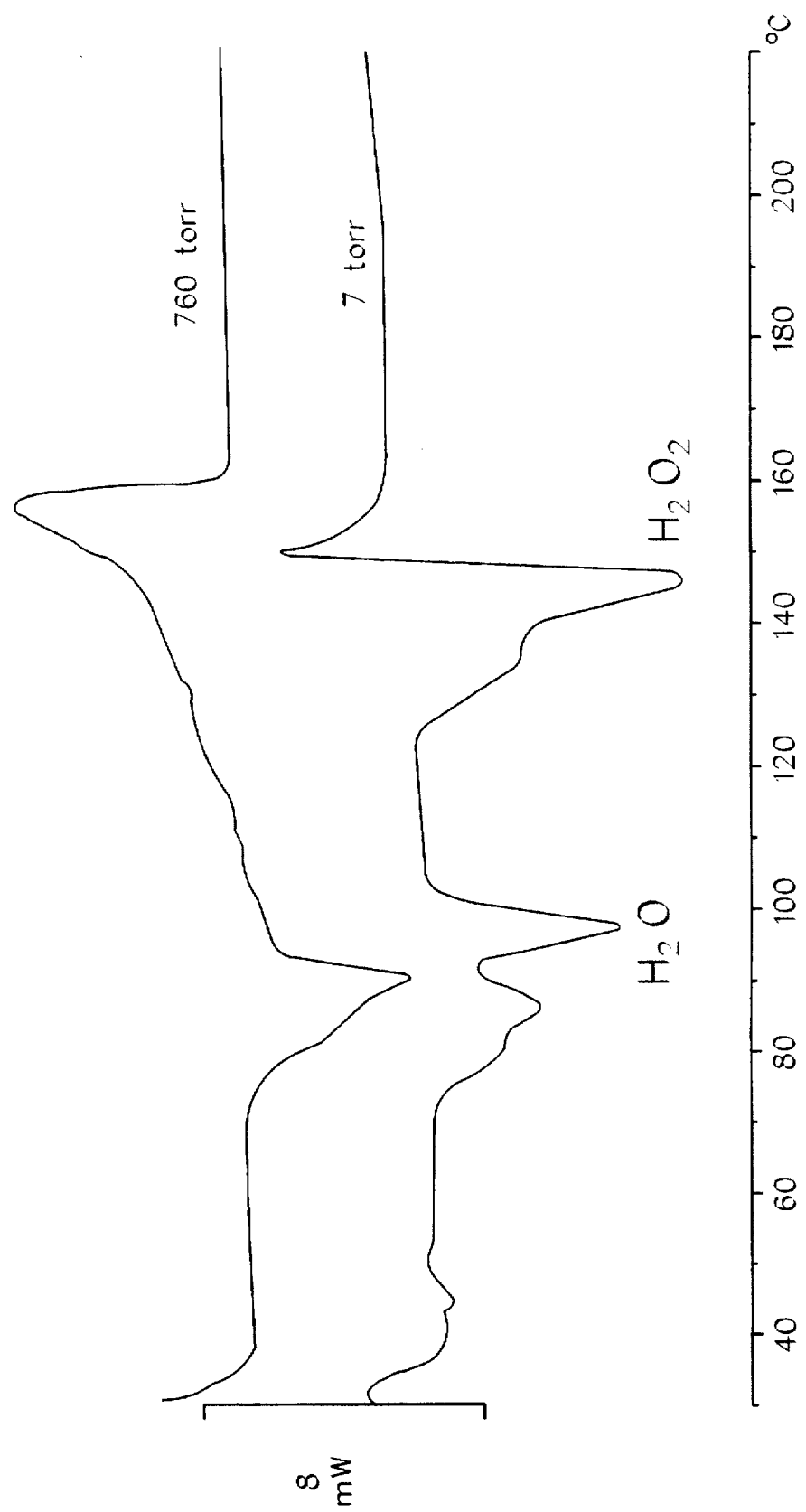
FIG. 19 shows a DSC profile of $Na_2CO_3.1.5\ H_2O_2$ at 760 torr and at 7 torr.

FIG. 19 shows a DSC profile of $Na_2CO_3 \cdot 1.5\ H_2O_2$ at both 760 torr and at 7 torr. The endothermic peak at 90°–100° C. is believed to be release of $H_2O$ under both atmospheric and vacuum conditions. The exothermic peak at approximately 150° C. under atmospheric pressure indicated mostly $H_2O_2$ decomposition. However, the exothermic peak became endothermic followed by a small exothermic peak under vacuum conditions, indicating that most $H_2O_2$ was released.

Figure 20:
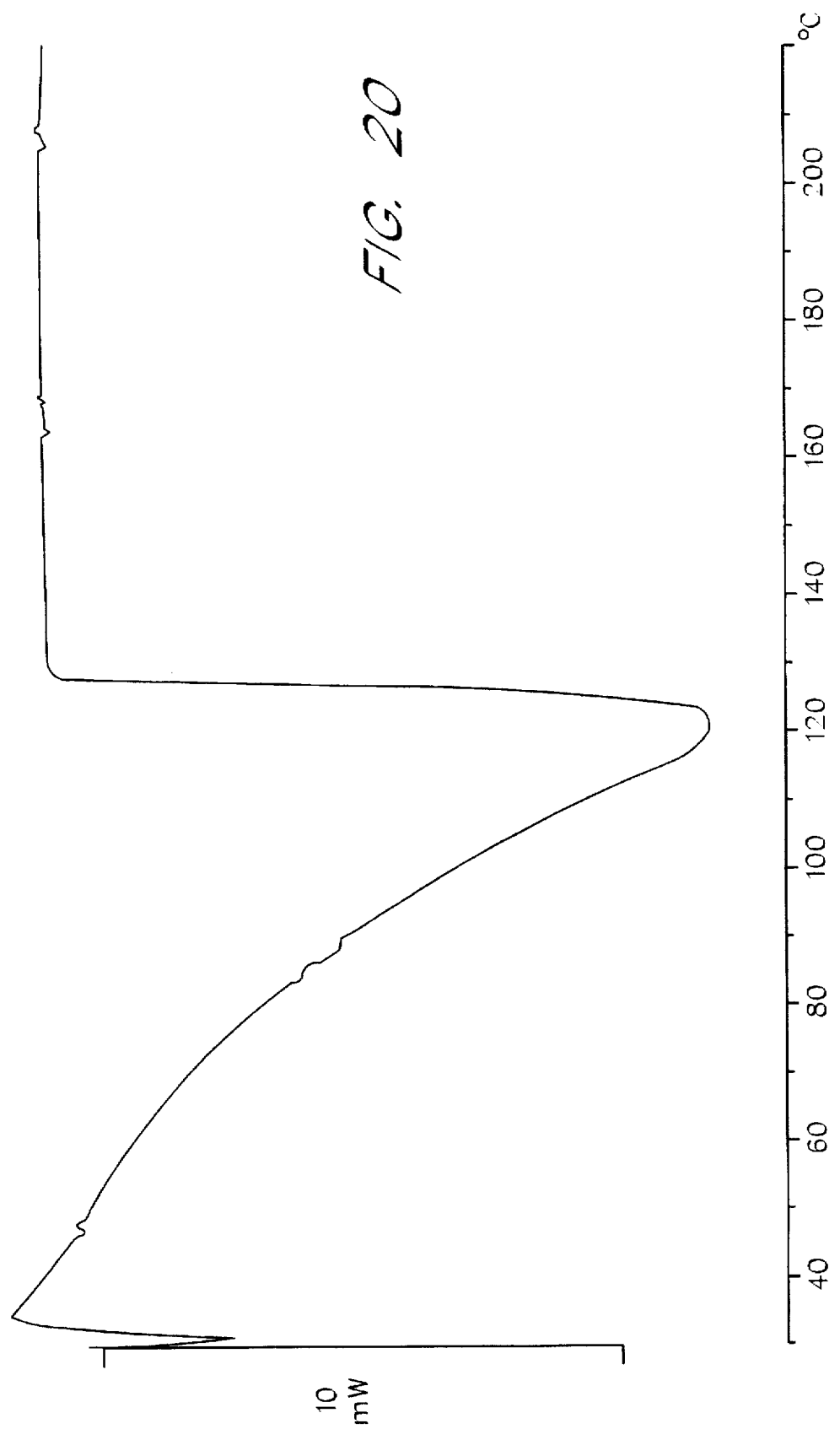
FIG. 20 shows a DSC profile of $Ca_2P_2O_7·3.42\ H_2O_2$ at 760 torr.

FIG. 20 shows a DSC profile of $Ca_2P_2O_7 \cdot 3.42\ H_2O_2$ at 760 torr. An endothermic peak indicated near complete release of $H_2O_2$ had occurred.

Figure 21:
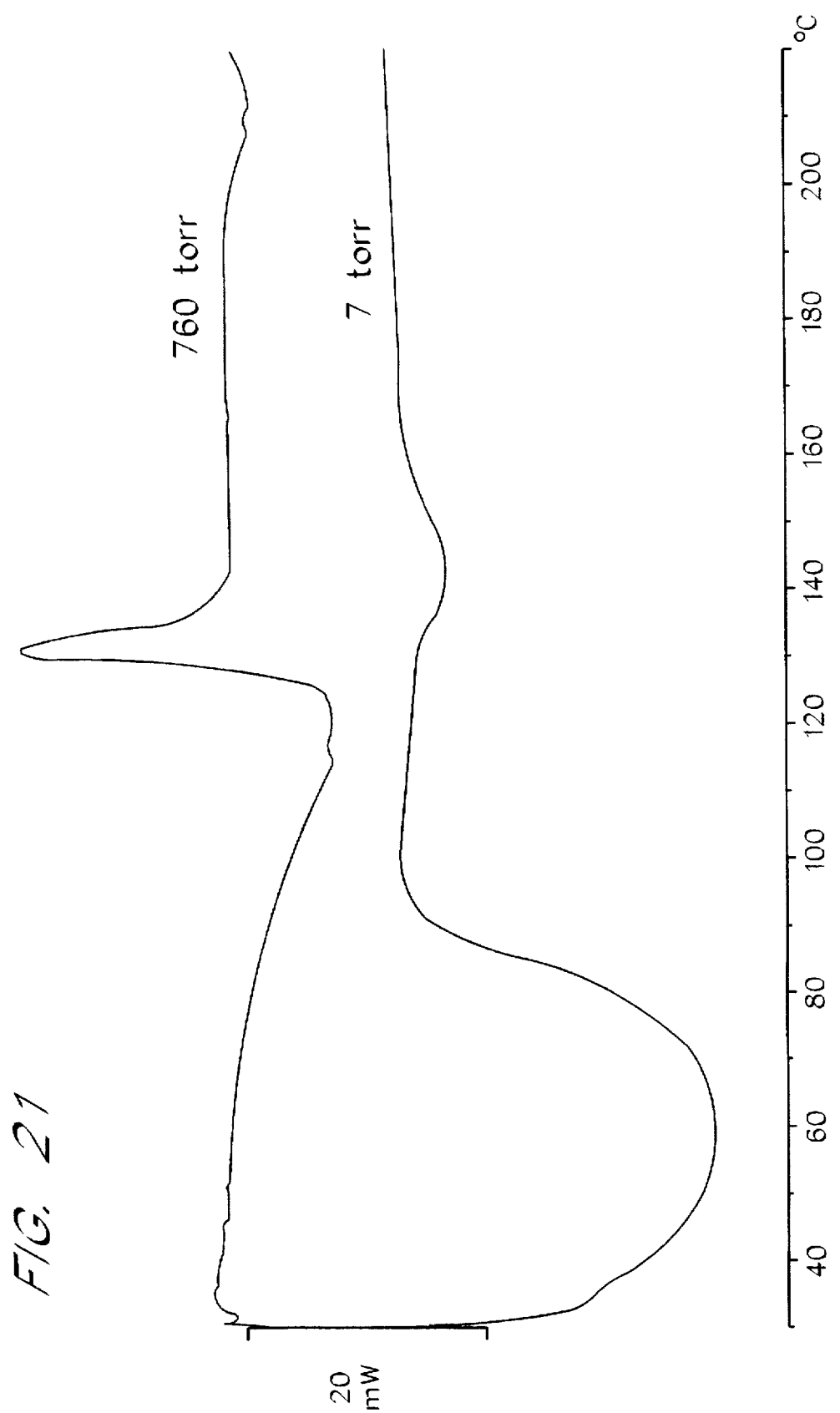
FIG. 21 is a DSC profile of $Mg_2P_2O_7·4.60\ H_2O_2$ at 760 torr and 7 torr.

FIG. 21 is a DSC profile of $Mg_2P_2O_7 \cdot 4.60\ H_2O_2$ at 760 torr and 7 torr. An endothermic peak followed by an exothermic peak indicated partial release of $H_2O_2$ occurred at atmospheric pressure, but a large endothermic peak observed under vacuum indicated near total release under vacuum.

Figure 22:
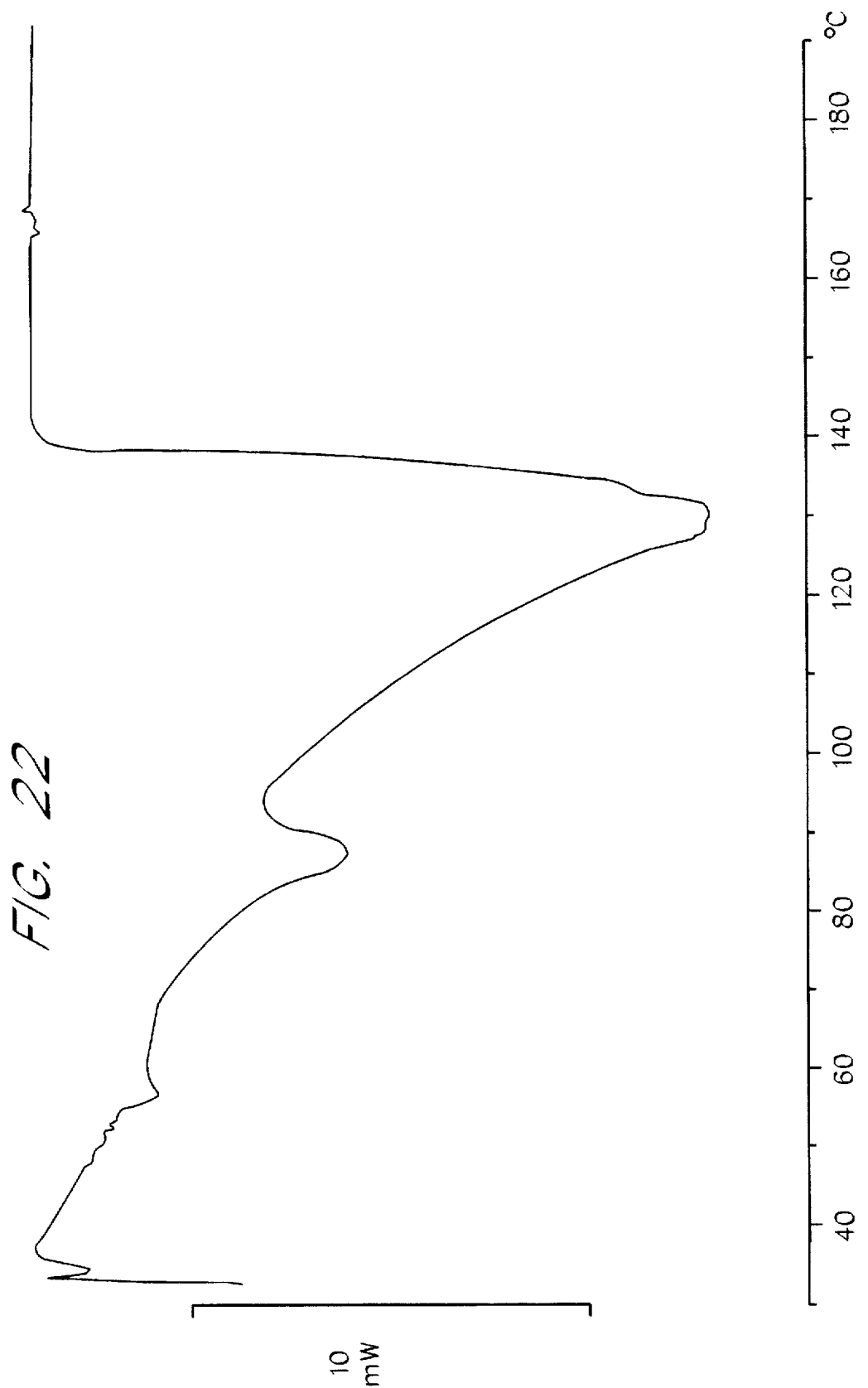
FIG. 22 is a DSC profile of $Na_2SO_4·1.28\ H_2O_2$ at 760 torr.

FIG. 22 is a DSC profile of $Na_2SO_4 \cdot 1.28\ H_2O_2$ at 760 torr. An endothermic peak indicated that near complete release had occurred under atmospheric conditions.

Figure 23:
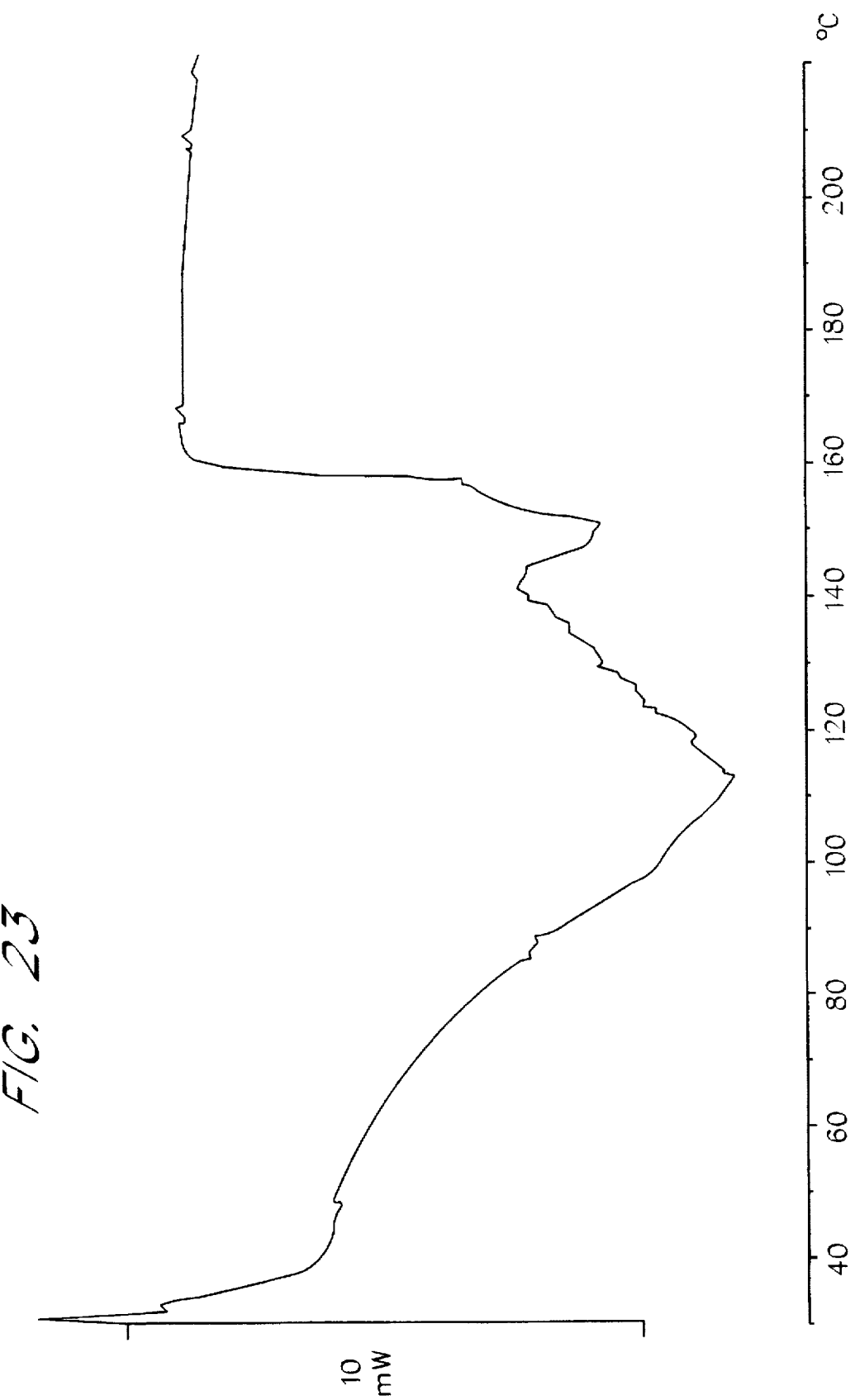
FIG. 23 is a DSC profile of $K_2SO_4·0.62\ H_2O_2$ at 760 torr.

FIG. 23 is a DSC profile of $K_2SO_4 \cdot 0.62\ H_2O_2$ at 760 torr. An endothermic peak indicated that near complete release occurred under atmospheric conditions.

Figure 24:
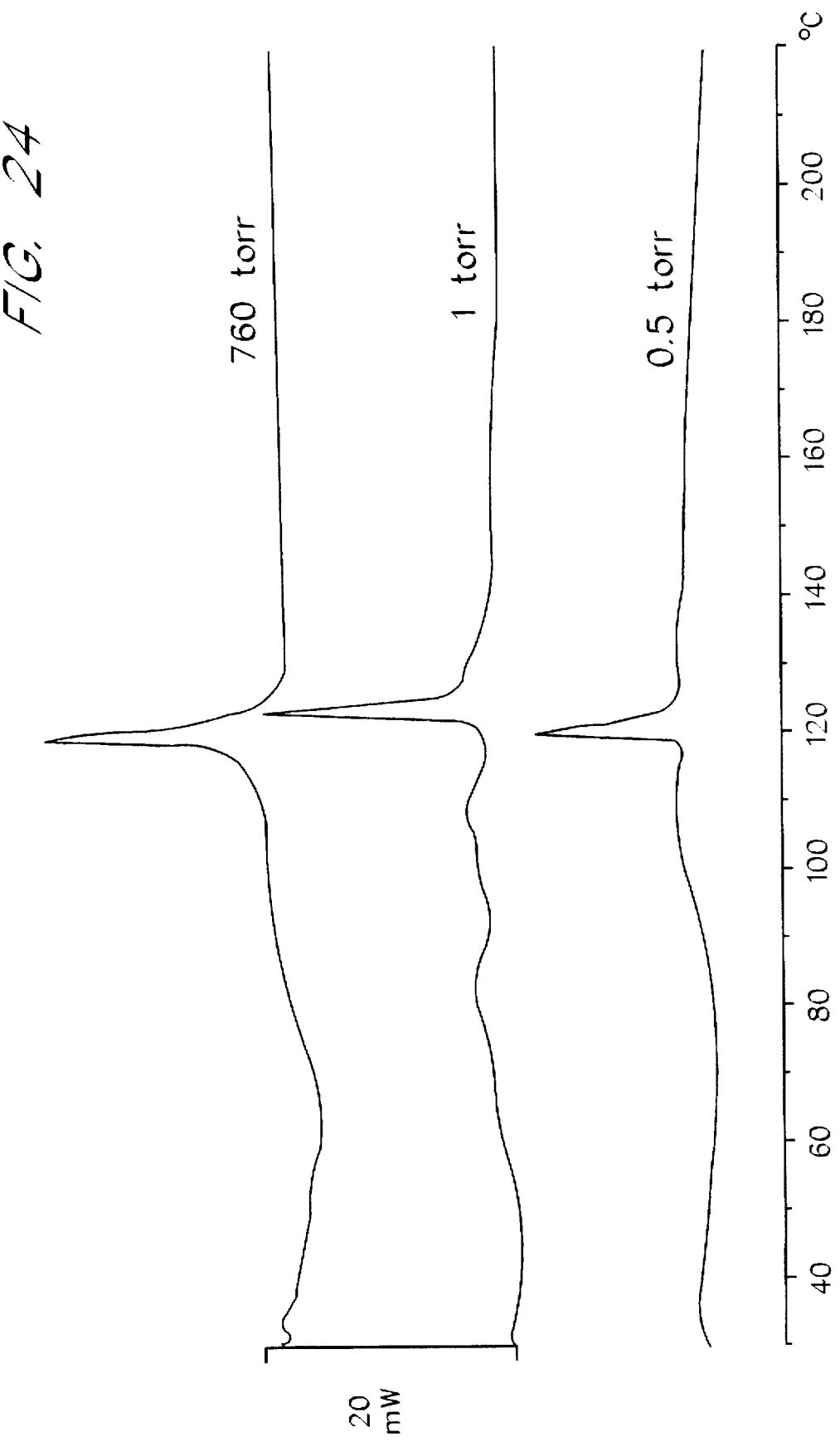
FIG. 24 is a DSC profile of $Na_2SiO_3·2.15\ H_2O_2$ at 760 torr, 1 torr and 0.5 torr.

FIG. 24 is a DSC profile of $Na_2SiO_3 \cdot 2.15\ H_2O_2$ at 760 torr, 1 torr and 0.5 torr. Exothermic peaks under atmospheric and reduced pressure indicated that most of the $H_2O_2$ had decomposed under these conditions.

Figure 25:
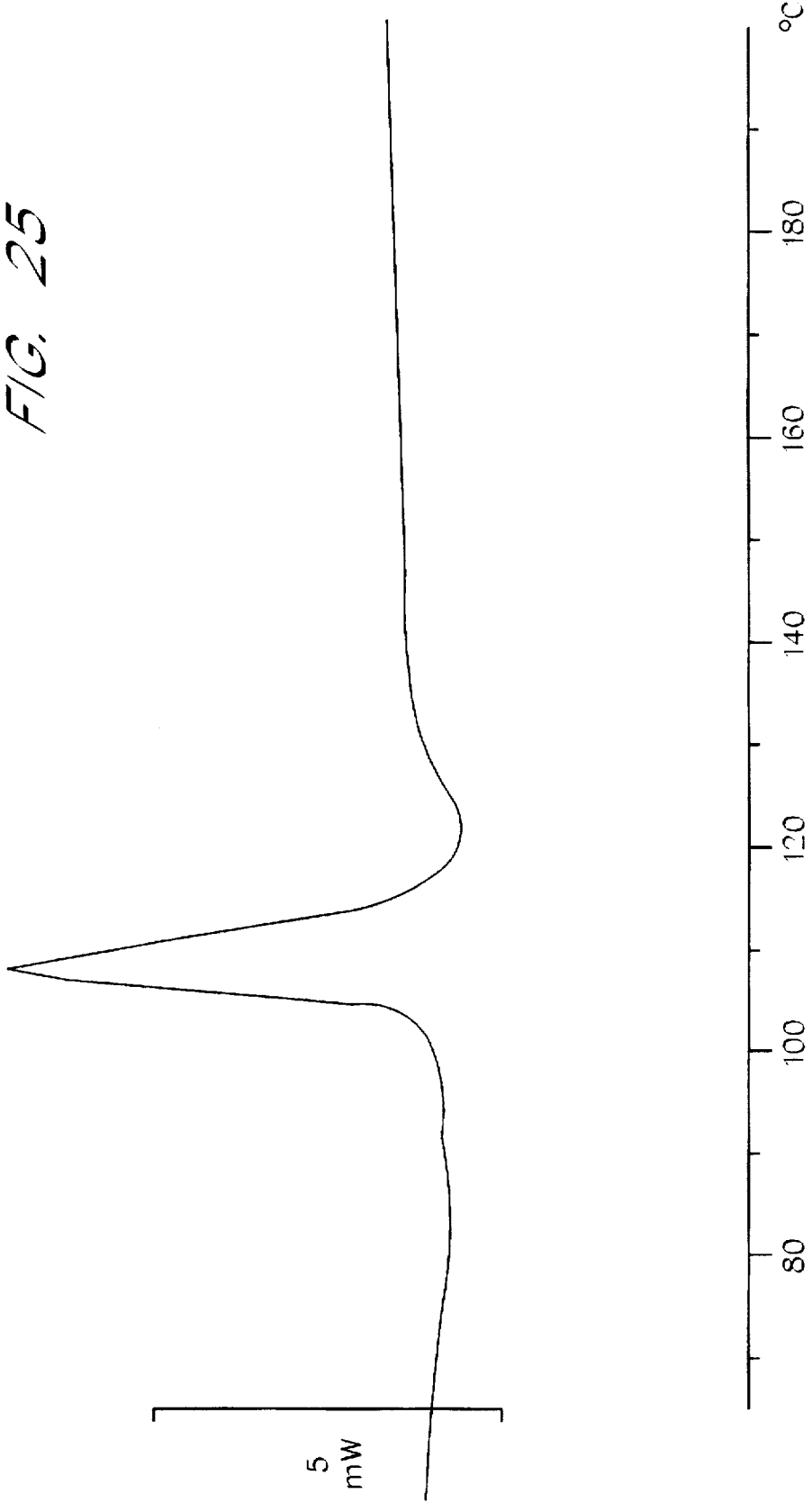
FIG. 25 is a DSC profile of $Na_2Si_3O_7·0.68\ H_2O_2$ at 760 torr.

FIG. 25 is a DSC profile of $Na_2Si_3O_7 \cdot 0.68\ H_2O_2$ at 760 torr. An exothermic peak indicated that most of the $H_2O_2$ had decomposed under atmospheric pressure.

Table 45 below summarizes the thermal behavior of peroxide complexes in DSC studies.

TABLE 45

| Complex | Thermal behavior in DSC | | Figure No. |
|---|---|---|---|
| | at 1 atmosphere (760 torr) | under vacuum | |
| $K_2C_2O_4 \cdot 1H_2O_2$ | endo+exo | endo | 10 |
| $Na_4P_2O_7 \cdot nH_2O_2$ n=2, 3, 4, | endo | endo | 11A and 11B |
| $Na_3PO_4 \cdot 5H_2O_2$ | endo+exo | endo | 12 |
| $Na_2HPO_4 \cdot nH_2O_2$ n=1, 2 | endo | endo | 13 |
| $Na_5P_3O_{10} \cdot nH_2O_2$ n=1-2 | endo | endo | 14 |
| $K_3PO_4 \cdot 3.34H_2O_2$ | exo | endo+exo | 15 |
| $K_4P_2O_7 \cdot 7H_2O_2$ | endo+exo | endo | 16 |
| $K_2HPO_4 \cdot 3.15H_2O_2$ | endo+exo | endo | 17 |
| $KH_2PO_4 \cdot 1H_2O_2$ | endo | endo | 18 |
| $Na_2CO_3 \cdot 1.5H_2O_2$ | exo | endo+exo | 19 |
| $Ca_2P_2O_7 \cdot 3.42H_2O_2$ | endo | endo | 20 |
| $Mg_2P_2O_7 \cdot 4.60H_2O_2$ | endo+exo | endo | 21 |
| $Na_2SO_4 \cdot 1.28H_2O_2$ | endo | endo | 22 |
| $K_2SO_4 \cdot 0.62H_2O_2$ | endo | endo | 23 |
| $Na_2SiO_3 \cdot 2.15H_2O_2$ | exo | exo | 24 |
| $Na_2Si_3O_7 \cdot 0.68H_2O_2$ | exo | exo | 25 |

Efficacy Test Results

Previous examples, e.g. Examples 17 and 18, demonstrated that inorganic peroxide complexes were capable of providing sterilization in connection with the techniques described herein and elesewhere under vacuum conditions. In order to demonstrate that those inorganic complexes were capable of providing sterilization under atmospheric conditions, we tested the sterilization efficacy of a number of compounds. Example 46A provides results in which the sterilization occurred at one atmosphere and low temperature ($\leq 60°$ C.) for a complex with an endothermic peak only in DSC at one atmosphere. Example 46B provides the results in which the sterilization occurred at one atmosphere and low temperature ($\leq 60°$ C.) for a complex with both endothermic and exothermic peaks in DSC at one atmosphere. Example 46C provides the results in which the sterilization occurred at one atmosphere and low temperature ($\leq 60°$ C.) for a complex with an exothermal peak only in DSC at one atmosphere. Example 47 provides the results in which the sterilization occurred at one atmosphere and the complex was heated using a complex with an only endothermic peak in DSC at one atmosphere. Example 48 provides the results in which the sterilization occurred at one atmosphere and the complex was heated using a complex with both endothermic and exothermic peaks at one atmosphere. As seen below, under these conditions, efficacious sterilization could be achieved at one atmosphere pressure using these complexes, even for a complex having only an exothermic peak in DSC. As discussed above, it is believed that in certain instances an endothermic peak is masked in DSC by an exothermic peak occurring within the same temperature range, accounting for the efficacious sterilization seen using complexes exhibiting only an exothermic peak on DSC.

EXAMPLE 46A

Sterilization Using $KH_2PO_4 \cdot H_2O_2$ Peroxide Complex (1 Atm. and Low Temperature)

A self-sterilizing pouch was assembled as follows: A stainless steel blade having $7.7 \times 10^5$ *B. stearothermophilus* spores in its surface was placed in a sterile petri dish (60×15 mm). 2 grams of $KH_2PO_4 \cdot H_2O_2$ complex powder (containing 20.31% wt of $H_2O_2$ was placed in another petri dish. Both dishes were inserted together into a 100×250 mm pouch formed of TYVEK™/MYLAR™. The pouch was sealed and exposed to room temperature (approx. 23° C.), 40° C. (in an incubator) and 60° C. (in an oven) for different time periods. The sterility test results are summarized in Table 46A.

TABLE 46A

| Exposure Temperature | Exposure Time (positives/samples) | | | | |
|---|---|---|---|---|---|
| | 1h | 2h | 4h | 6h | 8h |
| 23° C. (RT) | + | + | − | − | − |
| 40° C. | + | + | − | − | − |
| 60° C. | + | − | − | − | − |

EXAMPLE 46B

Sterilization Using $K_2C_2O_4 \cdot H_2O_2$ Peroxide Complex (1 Atm and Low Temperature)

A self-sterilizing pouch was assembled as follows: A stainless steel blade having $1.34 \times 10^6$ *B. subtilis* var. niger spores on its surface was placed in a sterile petri dish (60×15 mm). 2 grams of $K_2C_2O_4.H_2O_2$ complex powder (containing 14.21% wt of $H_2O_2$) was placed in another petri dish. Both dishes were inserted together into a 100×250 mm pouch formed of MYLAR™/MYLAR™. The pouch was sealed and exposed to 40° C. (in an incubator) and 60° C. (in an oven) for different time periods. The sterility test results are summarized in Table 46B.

TABLE 46B

| Exposure    | Exposure Time (positives/samples) |     |     |     |     |
|-------------|-----|-----|-----|-----|-----|
| Temperature | 8h  | 16h | 24h | 48h | 72h |
| 40° C.      | N/A | N/A | +   | +   | −   |
| 60° C.      | +   | −   | −   | −   | −   |

EXAMPLE 46C

Sterilization Using $Na_2CO_3.1.5\ H_2O_2$ Peroxide Complex (1 Atm and Low Temperature)

A self-sterilizing pouch was assembled as follows: A stainless steel blade having $1.34\times10^6$ B. subtilis var. niger spores on its surface was placed in a sterile petri dish (60×15 mm). 2 grams of $Na_2CO_3.1.5\ H_2O_2$ complex powder (containing 27.78% wt of $H_2O_2$, Fluka) was placed in another petri dish. Both dishes were inserted together into a 100×250 mm pouch formed of MYLAR™/MYLAR™. The pouch was sealed and exposed to 60° C. (in an oven) for different time periods. The sterility test results are summarized in Table 46C.

TABLE 46C

| Exposure    | Exposure Time (positives/samples) |     |     |
|-------------|-----|-----|-----|
| Temperature | 24h | 48h | 72h |
| 60° C.      | +   | −   | −   |

EXAMPLE 47

Sterilization Using $Na_4P_2O_7.3\ H_2O_2$ Peroxide Complex (1 Atm and Elevated Complex Heating Temperature)

$Na_4P_2O_7.3\ H_2O_2$ (wt %=27%) was used in the sterilization apparatus shown in FIG. 8. The sterilization parameters were as follows: size of chamber=6.25"×6.25"×7" (4.5 liters); temperature of chamber=40° C.; pressure of chamber=760 torr; heating temperature=175°–180° C. B. stearothermophilus ($1.5\times10^6$/scalpel blade) was used as the inoculant. The results are summarized in Tables 47A and 47B. As evidenced by Table 47A, complete sterilization of the scalpel blades located two inches above the heating apparatus was achieved with just 0.01 g of the complex. In contrast, in the inoculates located at the bottom of the chamber, 0.3 g of the complex was required for complete sterilization.

TABLE 47A

| | Sterility results (positives/samples) with samples located 2" above the heated plate | | |
|---|---|---|---|
| Wt. of Complex | 2/10 cycle* | 2/15 cycle | 2/30 cycle |
| 0.0 g  | 2/2 | 2/2 | 2/2 |
| 0.01 g | 0/2 | 0/2 | 0/2 |
| 0.03 g | 0/2 | 0/2 | 0/2 |
| 0.05 g | 0/2 | 0/2 | 0/2 |

*Cycle Time = Heating time (min.)/total exposure time (min.)

TABLE 47B

| | Sterility results (positives/samples) with samples located on the bottom of the chamber | | |
|---|---|---|---|
| Wt. of Complex | 2/10 cycle* | 2/15 cycle | 2/30 cycle |
| 0.0 g | 2/2 | 2/2 | 2/2 |
| 0.1 g | 2/2 | 2/2 | 2/2 |
| 0.2 g | 1/2 | 1/2 | 1/2 |
| 0.3 g | 0/2 | 0/2 | 0/2 |
| 0.5 g | 0/2 | 0/2 | 0/2 |

*Cycle Time = Heating time (min.)/total exposure time (min.)

EXAMPLE 48

Sterilization Using $K_2C_2O_4O_2$ Peroxide Complex (1 Atm and Elevated Complex Heating Temperature)

$K_2C_2O_4.H_2O_2$ (wt %=16.3%) was used in the sterilization apparatus shown in FIG. 8. The sterilization parameters were as outlined in Example 47, with the exception that the heating temperature was 155°–160° C. In this experiment, inoculated scalpel blades were placed only above the heating plate. The results are summarized in Table 48.

TABLE 48

| | Sterility results (positives/samples) with samples located 2" above the heated plate | | |
|---|---|---|---|
| Wt. of Complex | 2/10 cycle* | 2/15 cycle | 2/30 cycle |
| 0.0 g  | 2/2 | 2/2 | 2/2 |
| 0.01 g | 1/2 | 1/2 | 0/2 |
| 0.03 g | 0/2 | 0/2 | 0/2 |
| 0.05 g | 0/2 | 0/2 | 0/2 |
| 0.1 g  | 0/2 | 0/2 | 0/2 |
| 0.2 g  | 0/2 | 0/2 | 0/2 |

*Cycle Time = Heating time (min.)/total exposure time (min.)

With the potassium oxalate complex, complete sterilization occurred using 0.01 g with 30 minutes exposure. Complete sterilization was seen with 0.03 g of the complex in all three cycles.

In summary, $H_2O_2$ can be released from the complex at a pressure of one atmosphere and at room temperature. This release can be facilitated with elevated temperature and reduced pressure.

System for Release of Vapor from Hydrogen Peroxide Complexes

The apparatus discussed above in connection with FIGS. 7A and 7B can be used in a system for the release of hydrogen peroxide vapor from hydrogen peroxide complexes. Such an apparatus can be used in connection with peroxide complexes formed into disks. Nevertheless, we have found that vapor can be more thoroughly and efficiently released when used in powdered form. Powder can be placed into the apparatus using the same mechanism described above in connection with FIGS. 7A and 7B. However, another method of introduction of powder is accomplished by initially applying the powder to a high temperature adhesive tape. For example, the 3M Corporation manufactures high temperature tape 9469 which makes use of their adhesive A10. The powder can be dusted onto the adhesive and the tape introduced into the chamber for release of hydrogen peroxide vapor. Another exemplary adhesive tape for this purpose can be formed of 3M tape 9485 with 3M adhesive A25.

Conclusion

It should be noted that the present invention is not limited to only those embodiments described in the Detailed Description. Any embodiment which retains the spirit of the present invention should be considered to be within its scope. However, the invention is only limited by the scope of the following claims.

We claim:

1. An apparatus for hydrogen peroxide sterilization of an article, comprising:
   a container for holding the article to be sterilized; and
   a source of hydrogen peroxide vapor in fluid communication with said container, said source comprising an inorganic hydrogen peroxide complex which does not decompose to form a hydrohalic acid, said source configured so that said vapor can contact said article to effect sterilization.

2. The apparatus of claim 1, wherein said container includes a breathable barrier.

3. The apparatus of claim 1, wherein said source of hydrogen peroxide vapor is located within the container.

4. The apparatus of claim 1, wherein said source of hydrogen peroxide vapor is located in an enclosure which is in fluid communication with the container.

5. The apparatus of claim 4, additionally comprising a valve between said enclosure and said container.

6. The apparatus of claim 1, further comprising a heater adapted to heat the inorganic hydrogen peroxide complex.

7. The apparatus of claim 1, wherein the inorganic hydrogen peroxide complex is within said container, said apparatus further comprising a heater adapted to heat the container.

8. The apparatus of claim 4, further comprising a heater adapted to heat the enclosure.

9. The apparatus of claim 4, further comprising a heater adapted to heat the complex.

10. The apparatus of claim 1, further comprising a pump to evacuate the container.

11. The apparatus of claim 4, further comprising a pump adapted to evacuate the container and the enclosure.

12. The apparatus of claim 11, whereby the pump is adapted to evacuate the container independently of the enclosure.

13. The apparatus of claim 4, further comprising a first pump adapted to evacuate the container and a second pump adapted to evacuate the enclosure.

14. The apparatus of claim 10, additionally comprising a first vent valve adapted to vent the container.

15. The apparatus of claim 11, additionally comprising a first vent valve adapted to vent the container and a second vent valve adapted to vent the enclosure independently of the first vent valve.

16. The apparatus of claim 1, further comprising a mechanism for generating a plasma.

17. The apparatus of claim 16, whereby the plasma is generated within the container.

18. The apparatus of claim 1, wherein said complex is a hydrogen peroxide complex of a phosphate or condensed phosphate salt.

19. The apparatus of claim 1, wherein said complex is a hydrogen peroxide complex of an oxalate salt.

20. The apparatus of claim 1, wherein said complex is a hydrogen peroxide complex of a carbonate salt.

21. The apparatus of claim 1, wherein said complex is a hydrogen peroxide complex of a sulfate salt.

22. The apparatus of claim 1, wherein said complex is a hydrogen peroxide complex of a silicate salt.

23. The apparatus of claim 1, wherein said complex is in a solid phase.

24. A method for hydrogen peroxide vapor sterilization of an article, comprising contacting the article with hydrogen peroxide vapor released from an inorganic hydrogen peroxide complex to sterilize the article, wherein said peroxide complex does not decompose to a hydrohalic acid.

25. The method of claim 24, wherein the complex has less than 10% water.

26. The method of claim 24, wherein the method is performed at a temperature of 25° C. or less.

27. The method of claim 24, further comprising heating said complex to facilitate the release of said vapor from said complex.

28. The method of claim 27, wherein said heating is performed at a rate of at least 5° C./minute.

29. The method of claim 27, wherein said heating is performed at a rate of at least 10° C./minute.

30. The method of claim 27, wherein said heating is performed at a rate of at least 50° C./minute.

31. The method of claim 27, wherein said heating is performed at a rate of at least 1000° C./minute.

32. The method of claim 27, wherein said heating comprises contacting said complex with a pre-heated heater.

33. The method of claim 27, wherein said complex is heated to a temperature greater than 86° C.

34. The method of claim 24, wherein the method is performed at atmospheric pressure.

35. The method of claim 24, wherein the method is performed at a subatmospheric pressure.

36. The method of claim 35, wherein the article is within a container, further comprising evacuating the container.

37. The method of claim 35, wherein said pressure is less than 50 torr.

38. The method of claim 37, wherein said pressure is less than 20 torr.

39. The method of claim 38, wherein said pressure is less than 10 torr.

40. The method of claim 36, wherein said hydrogen peroxide vapor is released from said inorganic hydrogen peroxide complex located within an enclosure which is in fluid communication with said container.

41. The method of claim 40, wherein the pressure of the enclosure and the pressure of the container are different.

42. The method of claim 36, wherein the evacuating step is conducted before the step of contacting the article with the vapor.

43. The method of claim 36, further comprising generating a plasma around said article after introducing said vapor into said container.

44. The method of claim 43, wherein said plasma is generated inside the container.

45. The method of claim 43, wherein said plasma is generated outside the container and flowed inside the container and around said article.

46. The method of claim 24, wherein the contacting step comprises pressure pulsing of said vapor.

47. The method of claim 24, wherein the inorganic complex is a complex of a phosphate or condensed phosphate salt with hydrogen peroxide.

48. The method of claim 47, wherein the salt is of potassium or sodium, magnesium or calcium.

49. The method of claim 48, wherein said inorganic complex is a hydrogen peroxide complex with $Na_4P_2O_7$.

50. The method of claim 49, wherein said inorganic complex has two or more molecules of hydrogen peroxide.

51. The method of claim 50, wherein said inorganic complex is $Na_4P_2O_7 \cdot 3\ H_2O_2$.

52. The method of claim 48, wherein said inorganic complex is a hydrogen peroxide complex with $Na_3PO_4$.

53. The method of claim 48, wherein said inorganic complex is a hydrogen peroxide complex with $Na_2HPO_4$.

54. The method of claim 48, wherein said inorganic complex is a hydrogen peroxide complex with $Na_5P_3{}_{10}$.

55. The method of claim 48, wherein said inorganic complex is a hydrogen peroxide complex with $K_3PO_4$.

56. The method of claim 48, wherein said inorganic complex is a hydrogen peroxide complex with $K_4P_2O_7$.

57. The method of claim 56, wherein said inorganic complex has two or more $H_2O_2$ molecules.

58. The method of claim 48, wherein said inorganic complex is a hydrogen peroxide complex with $K_2HPO_4$.

59. The method of claim 48, wherein said inorganic complex is a hydrogen peroxide complex with $KH_2PO_4$.

60. The method of claim 59, wherein said inorganic complex is $KH_2PO_4 \cdot OH_2O_2$.

61. The method of claim 47, wherein said inorganic complex is a hydrogen peroxide complex with $Ca_2P_2O_7$.

62. The method of claim 47, wherein said inorganic complex is a hydrogen peroxide complex with $Mg_2P_2O_7$.

63. The method of claim 24, wherein the inorganic complex is a complex of hydrogen peroxide with an oxalate salt.

64. The method of claim 63, wherein said inorganic complex is a hydrogen peroxide complex with $K_2C_2O$.

65. The method of claim 64, wherein said inorganic complex is $K_2C_2O_4 \cdot H_2O_2$.

66. The method of claim 24, wherein the inorganic complex is a complex of hydrogen peroxide with a carbonate salt.

67. The method of claim 66, wherein the carbonate salt is a salt of sodium, potasssium or rubidium.

68. The method of claim 67, wherein the inorganic complex is a complex of hydrogen peroxide with $Na_2CO_3$.

69. The method of claim 68, wherein the inorganic complex is $Na_2CO_3 \cdot 1.5\ H_2O_2$.

70. The method of claim 67, wherein the inorganic complex is a complex of hydrogen peroxide with $K_2CO_3$.

71. The method of claim 67, wherein the inorganic complex is a complex of hydrogen peroxide with $NaHCO_3$.

72. The method of claim 67, wherein the inorganic complex is a complex of hydrogen peroxide with $KHCO_3$.

73. The method of claim 67, wherein the inorganic complex is a complex of hydrogen peroxide with $Rb_2CO_3$.

74. The method of claim 24, wherein the inorganic complex is a complex of hydrogen peroxide with a sulfate salt.

75. The method of claim 74, wherein the sulfate salt is a sodium or potassium salt.

76. The method of claim 75, wherein the inorganic complex is a complex of hydrogen peroxide with $Na_2SO_4$.

77. The method of claim 75, wherein the inorganic complex is a complex of hydrogen peroxide with $K_2SO_4$.

78. The method of claim 24, wherein the inorganic complex is a complex of hydrogen peroxide with a silicate salt.

79. The method of claim 78, wherein the silicate salt is a sodium salt.

80. The method of claim 79, wherein the inorganic complex is a complex of hydrogen peroxide with $Na_2SiO_3$.

81. The method of claim 79, wherein the inorganic complex is a complex of hydrogen peroxide with $Na_2Si_3O_7$.

82. The method of claim 24, wherein the inorganic complex releases hydrogen peroxide at atmospheric pressure and room temperature.

83. The method of claim 24, wherein the hydrogen peroxide is released at a pressure less than atmospheric pressure.

84. The method of claim 24, wherein contacting step additionally comprises releasing hydrogen peroxide from a second source thereof.

85. The method of claim 84, wherein the second source is a second hydrogen peroxide complex.

86. The method of claim 85, wherein the second hydrogen peroxide complex is an organic hydrogen peroxide complex.

87. The method of claim 24, wherein the hydrogen peroxide vapor is released from at least two different hydrogen peroxide complexes.

88. The method of claim 87, wherein the different hydrogen peroxide complexes are physically mixed.

89. The method of claim 87, wherein the different hydrogen peroxide complexes are chemically mixed.

90. A method for hydrogen peroxide vapor sterilization of an article, comprising contacting the article with hydrogen peroxide vapor released from a $Na_4P_2O_7$ hydrogen peroxide complex by heating the complex so as to produce hydrogen peroxide vapor that can contact and sterilize the article.

91. The method of claim 90, wherein the $Na_4P_2O_7$ complex is $Na_4P_2O_7 \cdot 3\ H_2O_2$.

92. The method of claim 90, wherein the contacting step is at atmospheric pressure.

93. The method of claim 90, wherein the complex is heated to a temperature of approximately 175° C. to release said vapor.

94. The method of claim 90, additionally comprising placing said article into a container prior to the contacting step.

95. The method of claim 94, further comprising evacuating the container before contacting said article with said vapor, such that when said vapor is introduced into said container, the container is at a pressure of less than 50 torr.

96. A method for hydrogen peroxide sterilization of an article, comprising:
   placing the article in a container;
   placing a hydrogen peroxide complex of an inorganic salt which does not decompose to form a hydrohalic acid into vapor communication with said container; and
   allowing said container to stand at a temperature below about 70° C. for a time sufficient to release hydrogen peroxide vapor from said complex to effect sterilization of the article.

97. The method of claim 96, wherein said container is a pouch, chamber or room.

98. The method of claim 96, wherein said inorganic salt is a salt of a phosphate or condensed phosphate.

99. The method of claim 96, wherein said inorganic salt is a salt of an oxalate.

100. The method of claim 96, wherein said inorganic salt is a salt of a carbonate.

101. The method of claim 96, wherein said inorganic salt is a salt of a sulfate.

102. The method of claim 96, wherein said inorganic salt is a salt of a silicate.

103. The method of claim 96, wherein said container is allowed to stand at a pressure less than atmospheric pressure.

104. The method of claim 96, wherein said container is allowed to stand at a temperature below about 40° C.

105. The method of claim 96, wherein said complex is heated to a temperature greater than 23° C. to facilitate release of said vapor.

106. The method of claim 96, wherein said hydrogen peroxide complex is in the form of a powder.

107. The method of claim 96, wherein said hydrogen peroxide complex is in the form of a tablet.

108. The method of claim 96, wherein the hydrogen peroxide complex is within an enclosure.

109. The method of claim 108, wherein said enclosure is inside said container.

110. The method of claim 108, wherein said enclosure is outside said container.

111. The method of claim 110, wherein said enclosure is selectively separated from said container by a valve.

112. The method of claim 110, additionally comprising detaching said enclosure from said container.

113. The method of claim 96, wherein the container is sealed.

114. The method of claim 113, wherein the container is sealed with a gas permeable material.

115. The method of claim 114, wherein said gas permeable material is TYVEK™.

116. The method of claim 114, wherein said gas permeable material is CSR wrap.

117. The method of claim 114, wherein said gas permeable material is paper.

118. The method of claim 96, additionally comprising exposing said article to plasma.

119. The method of claim 112, additionally comprising exposing said article to plasma after detaching the enclosure from the container.

120. A method for hydrogen peroxide sterilization of an article having an exterior and a narrow lumen therein, comprising:
   connecting a vessel containing a hydrogen peroxide complex to the lumen of the article, said hydrogen peroxide being a complex which does not decompose to form a hydrohalic acid;
   placing the article within a container;
   evacuating the container; and
   contacting the lumen of the article with hydrogen peroxide vapor released from said hydrogen peroxide complex.

121. The method of claim 120, wherein said complex is a complex of a phosphate or condensed phosphate salt.

122. The method of claim 120, wherein said complex is a complex of an oxalate salt.

123. The method of claim 120, wherein said complex is a complex of a carbonate salt.

124. The method of claim 120, wherein said complex is a complex of a sulfate salt.

125. The method of claim 120, wherein said complex is a complex of a silicate salt.

126. The method of claim 120, additionally comprising contacting the exterior of the article with a second source of sterilant.

127. The method of claim 126, wherein the second source of sterilant is the same hydrogen peroxide complex as in said vessel.

128. The method of claim 126, wherein the second source of sterilant is a different hydrogen peroxide complex as in said vessel.

129. The method of claim 126, wherein the second source of sterilant is liquid hydrogen peroxide.

130. The method of claim 126, wherein the second source of sterilant is chlorine dioxide.

131. The method of claim 120, additionally comprising exposing said article to plasma.

* * * * *

UNITED STATES PATENT AND TRADEMARK OFFICE
CERTIFICATE OF CORRECTION

PATENT NO. : 5,785,934
DATED : July 28, 1998
INVENTOR(S) : Jacobs et al.

It is certified that error appears in the above-identified patent and that said Letters Patent is hereby corrected as shown below:

At Claim 54, please delete "$Na_5P_{310}$" and replace with --$Na_5P_3O_{10}$--.

At Claim 60, please delete "$KH_2PO_4OH_2O_2$" and replace with --$KH_2PO_4 \bullet H_2O_2$--.

At Claim 64, please delete "$K_2C_2O$" and replace with --$K_2C_2O_4$--.

Signed and Sealed this

Twenty-fifth Day of May, 1999

Attest:

Q. TODD DICKINSON

*Attesting Officer*   *Acting Commissioner of Patents and Trademarks*